(12) United States Patent
Desai et al.

(10) Patent No.: US 9,556,148 B2
(45) Date of Patent: Jan. 31, 2017

(54) N-CYANOMETHYLAMIDES AS INHIBITORS OF JANUS KINASE

(71) Applicant: CADILA HEALTHCARE LIMITED, Ahmedabad, Gujarat (IN)

(72) Inventors: Ranjit Desai, Gujarat (IN); Jigar Desai, Gujarat (IN); Pankaj Patel, Gujarat (IN)

(73) Assignee: Cadila Healthcare Limited, Ahmedabad (IN)

( * ) Notice: Subject to any disclaimer, the term of this patent is extended or adjusted under 35 U.S.C. 154(b) by 0 days.

(21) Appl. No.: 14/910,028

(22) PCT Filed: Aug. 6, 2014

(86) PCT No.: PCT/IN2014/000515
§ 371 (c)(1),
(2) Date: Feb. 4, 2016

(87) PCT Pub. No.: WO2015/019365
PCT Pub. Date: Feb. 12, 2015

(65) Prior Publication Data
US 2016/0176849 A1    Jun. 23, 2016

(30) Foreign Application Priority Data

Aug. 7, 2013    (IN) .................. 2611/MUM/2013

(51) Int. Cl.
| | | |
|---|---|---|
| *C07D 401/14* | (2006.01) | |
| *C07D 417/14* | (2006.01) | |
| *C07D 413/14* | (2006.01) | |
| *C07D 403/14* | (2006.01) | |
| *C07D 409/10* | (2006.01) | |
| *C07D 409/14* | (2006.01) | |
| *C07D 498/08* | (2006.01) | |
| *C07D 513/08* | (2006.01) | |
| *C07D 401/12* | (2006.01) | |
| *C07D 403/12* | (2006.01) | |
| *C07D 405/14* | (2006.01) | |
| *C07D 407/12* | (2006.01) | |
| *C07D 407/14* | (2006.01) | |
| *C07D 409/12* | (2006.01) | |
| *C07D 471/08* | (2006.01) | |
| *C07D 491/056* | (2006.01) | |
| *C07D 491/08* | (2006.01) | |

(Continued)

(52) U.S. Cl.
CPC ........... *C07D 401/14* (2013.01); *C07D 401/12* (2013.01); *C07D 403/12* (2013.01); *C07D 403/14* (2013.01); *C07D 405/14* (2013.01); *C07D 407/12* (2013.01); *C07D 407/14* (2013.01); *C07D 409/10* (2013.01); *C07D 409/12* (2013.01); *C07D 409/14* (2013.01); *C07D 413/14* (2013.01); *C07D 417/14* (2013.01); *C07D 471/08* (2013.01); *C07D 491/056* (2013.01); *C07D 491/08* (2013.01); *C07D 491/107* (2013.01); *C07D 495/08* (2013.01); *C07D 498/08* (2013.01); *C07D 513/08* (2013.01)

(58) Field of Classification Search
CPC ... C07D 401/14; C07D 417/14; C07D 413/14; C07D 403/14; C07D 409/10; C07D 409/14; C07D 498/08; C07D 513/08
See application file for complete search history.

(56) References Cited

U.S. PATENT DOCUMENTS

| | | |
|---|---|---|
| 2002/0111358 A1 | 8/2002 | Nishiyama et al. |
| 2008/0045517 A1 | 2/2008 | Foote et al. |

FOREIGN PATENT DOCUMENTS

| | | |
|---|---|---|
| WO | 97/37979 | 10/1997 |
| WO | 01/87838 A1 | 11/2001 |
| WO | 02/36562 A2 | 5/2002 |

(Continued)

OTHER PUBLICATIONS

Ortmann, R. A., et al., "Janus kinases and signal transducers and activators of transcription: their roles in cytokine signaling, development and immunoregulation", Arthritis Res. 2000, 2, pp. 16-32.

(Continued)

*Primary Examiner* — Kahsay Habte
(74) *Attorney, Agent, or Firm* — Ladas & Parry LLP

(57) ABSTRACT

The present invention relates to compounds of general formula (1) that are inhibitors of Janus Kinase (JAK), a family of tyrosine kinases that are involved in inflammatory conditions, autoimmune diseases, proliferative diseases, allergy, transplant rejection, diseases involving impairment of cartilage turnover, congenital cartilage malformations, and/or diseases associated with hypersecretion of IL6 or interferons. In particular, the compound of the invention inhibits JAK1 and/or JAK2 and/or JAK3 sub families. The present invention also provides methods for the production of the compounds of the invention, pharmaceutical compositions comprising the compounds of the invention, their tautomeric forms, and their pharmaceutically acceptable salts

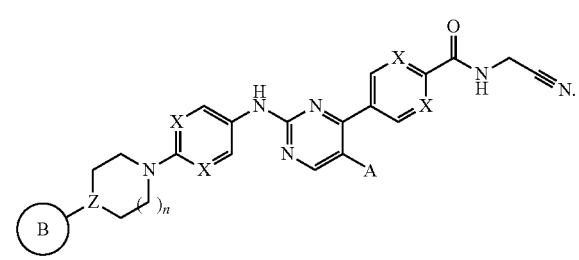

Formula 1

10 Claims, No Drawings

(51) Int. Cl.
*C07D 491/107* (2006.01)
*C07D 495/08* (2006.01)

(56) References Cited

FOREIGN PATENT DOCUMENTS

| | | |
|---|---|---|
| WO | 2004/039780 A1 | 5/2004 |
| WO | 2005/108402 A1 | 11/2005 |
| WO | 2005/124342 A2 | 12/2005 |
| WO | 2007/089768 A2 | 8/2007 |
| WO | 2008/060621 A2 | 5/2008 |
| WO | 2008/109943 A1 | 9/2008 |
| WO | 2008/151183 A1 | 12/2008 |
| WO | 2009/029998 A1 | 3/2009 |
| WO | 2009/039257 A1 | 3/2009 |
| WO | 2009/051822 A1 | 4/2009 |
| WO | 2009/103032 A1 | 8/2009 |
| WO | 2009/136995 A2 | 11/2009 |
| WO | 2009/145856 A1 | 12/2009 |
| WO | 2009/158571 A1 | 12/2009 |
| WO | 2010/039518 A2 | 4/2010 |
| WO | 2010/075558 A2 | 7/2010 |
| WO | 2010/078369 A2 | 7/2010 |
| WO | 2010/085684 A1 | 7/2010 |
| WO | 2010/123870 A1 | 10/2010 |
| WO | 2010/129802 A1 | 11/2010 |
| WO | 2013/139717 A1 | 12/2010 |
| WO | 2011/017178 A1 | 2/2011 |
| WO | 2013/010453 A1 | 1/2013 |
| WO | 2013/093940 A1 | 6/2013 |

OTHER PUBLICATIONS

O'Shea, J.J., "Targeting the Jak/STAT pathway for immunosuppression", Ann. Rheum. Dis. 2004, 63, pp. ii67-ii71.

N-CYANOMETHYLAMIDES AS INHIBITORS OF JANUS KINASE

CROSS-REFERENCE TO RELATED APPLICATION

This U.S. application claims priority under 35 U.S.C. 371 to, and is a U.S. National Phase application of, the International Patent Application No. PCT/IN2014/00515, filed 6 Aug. 2014 which claims priority from India Application No. 2611/MUM/2013 filed on 7 Aug. 2013, the disclosures of which are incorporated in their entirety by reference herein.

FIELD OF THE INVENTION

The present invention relates to compounds of general formula (1) that are inhibitors of Janus Kinase (JAK), a family of tyrosine kinases that are involved in inflammatory conditions, autoimmune diseases, proliferative diseases, allergy, transplant rejection, diseases involving impairment of cartilage turnover, congenital cartilage malformations, and/or diseases associated with hypersecretion of IL6 or interferons. In particular, the compound of the invention inhibits JAK1 and/or JAK2 and/or JAK3 sub families. The present invention also provides methods for the production of the compounds of the invention, pharmaceutical compositions comprising the compounds of the invention, their tautomeric forms, and their pharmaceutically acceptable salts.

BACKGROUND OF THE INVENTION

Protein kinases (PKs) regulate diverse biological processes including cell growth, survival, differentiation, organ formation, morphogenesis, neovascularization, tissue repair, and regeneration. Protein kinases also play specialized roles in a host of human diseases like transplant rejection, rheumatoid arthritis, psoriasis, amyotrophic lateral sclerosis and multiple sclerosis as well as in solid and hematologic malignancies such as leukemias and lymphomas. Cytokines influence cell differentiation, proliferation and activation, and can modulate both pro-inflammatory and anti-inflammatory responses to allow the host to react appropriately to pathogens. Cytokine-stimulated immune and inflammatory responses contribute to pathogenesis of diseases: pathologies such as severe combined immunodeficiency (SCID) arise from suppression of the immune system, while a hyperactive or inappropriate immune/inflammatory response contributes to the pathology of autoimmune diseases (e.g., asthma, systemic lupus erythematosus, thyroiditis, myocarditis), and illnesses such as scleroderma and osteoarthritis (Ortmann, R. A., T. Cheng, et al. (2000) Arthritis Res 2(1): 16-32) Signaling of a wide range of cytokines involves the Janus kinase family (JAKs) of protein tyrosine kinases and Signal Transducers and Activators of Transcription (STATs). Janus kinase (JAK) is a family of intracellular non-receptor tyrosine kinases, ranging from 120-140 kDa, that transduce cytokine-mediated signals via the JAK-STAT pathway. The JAK family plays a role in the cytokine-dependent regulation of proliferation and function of cells involved in immune response. Currently, there are four known mammalian JAK family members: JAK 1, JAK 2, JAK 3 and TYK 2. JAK 1, JAK 2 and TYK 2 are ubiquitously expressed whereas JAK 3 is expressed in the myeloid and lymphoid lineages.

Vandeghinste et al. (WO 2005/124342) discovered JAK1 as a target whose inhibition might have therapeutic relevance for several diseases including OA. Knockout of the JAK1 gene in mice demonstrated that JAK1 plays essential and non-redundant roles during development.

JAK2 is a cytoplasmic protein-tyrosine kinase that catalyzes the transfer of the gamma-phosphate group of adenosine triphosphate to the hydroxyl groups of specific tyrosine residues in signal transduction molecules. JAK2 mediates signaling downstream of cytokine receptors after ligand-induced autophosphorylation of both receptor and enzyme. The main downstream effectors of JAK2 are a family of transcription factors known as signal transducers and activators of transcription (STAT) proteins. Studies have disclosed an association between an activating JAK2 mutation (JAK2V617F) and myleoproliferative disorders. The myeloproliferative disorders, a subgroup of myeloid malignancies, are clonal stem cell diseases characterized by an expansion of morphologically mature granulocyte, erythroid, megakaryocyte, or monocyte lineage cells. Myeloproliferative disorders (MPD) include polycythemia vera (PV), essential thrombocythemia (ET), myeloid metaplasia with myelofibrosis (MMM), chronic myelogenous leukemia (CML), chronic myelomonocytic leukemia (CMML), hypereosinophilic syndrome (HES), juvenile myelomonocytic leukemia (JMML) and systemic mast cell disease (SMCD). It has been suggested that abnormalities in signal transduction mechanisms, including constitutive activation of protein tyrosine kinases, initiate MPD. Jak2-/- mouse embryos are anemic and die around day 12.5 postcoitum due to the absence of definitive erythropoiesis.

JAK3 associates with the common gamma chain of the extracellular receptors for the following interleukins: IL-2, IL-4, IL-7, IL-9 and IL-15. A JAK3 deficiency is associated with an immune compromised (SCID) phenotype in both rodents and humans. The SCID phenotype of JAK3 (-/-) mammals and the lymphoid cell specific expression of JAK3 are two favorable attributes of a target for an immune suppressant. Data suggests that inhibitors of JAK3 could impede T-cell activation and prevent rejection of grafts following transplant surgery, or to provide therapeutic benefit to patients suffering autoimmune disorders. An important feature of JAK3 is that it specifically associates with the common cytokine receptor gamma chain which is a shared component of the receptors for IL-2, IL-4, IL-7, IL-9, and IL-15. Unlike the other JAK family members that are more widely expressed in many mammalian tissues, JAK3 expression seems to be mainly limited to the endoplasmic membranes of hematopoietic cells. JAK3 is validated by mouse and human genetics as an immune-suppression target (O'Shea J. et al. (2004)). JAK3 inhibitors were successfully taken into clinical development, initially for organ transplant rejection but later also in other immuno-inflammatory indications such as rheumatoid arthritis (RA), psoriasis and Crohn's disease.

Blocking signal transduction at the level of the JAK kinases holds promise for developing treatments for human cancers and arthritis. Inhibition of the JAK kinases is also envisioned to have therapeutic benefits in patients suffering from skin immune disorders such as psoriasis, and skin sensitization. In view of numerous conditions that are contemplated to benefit by treatment involving modulation of JAK pathways it is immediately apparent that new compounds that modulate JAK pathways and method of using these compounds should provide substantial therapeutic benefit to a wide variety of patients.

Patent applications from Portola (WO 2010/129802, WO 2009/145856, WO 2009/136995 etc.) discloses pyrimidine class of compounds as Spleen Tyrosine Kinases (SYK) or JAK inhibitors.

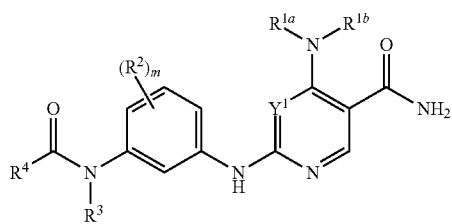

WO 2011/129802

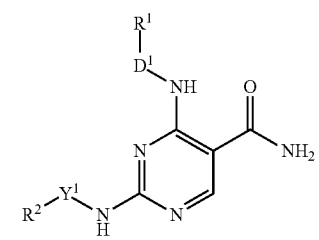

WO 2009/145856

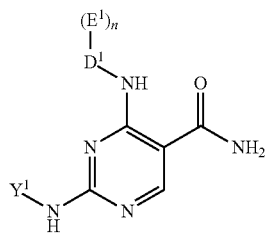

WO 2009/136995

Rigel has filed a number of patent applications (WO 2011/017178, WO 2010/085684, WO 2010/078369, WO 2010/075558 and WO 2010/039518 etc.) claiming pyrimidine class of compounds as useful modulators of JAK pathways or as inhibitors of JAK kinases particularly JAK-2, JAK-3 or both.

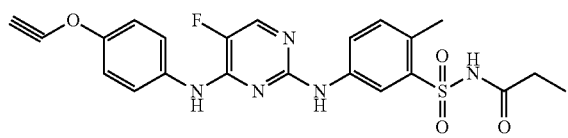

WO 2011/017178

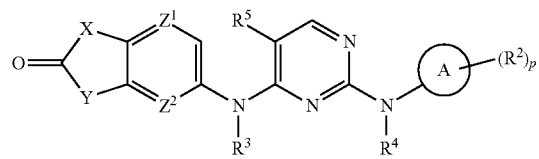

WO 2010/085684

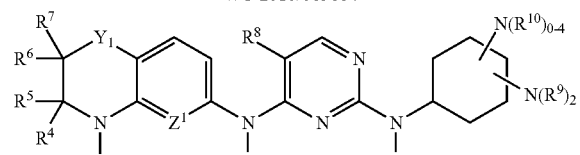

WO 2010/078369

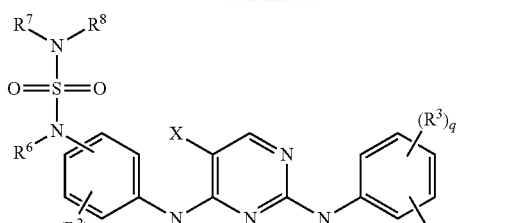

WO 2010/075558

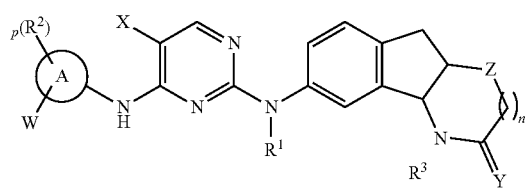

WO 2010/039518

Avila Therapeutics reported pyrimidine class of compounds as protein kinase inhibitors (WO 2010123870, WO 2009/158571, WO 2009/051822 and WO 2008/151183).

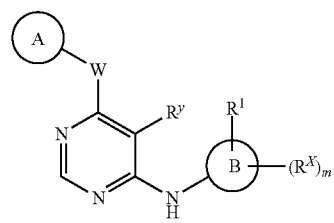

WO 2010/123870
WO 2009/051822

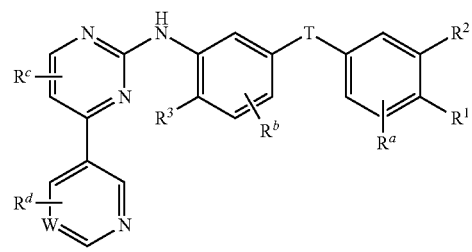

WO:2008151183

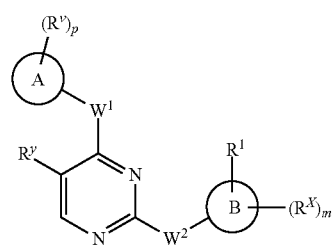

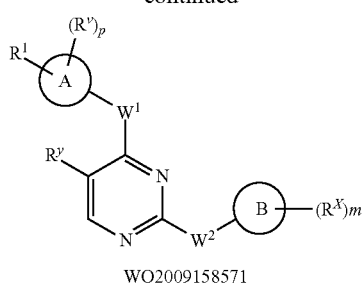

WO2009158571

Cytopia Research Pvt. Ltd reported phenyl amino pyrimidine class of compounds as protein kinase inhibitors including JAK (WO 2008109943, WO 2009029998).

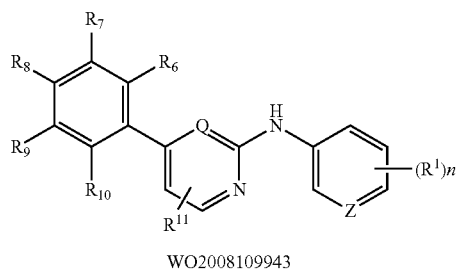

WO2008109943

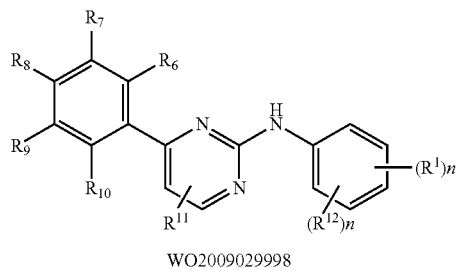

WO2009029998

Cytopia reported following two compounds in their patent application WO 2008109943. The reported in vitro JAK 2 and JAK-3 inhibition for compounds 2 is less than 1 µM and less than 20 µM respectively.

Compound 1

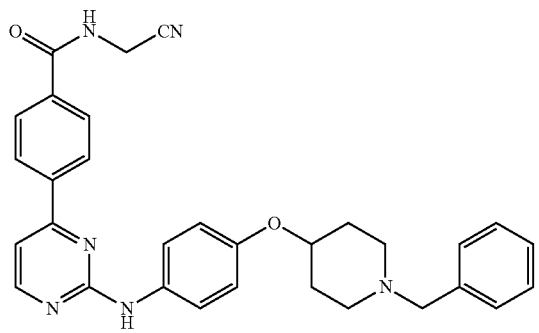

Compound 2

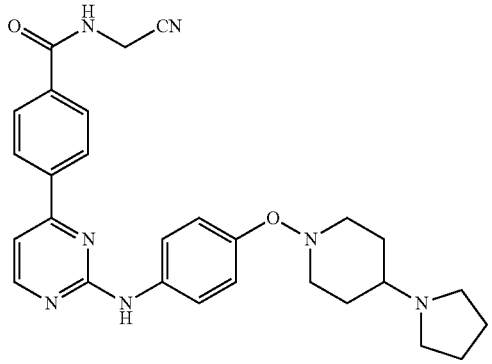

However, none of these compounds have reached the market and keeping in mind the huge unmet potential for such molecules, there is a need to develop compounds which modulate the JAK enzymes in a therapeutically effective way. We herein below disclose such novel molecules.

SUMMARY OF THE INVENTION

The present invention describes a group of novel compounds as JAK inhibitors useful for the treatment of autoimmune diseases, proliferative diseases, allergy, transplant rejection, diseases involving impairment of cartilage turnover, congenital cartilage malformations, and/or diseases associated with hypersecretion of IL6 or interferons. The novel compounds are defined by the general formula (1) below:

Formula 1

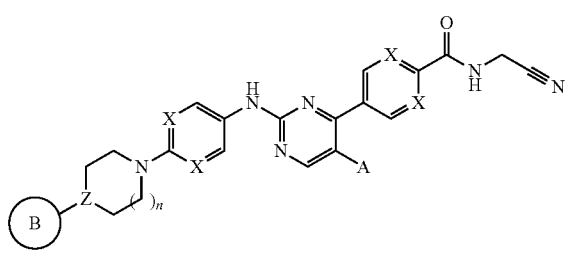

The compounds of the present invention are useful in the treatment of the human or animal body, by regulating Janus kinase (JAK). The compounds of this invention are therefore suitable for the treatment of autoimmune other related diseases.

EMBODIMENTS OF THE PRESENT INVENTION

The main objective of the present invention thus is to provide novel compounds of general formula (1), novel intermediates involved in their synthesis, their pharmaceutically acceptable salts, and pharmaceutical compositions containing them or their mixtures as therapeutic agents.

Formula 1

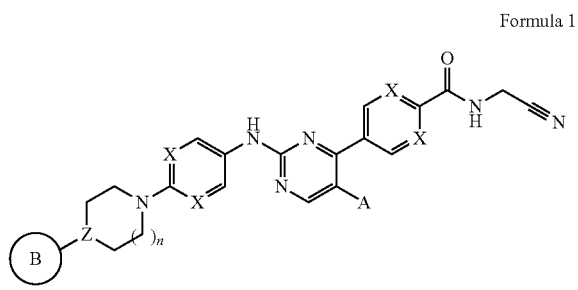

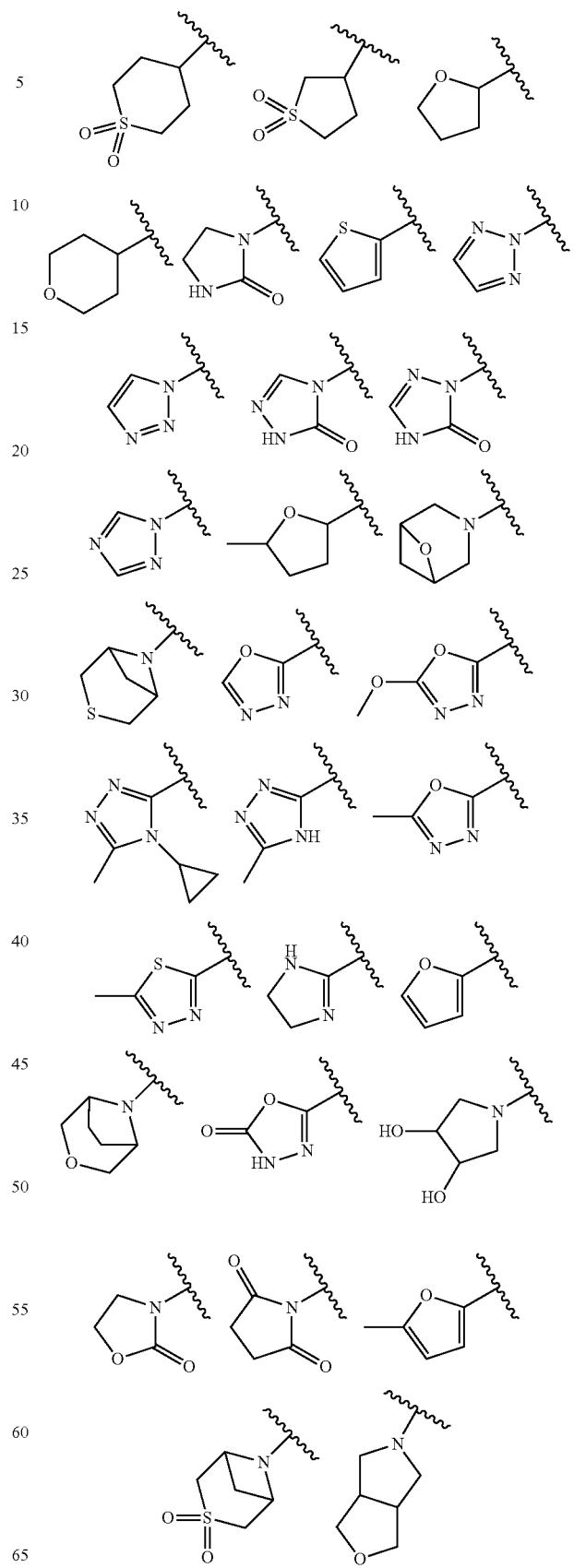

In an embodiment is provided processes for the preparation of novel compounds of general formula (1), novel intermediates involved in their synthesis, their pharmaceutically acceptable salts, and pharmaceutical compositions containing them.

In another embodiment is provided pharmaceutical compositions containing compounds of general formula (1), their pharmaceutically acceptable salts, comprising pharmaceutically acceptable carriers, solvents, diluents, excipients and other media normally employed in their manufacture.

In a further embodiment is provided the use of the novel compounds of the present invention in disease conditions developed by deregulation of JAK, by administering a therapeutically effective & non-toxic amount of the compounds of formula (1) or their pharmaceutically acceptable compositions to the mammals.

DETAILED DESCRIPTION OF THE INVENTION

The novel compounds of the present invention are defined by the general formula (1) below:

Formula 1

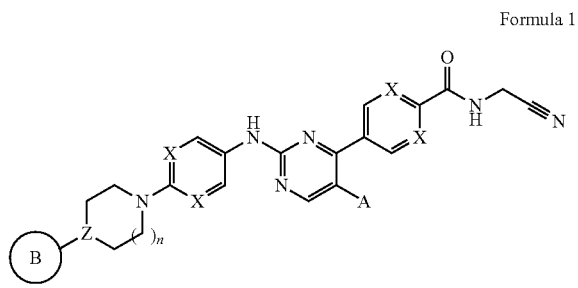

Wherein

X at each occurrence is independently selected from N or CH;

Z at each occurrence is independently selected from N or CH;

'n' is selected from 0, 1.

A is independently selected from hydrogen, halogen, $C_{1-4}$ alkyl, $CF_3$, CN, $CON(R_1)_2$, $OC_{1-4}$alkyl Ring B is selected from following ring systems

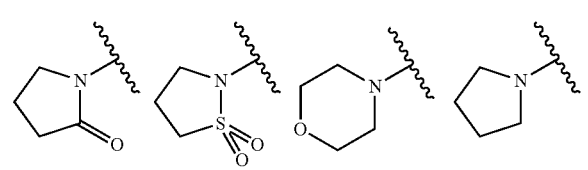

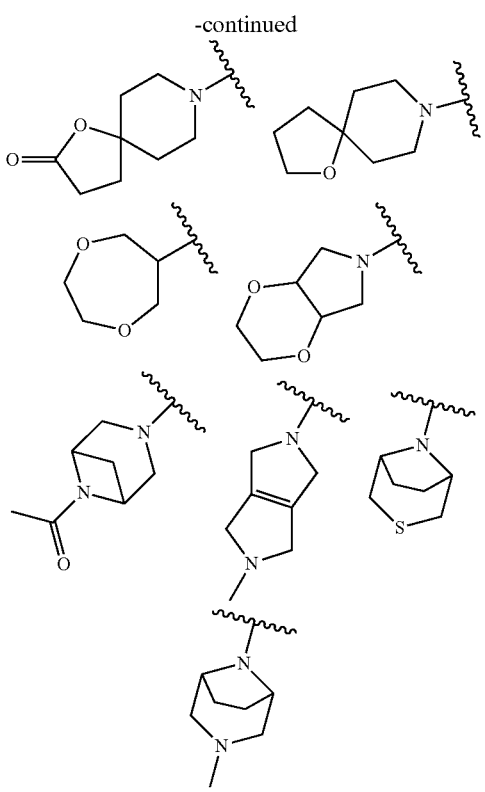

the ring B may, wherever applicable, optionally be substituted with one or more substituents independently selected from the group comprising of OH, CN, $NH_2$, halogen, oxo, $OCF_3$, $CF_3C_1$-$C_6$ alkyl, $OC_1$-$C_6$ alkyl, $(CH_2)_{1-6}OC_1$-$C_6$ alkyl, O—$(CH_2)_{0-4}OC_1$-$C_6$ alkyl, $C(O)NHC_1$-$C_6$ alkyl, $NHC(O)C_1$-$C_6$ alkyl, $S(O)_{0-2}C_1$-$C_6$ alkyl, $(CH_2)_{1-6}N(R_1)_2$, $(CH_2)_{1-6}NHC(=O)OR_1$, $(CH_2)_{1-6}NHC(=O)R_1$, $C(=O)OR_1$, $C(=O)R_1$, $(CH_2)_{1-4}C(=O)$ $NHR_1$, $(CH_2)_{0-4}O(CH_2)_{0-4}Ar_1$, $(CH_2)_{0-4}NH(CH_2)_{0-4}Ar_1$, $(CH_2)_{0-4}$ $Ar_1$, $(CH_2)_{0-4}C(=O)(CH_2)_{0-4}Ar_1$, $(CH_2)_{0-4}C(=O)$ $O(CH_2)_{0-4}Ar_1$, $(CH_2)_{0-4}C(=O)NR_1(CH_2)_{0-4}Ar_1$; The term $Ar_1$ at each occurrence is independently selected from unsubstituted or substituted aryl or heterocyclic ring substituted with one, two, three or four substituents independently selected from the group comprising of OH, CN, $NH_2$, halogen, $OCF_3$, $CF_3$, $C_1$-$C_6$ alkyl, $OC_1$-$C_6$ alkyl, $(CH_2)_{1-6}OC_1$-$C_6$ alkyl, O—$(CH_2)_{0-4}$ $OC_1$-$C_6$ alkyl, $C(O)NHC_1$-$C_6$ alkyl, $NHC(O)C_1$-$C_6$ alkyl, $S(O)_{0-2}C_1$-$C_6$ alkyl, $(CH_2)_{1-6}N(R_1)_2$, $(CH_2)_{1-6}NHC(=O)OR_1$, $(CH_2)_{1-6}NHC(=O)R_1$, $C(=O)OR_1$ or —$C(=O)R_1$, $CH_2(CH_2)_{0-4}C(=O)NHR_1$;

$R_1$ at each occurrence is independently selected from hydrogen, $C_1$-$C_4$ alkyl, $C_1$-$C_4$ haloalkyl, $C_3$-$C_7$ cycloalkyl groups;

Suitable substituents wherever applicable if not specifically defined elsewhere, includes, but are not limited to the following radicals, alone or in combination with other radicals: hydroxyl, oxo, halo, thio, nitro, amino, alkyl, alkoxy, haloalkyl or haloalkoxy groups;

In a further embodiment the groups, radicals described above may be selected from:

the "alkyl" group used either alone or in combination with other radicals, denotes a linear or branched radical containing one to six carbons, selected from methyl, ethyl, n-propyl, iso-propyl, n-butyl, sec-butyl, t-butyl, amyl, t-amyl, n-pentyl, n-hexyl, and the like;

The term "halo" or "halogen" used herein, either alone or in combination with other radicals, such as "haloalkyl", "perhaloalkyl" refers to a fluoro, chloro, bromo or iodo group. The term "haloalkyl" denotes an alkyl radical, as defined above, substituted with one or more halogens; such as fluoromethyl, difluoromethyl, trifluoromethyl, fluoroethyl, difluoroethyl, trifluoroethyl, mono or polyhalo substituted methyl, ethyl, propyl, butyl, pentyl or hexyl groups. The term "haloalkoxy" denotes a haloalkyl, as defined above, directly attached to an oxygen atom, such as fluoromethoxy, chloromethoxy, fluoroethoxy chloroethoxy groups, and the like.

The term "aryl" refers to aromatic mono- and poly-carbocyclic ring systems, wherein the individual carbocyclic rings in the poly ring systems are fused or attached to each other through a single bond. Suitable aryl groups include phenyl, naphthyl, and biphenyl.

The term "substituted," as used herein, means that any one or more hydrogen on the designated atom is replaced with a selection from the indicated group, provided that the designated atom's normal valency is not exceeded, and that the substitution results in a stable compound.

Compounds of formula (I) may contain one or more asymmetric centers and can thus occur as racemates and racemic mixtures, single enantiomers, diastereomeric mixtures and individual diastereomers. The present invention is meant to comprehend all such isomeric forms of the compounds of formula (I), either as single species or mixtures thereof.

Some of the compounds described herein contain olefinic double bonds, and unless specified otherwise, are meant to include both E and Z geometric isomers. Some of the compounds described herein may exist with different points of attachment of hydrogen, referred to as tautomers. Such an example may be a ketone and its enol form known as keto-enol tautomers. The individual tautomers as well as mixture thereof are encompassed with compounds of formula (I).

LIST OF ABBREVIATION

DMF: Dimethyl formamide
DCM: Dichloromethane
EDAC.HCl: N-(3-Dimethyl aminopropyl)-N'-ethyl carbodiimide hydrochloride,
HOBT: 1-Hydroxy benzotriazole
TFA: Trifluoro acetic acid
DCC: Dicyclohexylcarbodiimide
DIPEA: Disopropyl ethyl amine
EtOAc: Ethyl acetate
h: Hour(s)
min: Minute(s)
$t_{Ret}$: Retention time
HCl: Hydrochloric acid
RT: Room temperature [25-30° C.]
BINAP: (±)-2,2'-Bis(diphenylphosphino)-1,1'binapthalene
DPPF: [1,1'-Bis(diphenylphosphino)ferrocene]dichloride palladium complex with DCM
$Pd_2(dba)_3$: Tris(dibenzylideneacetopne)dipalladium
$(PPh_3)_2PdCl_2$: Bis(triphenylphosphine)palladium(II) dichloride
Instrument Details
Mass spectrum was recorded on LC-MS 2010-A Shimadzu. UPLC purity was determined by using Waters Sequipy instrument.

UPLC Column: BEH C18 (2.1×100 mm)1.7μ
Mobile phase: 0.05% TFA in water: ACN gradient.
Flow rate: 1.0 ml/min.
Wave length: UV at 220 nm.
HPLC purity was determined by using Agilent-1100 instrument.
HPLC column J'Sphere ODS 150*4.6 mm,
Flow rate 1.0 ml/min @220 min
NMR spectrum: Bruker Avanc 400 mHz
Particularly useful compounds of the present invention are selected from N-(Cyanomethyl)-4-(2-((4-(4-(2-oxopyrrolidin-1-yl)piperidin-1-yl)phenyl)amino)pyrimidin-4-yl)benzamide;

N-(Cyanomethyl)-4-(2-((4-(4-(1,1-dioxidoisothiazolidin-2-yl) piperidin-1-yl)phenyl)amino)pyrimidin-4-yl)benzamide;

N-(Cyanomethyl)-4-(2-((4-(4-morpholinopiperidin-1-yl)phenyl)amino)pyrimidin-4-yl)benzamide;

4-(2-((4-(4-(1H-1,2,4-Triazol-1-yl)piperidin-1-yl)phenyl)amino)pyrimidin-4-yl)-N-(cyanomethyl)benzamide;

4-(2-((4-(4-(1H-Pyrazol-1-yl)piperidin-1-yl)phenyl)amino)pyrimidin-4-yl)-N-(cyanomethyl)benzamide;

4-(2-((4-([1,3'-Bipyrrolidin]-1'-yl)phenyl)amino)pyrimidin-4-yl)-N-(cyanomethyl)benzamide;

N-(cyanomethyl)-4-(2-((4-(4-(1,1-dioxidotetrahydro-2H-thiopyran-4-yl)piperazin-1-yl)phenyl)amino)pyrimidin-4-yl)benzamide;

N-(Cyanomethyl)-4-(2-((4-(4-(furan-2-yl)piperidin-1-yl)phenyl)amino)pyrimidin-4-yl)benzamide;

N-(Cyanomethyl)-4-(2-((4-(4-(1,1-dioxidotetrahydrothiophen-3-yl)piperazin-1-yl)phenyl)amino)pyrimidin-4-yl)benzamide;

N-(Cyanomethyl)-4-(2-((4-(4-(2,5-dioxopyrrolidin-1-yl)piperidin-1-yl)phenyl)amino)pyrimidin-4-yl)benzamide;

N-(Cyanomethyl)-4-(2-((4-(4-(thiophen-2-yl)piperidin-1-yl)phenyl)amino)pyrimidin-4-yl)benzamide;

N-(Cyanomethyl)-4-(2-((4-(4-(2-oxooxazolidin-3-yl)piperidin-1-yl)phenyl)amino)pyrimidin-4-yl)benzamide;

N-(Cyanomethyl)-4-(2-((4-(4-(tetrahydrofuran-2-yl)piperidin-1-yl)phenyl)amino)pyrimidin-4-yl)benzamide;

N-(Cyanomethyl)-4-(2-((4-(4-(5-methylfuran-2-yl)piperidin-1-yl)phenyl)amino)pyrimidin-4-yl)benzamide;

N-(Cyanomethyl)-4-(2-((4-(4-(tetrahydro-2H-pyran-4-yl)piperazin-1-yl)phenyl)amino)pyrimidin-4-yl)benzamide;

N-(Cyanomethyl)-4-(2-((4-(4-(5-methyltetrahydrofuran-2-yl)piperidin-1-yl)phenyl)amino)pyrimidin-4-yl)benzamide;

4-(2-((4-(4-(6-Oxa-3-azabicyclo[3.1.1]heptan-3-yl)piperidin-1-yl)phenyl)amino)pyrimidin-4-yl)-N-(cyanomethyl)benzamide;

N-(Cyanomethyl)-4-(2-((4-(4-(2-oxoimidazolidin-1-yl)piperidin-1-yl)phenyl)amino)pyrimidin-4-yl)benzamide;

4-(2-((4-(4-(1,3,4-Oxadiazol-2-yl)piperidin-1-yl)phenyl)amino)pyrimidin-4-yl)-N-(cyanomethyl)benzamide;

4-(2-((4-(4-(2H-1,2,3-Triazol-2-yl)piperidin-1-yl)phenyl)amino)pyrimidin-4-yl)-N-(cyano methyl)benzamide;

4-(2-((4-(4-(1H-1,2,3-Triazol-1-yl)piperidin-1-yl)phenyl)amino)pyrimidin-4-yl)-N-(cyano methyl)benzamide;

N-(Cyanomethyl)-4-(2-((4-(4-(5-oxo-1H-1,2,4-triazol-4(5H)-yl) piperidin-1-yl)phenyl)amino)pyrimidin-4-yl)benzamide;

N-(Cyanomethyl)-4-(2-((4-(4-(5-oxo-4,5-dihydro-1H-1,2,4-triazol-1-yl)piperidin-1-yl)phenyl)amino)pyrimidin-4-yl)benzamide;

4-(2-((4-(4-(1-Oxa-8-azaspiro[4.5]decan-8-yl)piperidin-1-yl)phenyl)amino)pyrimidin-4-yl)-N-(cyanomethyl)benzamide;

N-(Cyanomethyl)-4-(2-((4-(4-(5-methyl-1,3,4-oxadiazol-2-yl)piperidin-1-yl)phenyl)amino)pyrimidin-4-yl)benzamide;

N-(Cyanomethyl)-4-(2-((4-(4-(5-methyl-1,3,4-thiadiazol-2-yl)piperidin-1-yl)phenyl)amino)pyrimidin-4-yl)benzamide;

N-(Cyanomethyl)-4-(2-((4-(4-(tetrahydro-2H-[1,4]dioxino[2,3-c]pyrrol-6(3H)-yl)piperidin-1-yl)phenyl)amino)pyrimidin-4-yl)benzamide;

N-(Cyanomethyl)-4-(2-((4-(4-(2-oxo-1-oxa-8-azaspiro[4.5]decan-8-yl)piperidin-1-yl)phenyl)amino)pyrimidin-4-yl)benzamide;

N-(Cyanomethyl)-4-(2-((4-(4-(5-oxo-4,5-dihydro-1,3,4-oxadiazol-2-yl)piperidin-1-yl)phenyl)amino)pyrimidin-4-yl)benzamide;

N-(Cyanomethyl)-4-(2-((4-(4-(4-cyclopropyl-5-methyl-4H-1,2,4-triazol-3-yl) piperidin-1-yl)phenyl)amino)pyrimidin-4-yl)benzamide;

N-(Cyanomethyl)-4-(2-((4-(4-(5-methoxy-1,3,4-oxadiazol-2-yl)piperidin-1-yl)phenyl)amino)pyrimidin-4-yl)benzamide;

4-(2-((4-(4-(1,4-Dioxepan-6-yl)piperazin-1-yl)phenyl)amino)pyrimidin-4-yl)-N-(cyanomethyl)benzamide;

N-(Cyanomethyl)-4-(2-((4-(4-(4,5-dihydro-1H-imidazol-2-yl)piperazin-1-yl)phenyl)amino)pyrimidin-4-yl)benzamide;

N-(Cyanomethyl)-4-(2-((4-(4-(4,5-dihydro-1H-imidazol-2-yl)piperidin-1-yl)phenyl)amino)pyrimidin-4-yl)benzamide;

N-(Cyanomethyl)-4-(2-((4-(3-(tetrahydro-2H-[1,4]dioxino[2,3-c]pyrrol-6(3H)-yl)pyrrolidin-1-yl)phenyl)amino)pyrimidin-4-yl)benzamide;

N-(Cyanomethyl)-4-(2-((4-(4-(5-methyl-1,3,4-oxadiazol-2-yl)piperazin-1-yl)phenyl)amino)pyrimidin-4-yl)benzamide;

N-(Cyanomethyl)-4-(2-((4-(4-(3,4-dihydroxypyrrolidin-1-yl)piperidin-1-yl)phenyl)amino)pyrimidin-4-yl)benzamide;

4-(2-((4-(4-(8-Oxa-3-azabicyclo[3.2.1]octan-3-yl)piperidin-1-yl)phenyl)amino)pyrimidin-4-yl)-N-(cyanomethyl)benzamide;

4-(2-((4-(4-(6-Acetyl-3,6-diazabicyclo[3.1.1]heptan-3-yl)piperidin-1-yl)phenyl)amino)pyrimidin-4-yl)-N-(cyanomethyl)benzamide;

N-(Cyanomethyl)-4-(5-methyl-2-((4-(4-morpholinopiperidin-1-yl)phenyl)amino)pyrimidin-4-yl)benzamide;

N-(Cyanomethyl)-4-(5-methyl-2-((4-(4-(2-oxopyrrolidin-1-yl)piperidin-1-yl)phenyl)amino)pyrimidin-4-yl)benzamide;

4-(2-((4-(4-(1-Oxa-8-azaspiro[4.5]decan-8-yl)piperidin-1-yl)phenyl)amino)-5-methylpyrimidin-4-yl)-N-(cyanomethyl)benzamide;

N-(Cyanomethyl)-4-(5-methyl-2-((4-(4-(5-methyl-1,3,4-oxadiazol-2-yl)piperidin-1-yl)phenyl)amino)pyrimidin-4-yl)benzamide;

N-(Cyanomethyl)-4-(5-fluoro-2-((4-(4-morpholinopiperidin-1-yl)phenyl)amino)pyrimidin-4-yl)benzamide;

4-(5-Chloro-2-((4-(4-morpholinopiperidin-1-yl)phenyl)amino)pyrimidin-4-yl)-N-(cyanomethyl)benzamide;

N-(Cyanomethyl)-4-(5-fluoro-2-((4-(4-(2-oxopyrrolidin-1-yl)piperidin-1-yl)phenyl)amino)pyrimidin-4-yl)benzamide;

4-(5-Chloro-2-((4-(4-(2-oxopyrrolidin-1-yl)piperidin-1-yl)phenyl)amino)pyrimidin-4-yl)-N-(cyanomethyl)benzamide;

4-(2-((4-(4-(6-Oxa-3-azabicyclo[3.1.1]heptan-3-yl)piperidin-1-yl)phenyl)amino)-5-methylpyrimidin-4-yl)-N-(cyanomethyl)benzamide;
4-(2-((4-(4-(6-Oxa-3-azabicyclo[3.1.1]heptan-3-yl)piperidin-1-yl)phenyl)amino)-5-fluoropyrimidin-4-yl)-N-(cyanomethyl)benzamide;
-(2-((4-(4-(6-Oxa 3-azabicyclo[3.1.1]heptan-3-yl)piperidin-1-yl)phenyl)amino)-5-chloropyrimidin-4-yl)-N-(cyanomethyl)benzamide;
N-(Cyanomethyl)-4-(5-methyl-2-((4-(4-(tetrahydro-2H-[1,4]dioxino[2,3-c]pyrrol-6(3H)-yl)piperidin-1-yl)phenyl)amino)pyrimidin-4-yl)benzamide;
N-(Cyanomethyl)-4-(5-fluoro-2-((4-(4-(tetrahydro-2H-[1,4]dioxino[2,3-c]pyrrol-6(3H)-yl)piperidin-1-yl)phenyl)amino)pyrimidin-4-yl)benzamide;
4-(5-Chloro-2-((4-(4-(tetrahydro-2H-[1,4]dioxino[2,3-c]pyrrol-6(3H)-yl)piperidin-1-yl)phenyl)amino)pyrimidin-4-yl)-N-(cyanomethyl)benzamide;
N-(Cyanomethyl)-4-(5-fluoro-2-((4-(4-(5-methyl-1,3,4-oxadiazol-2-yl)piperidin-1-yl)phenyl)amino)pyrimidin-4-yl)benzamide;
4-(5-Chloro-2-((4-(4-(5-methyl-1,3,4-oxadiazol-2-yl)piperidin-1-yl)phenyl)amino)pyrimidin-4-yl)-N-(cyanomethyl)benzamide;
N-(Cyanomethyl)-4-(5-methyl-2-((4-(4-(5-methyl-1,3,4-oxadiazol-2-yl)piperazin-1-yl)phenyl)amino)pyrimidin-4-yl)benzamide;
N-(Cyanomethyl)-4-(5-fluoro-2-((4-(4-(5-methyl-1,3,4-oxadiazol-2-yl)piperazin-1-yl)phenyl)amino)pyrimidin-4-yl)benzamide;
4-(5-Chloro-2-((4-(4-(5-methyl-1,3,4-oxadiazol-2-yl)piperazin-1-yl)phenyl)amino)pyrimidin-4-yl)-N-(cyanomethyl)benzamide;
4-(2-((4-(4-(3-Thia-6-azabicyclo[3.1.1]heptan-6-yl)piperidin-1-yl)phenyl)amino)pyrimidin-4-yl)-N-(cyanomethyl)benzamide;
4-(2-((4-(4-(3-Thia-6-azabicyclo[3.1.1]heptan-6-yl)piperidin-1-yl)phenyl)amino)-5-methylpyrimidin-4-yl)-N-(cyanomethyl)benzamide;
4-(2-((4-(4-(3-Thia-6-azabicyclo[3.1.1]heptan-6-yl)piperidin-1-yl)phenyl)amino)-5-fluoropyrimidin-4-yl)-N-(cyanomethyl)benzamide;
4-(2-((4-(4-(3-Thia-6-azabicyclo[3.1.1]heptan-6-yl)piperidin-1-yl)phenyl)amino)-5-chloropyrimidin-4-yl)-N-(cyanomethyl)benzamide;

The compounds of the present invention may be prepared using the methods described below, together with conventional techniques known to those skilled in the art of organic synthesis, or variations thereon as appreciated by those skilled in the art. Referred methods include, but are not limited to those described below, where all symbols are as defined earlier.

General Procedure 1:

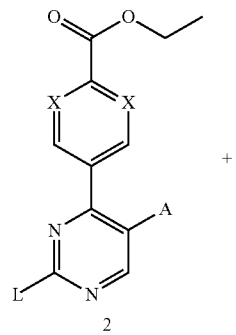

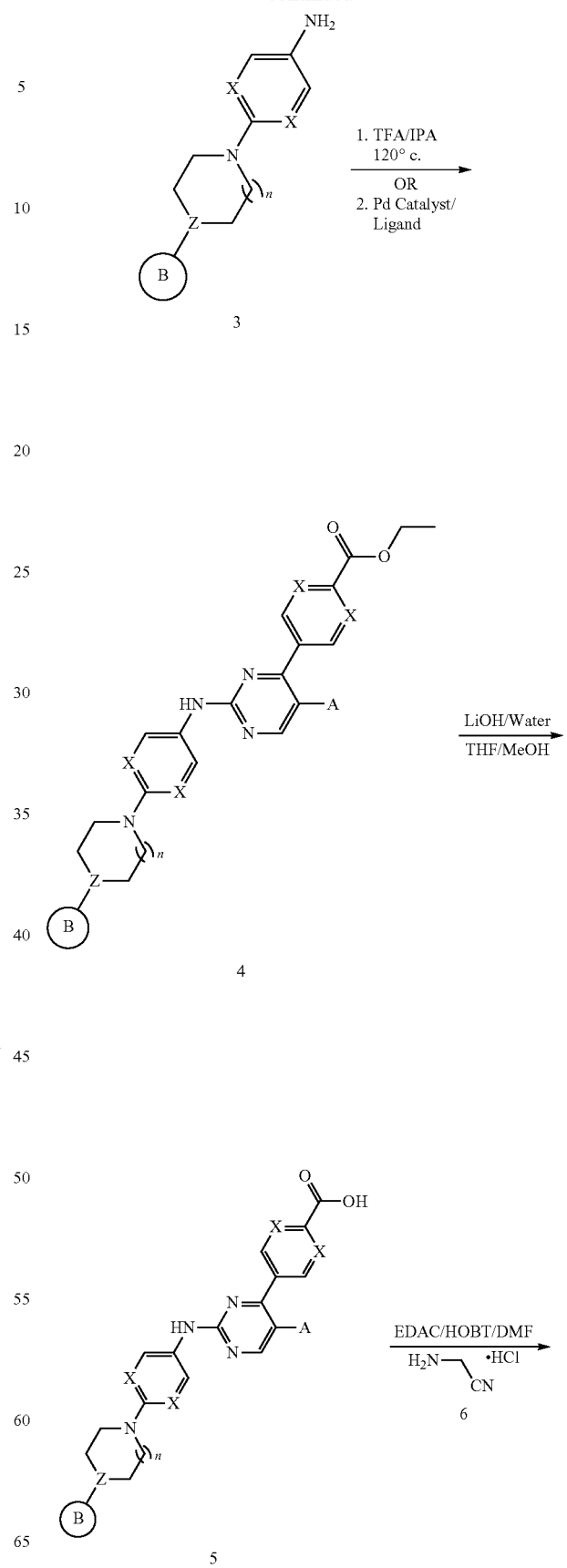

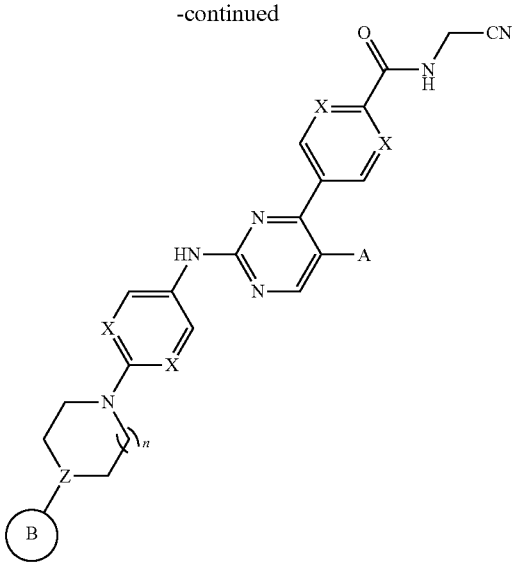

The ester derivative of formula [4] can be synthesized by reacting compound of formula [2], where 'L' is a suitable leaving group selected from Cl, Br, I, or SOCH₃ and the like, and suitable amine derivatives of formula [3] in the presence of an acid such as trifluoro acetic acid, P-toluene sulfonic acid or bases such as potassium carbonate, diisopropyl ethyl amine, tri ethyl amine & the like in solvents such as isopropyl alcohol, dimethyl sulfoxide, dimethyl formamide or dioxane & the like at temperature 25-150° C. Alternative for acid sensitive group attached to amine derivative [3], ester derivative can be prepared by coupling of compound of formula [2] with amine derivative [3] using catalyst like DPPF, Pd$_2$(dba)$_3$, (PPh$_3$)$_2$PdCl$_2$ and like in presence of ligand BINAP and like in solvent DMF, DMA, Dioxane and like at temperature 80-150° C.

Hydrolysis of ester derivative [4] with bases such as sodium hydroxide, lithium hydroxide in solvent(s) such as water, methanol, ethanol, tetrahydrofuran or combination thereof at temperature 25-100° C. afford acid derivative of formula [5]. Acetonitrile derivative of formula [6] may be synthesized by reacting amino acetonitrile [6] with acid derivative of formula [5] using suitable carboxyl groups activating agents such as N-(3-dimethyl aminopropyl)-N'-ethyl carbodiimide hydrochloride (EDAC.HCl), dicyclohexyl carbodiimide and the like in the presence of an additive 1-hydroxy benzotriazole (HOBT) and base like triethyl amine or diisopropylethyl amine (DIEA) & the like in solvent(s) like dimethyl formamide or dichloromethane & the like at temperature 0-25° C.

The compound of formula [2] can be synthesized as per the general procedures known in the art for e.g. as mentioned in WO2008109943 along with suitable variations as are well known to a skilled person. The amine derivative [3], can be synthesized by variety of methods known to those skilled in the art such as following procedures set forth in references such as Fieser and Fieser's Reagents for Organic Synthesis; Wiley & Sons: New York, Volumes 1-21; R. C. LaRock, Comprehensive Organic Transformations, 2.nd edition Wiley-VCH, New York 1999; Comprehensive Organic Synthesis, B. Trost and I. Fleming (Eds.) vol. 1-9 Pergamon, Oxford, 1991; Comprehensive Heterocyclic Chemistry, A. R. Katritzky and C. W. Rees (Eds) Pergamon, Oxford 1984, vol. 1-9; Comprehensive Heterocyclic Chemistry II, A. R. Katritzky and C. W. Rees (Eds) Pergamon, Oxford 1996, vol. 1-11; and Organic Reactions, Wiley & Sons: New York, 1991, Volumes 1-40, to name some of the known literature processes.

The pharmaceutically acceptable salts forming a part of this invention may be prepared by treating the compound of formula (1) with suitable acids in suitable solvents by processes known in the art.

The Ester building block [2] were synthesised by the process described below.

| Ester | Chemical Name |
|---|---|
| Ester 1 | Ethyl 4-(2-chloropyrimidin-4-yl)benzoate |
| Ester 2 | Ethyl 4-(2-chloro-5-methylpyrimidin-4-yl)benzoate |
| Ester 3 | Ethyl 4-(2-chloro-5-fluoropyrimidin-4-yl)benzoate |
| Ester 4 | Ethyl 4-(2-chloro-5-chloropyrimidin-4-yl)benzoate |

Synthesis of Ester Building Block

Ester 1: Preparation of Ethyl 4-(2-chloropyrimidin-4-yl)benzoate

To a solution of 2,4-dichloropyrimidine [70 g, 470 mmol] in DMF [600 mL] was added (PPh$_3$)$_2$PdCl$_2$ [9.9 g, 14 mmol] and mixture was heated to 90° C. for 1 h. To this, (4-(ethoxycarbonyl)phenyl)boronic acid [91 g, 470 mmol] was added and mixture was heated to 90° C. for additional 0.5 h. A solution of potassium bicarbonate [282 g, 2.8 mol] in 200 mL of water was added to reaction mixture and stirred for 0.5 h at 90° C. After completion of reaction, mixture was quanched in ice cooled water [500 mL]. The off white solid obtained was filtered, washed with water and dried under vacuum to get title compound. [45 g, 37%].

Ester 2: Preparation of Ethyl 4-(2-chloro-5-methylpyrimidin-4-yl)benzoate

Prepared similar to the procedure described in Ester 1 but using 2,4-dichloro-5-methylpyrimidine as starting material.

Ester 3: Preparation of Ethyl 4-(2-chloro-5-fluoropyrimidin-4-yl)benzoate

Prepared similar to the procedure described in Ester 1 but using 2,4-dichloro-5-fluoropyrimidine as starting material.

Ester 4: Preparation of Ethyl 4-(2-chloro-5-chloropyrimidin-4-yl)benzoate

Prepared similar to the procedure described in Ester 1 but using 2,4,5-trichloropyrimidine as starting material.

The Amine building blocks [3] were synthesized by the process described below:

| Amine | Chemical Name |
|---|---|
| Amine 1 | 1-(1-(4-Aminophenyl)piperidin-4-yl)pyrrolidin-2-one |
| Amine 2 | 2-(1-(4-Aminophenyl)piperidin-4-yl)isothiazolidine 1,1-dioxide |
| Amine 3 | 4-(4-Morpholinopiperidin-1-yl)aniline |
| Amine 4 | 4-(4-(1H-1,2,4-Triazol-1-yl)piperidin-1-yl)aniline |
| Amine 5 | 4-(4-(1H-Pyrazol-1-yl)piperidin-1-yl)aniline |
| Amine 6 | 4-([1,3'-Bipyrrolidin]-1'-yl)aniline |

-continued

| Amine | Chemical Name |
|---|---|
| Amine 7 | 4-(4-(4-Aminophenyl)piperazin-1-yl)tetrahydro-2H-thiopyran 1,1-dioxide |
| Amine 8 | 4-(4-(Furan-2-yl)piperidin-1-yl)aniline |
| Amine 9 | 3-(4-(4-Aminophenyl)piperazin-1-yl)tetrahydrothiophene 1,1-dioxide |
| Amine 10 | 1-(1-(4-Aminophenyl)piperidin-4-yl)pyrrolidine-2,5-dione |
| Amine 11 | 4-(4-(Thiophen-2-yl)piperidin-1-yl)aniline |
| Amine 12 | 3-(1-(4-Aminophenyl)piperidin-4-yl)oxazolidin-2-one |
| Amine 13 | 4-(4-(Tetrahydrofuran-2-yl)piperidin-1-yl)aniline |
| Amine 14 | 4-(4-(5-Methylfuran-2-yl)piperidin-1-yl)aniline |
| Amine 15 | 4-(4-(Tetrahydro-2H-pyran-4-yl)piperazin-1-yl)aniline |
| Amine 16 | 4-(4-(5-Methyltetrahydrofuran-2-yl)piperidin-1-yl)aniline |
| Amine 17 | 4-(4-(6-Oxa-3-azabicyclo[3.1.1]heptan-3-yl)piperidin-1-yl)aniline |
| Amine 18 | 1-(1-(4-Aminophenyl)piperidin-4-yl)imidazolidin-2-one |
| Amine 19 | 4-(4-(1,3,4-Oxadiazol-2-yl)piperidin-1-yl)aniline |
| Amine 20 | 4-(4-(2H-1,2,3-Triazol-2-yl)piperidin-1-yl)aniline |
| Amine 21 | 4-(4-(1H-1,2,3-Triazol-1-yl)piperidin-1-yl)aniline |
| Amine 22 | 4-(1-(4-Aminophenyl)piperidin-4-yl)-1H-1,2,4-triazol-5(4H)-one |
| Amine 23 | 1-(1-(4-Aminophenyl)piperidin-4-yl)-1H-1,2,4-triazol-5(4H)-one |
| Amine 24 | 4-(4-(1-Oxa-8-azaspiro[4.5]decan-8-yl)piperidin-1-yl)aniline |
| Amine 25 | 4-(4-(5-Methyl-1,3,4-oxadiazol-2-yl)piperidin-1-yl)aniline |
| Amine 26 | 4-(4-(5-methyl-1,3,4-thiadiazol-2-yl)piperidin-1-yl)aniline |
| Amine 27 | 4-(4-(Tetrahydro-2H-[1,4]dioxino[2,3-c]pyrrol-6(3H)-yl)piperidin-1-yl)aniline |
| Amine 28 | 8-(1-(4-Aminophenyl)piperidin-4-yl)-1-oxa-8-azaspiro[4.5]decan-2-one |
| Amine 29 | 5-(1-(4-Aminophenyl)piperidin-4-yl)-1,3,4-oxadiazol-2(3H)-one |
| Amine 30 | 4-(4-(4-Cyclopropyl-5-methyl-4H-1,2,4-triazol-3-yl)piperidin-1-yl)aniline |
| Amine 31 | 4-(4-(5-Methoxy-1,3,4-oxadiazol-2-yl)piperidin-1-yl)aniline |
| Amine 32 | 4-(4-(1,4-Dioxepan-6-yl)piperazin-1-yl)aniline |
| Amine 33 | 4-(4-(4,5-Dihydro-1H-imidazol-2-yl)piperazin-1-yl)aniline |
| Aminr 34 | 4-(4-(4,5-Dihydro-1H-imidazol-2-yl)piperidin-1-yl)aniline |
| Amine 35 | 4-(3-(Tetrahydro-2H-[1,4]dioxino[2,3-c]pyrrol-6(3H)-yl)pyrrolidin-1-yl)aniline |
| Amine 36 | 4-(4-(5-Methyl-1,3,4-oxadiazol-2-yl)piperazin-1-yl)aniline |
| Amine 37 | 1-(1-(4-Aminophenyl)piperidin-4-yl)pyrrolidine-3,4-diol |
| Amine 38 | 4-(4-(3-Oxa-8-azabicyclo[3.2.1]octan-8-yl)piperidin-1-yl)aniline |
| Amine 39 | 1-(3-(1-(4-Aminophenyl)piperidin-4-yl)-3,6-diazabicyclo[3.1.1]heptan-6-yl)ethanone |

Synthesis of Amine Building Block

Amine 1: 1-(1-(4-Aminophenyl)piperidin-4-yl)pyrrolidin-2-one

Step 1: Preparation of 1-(1-(4-nitrophenyl)piperidin-4-yl)pyrrolidin-2-one 1-(piperidin-4-yl)pyrrolidin-2-one (1.8 g, 10.7 mmol) [OPRD 2007, 11, 482-486] was dissolved in DMF (10.0 mL) at rt. To this K$_2$CO$_3$ (2.96 g, 21.40 mmol) was added at rt followed by 1-fluoro-4-nitrobenzene (1.5 mL, 10.7 mmol). The reaction mixture was stirred at 80-90° C. for 4 h. After completion of reaction mixture was quenched in water. Yellow sold obtained was filtered washed with water dried under vacuum to get desired compound (2.5 g, 81%) as yellow solid.

Step 2: Preparation of 1-(1-(4-aminophenyl)piperidin-4-yl)pyrrolidin-2-one

In a 500 mL hydrogenation bottle was added-(1-(4-nitrophenyl)piperidin-4-yl)pyrrolidin-2-one [2.5 g, 8.6 mmol] in ethanol (50 mL). To this 10% Pd/C (0.372 g, 3.50 mmol) was added and bottle was placed on parr hydrogenation apparatus at 50 psi for 8 h. After completion of reaction, mixture was filtered through hyflow bed, washed with methanol and organic volatile was distilled under vacuum to give title amine 1 (1.7 g, 76%) as brown solid.

Amine 2:
2-(1-(4-Aminophenyl)piperidin-4-yl)isothiazolidine 1,1-dioxide

Prepared similar to the procedure described in Amine 1 but using 2-(piperidin-4-yl)isothiazolidine 1,1-dioxide [Ref.: JMC, 53(9), 3517-3531, 2010].

Amine 3: 4-(4-Morpholinopiperidin-1-yl)aniline

Prepared similar to the procedure described in Amine 1 but using 4-(piperidin-4-yl)morpholine [Ref.: BMCL 22(9), 3157-3162, 2012].

Amine 4: 4-(4-(1H-1,2,4-Triazol-1-yl)piperidin-1-yl)aniline

Prepared similar to the procedure described in Amine 1 but using 4-(1H-1,2,4-triazol-1-yl)piperidine [Ref.: WO2008060621].

Amine 5: 4-(4-(1H-Pyrazol-1-yl)piperidin-1-yl)aniline

Prepared similar to the procedure described in Amine 1 but using 4-(1H-pyrazol-1-yl)piperidine [Ref.: WO2013010453].

Amine 6: 4-([1,3'-Bipyrrolidin]-1'-yl)aniline

Prepared similar to the procedure described in Amine 1 but using 1,3'-bipyrrolidine [Ref.: WO2004039780].

Amine 7: 4-(4-(4-Aminophenyl)piperazin-1-yl)tetrahydro-2H-thiopyran 1,1-dioxide

Prepared similar to the procedure described in Amine 1 but using 4-(piperazin-1-yl)tetrahydro-2H-thiopyran 1,1-dioxide [Ref.: WO20070072847].

Amine 8: 4-(4-(Furan-2-yl)piperidin-1-yl)aniline

Prepared similar to the procedure described in Amine 1 but using 4-(furan-2-yl)piperidine [Ref.: WO 9737979].

Amine 9: 3-(4-(4-Aminophenyl)piperazin-1-yl)tetrahydrothiophene 1,1-dioxide

Prepared similar to the procedure described in Amine 1 but using 3-(piperazin-1-yl)tetrahydrothiophene 1,1-dioxide [Ref.: US20080045517].

Amine 10: 1-(1-(4-Aminophenyl)piperidin-4-yl) pyrrolidine-2,5-dione

Prepared similar to the procedure described in Amine 1 but using 1-(piperidin-4-yl)pyrrolidine-2,5-dione.

Amine 11: 4-(4-(Thiophen-2-yl)piperidin-1-yl)aniline

Prepared similar to the procedure described in Amine 1 but using 4-(thiophen-2-yl)piperidine [Ref.: WO 9737979].

Amine 12: 3-(1-(4-Aminophenyl)piperidin-4-yl) oxazolidin-2-one

Prepared similar to the procedure described in Amine 1 but using 3-(piperidin-4yl) oxazolidin-2-one [Ref.: Journal of Medicinal Chemistry, 2008, 51, 144, 4150-69].

Amine 13: 4-(4-(Tetrahydrofuran-2-yl)piperidin-1-yl)aniline

Prepared similar to the procedure described in Amine 1 but using 4-(tetrahydrofuran-2-yl)piperidine [Ref.: WO 9737979].

Amine 14: 4-(4-(5-Methylfuran-2-yl)piperidin-1-yl) aniline

Prepared similar to the procedure described in Amine 1 but using 4-(5-methylfuran-2-yl)piperidine [Ref.: WO 9737979].

Amine 15: 4-(4-(Tetrahydro-2H-pyran-4-yl)piperazin-1-yl)aniline

Prepared similar to the procedure described in Amine 1 but using 1-(tetrahydro-2H-pyran-4-yl)piperazine.

Amine 16: 4-(4-(5-Methyltetrahydrofuran-2-yl)piperidin-1-yl)aniline

Prepared similar to the procedure described in Amine 1 but using 4-(5-methyltetrahydrofuran-2-yl)piperidine [Ref.: WO 9737979].

Amine 17: 4-(4-(6-Oxa-3-azabicyclo[3.1.1]heptan-3-yl)piperidin-1-yl)aniline

Prepared similar to the procedure described in Amine 1 but using 3-(piperidin-4-yl)-6-oxa-3-azabicyclo[3.1.1]heptane [Ref.: Synthesis 2011, 16, 2619-2624].

Amine 18: 1-(1-(4-Aminophenyl)piperidin-4-yl) imidazolidin-2-one

Prepared similar to the procedure described in Amine 1 but using 1-(piperidin-4-yl)imidazolidin-2-one.

Amine 19: 4-(4-(1,3,4-Oxadiazol-2-yl)piperidin-1-yl)aniline

Prepared similar to the procedure described in Amine 1 but using 2-(piperidin-4-yl)-1,3,4-oxadiazole [Ref.: Journal of Med. Chem. 51, 15, 4430-4448, 2008].

Amine 20: 4-(4-(2H-1,2,3-Triazol-2-yl)piperidin-1-yl)aniline

Prepared similar to the procedure described in Amine 1 but using 4-(2H-1,2,3-triazol-2-yl)piperidine [Ref.: Tetrahedron letter 53, 6842-52, 2012].

Amine 21: 4-(4-(1H-1,2,3-Triazol-1-yl)piperidin-1-yl)aniline

Prepared similar to the procedure described in Amine 1 but using 4-(1H-1,2,3-triazol-1-yl)piperidine [Ref.: Tetrahedron letter 53, 6842-52, 2012].

Amine 22: 4-(1-(4-Aminophenyl)piperidin-4-yl)-H-1,2,4-triazol-5(4H)-one

Prepared similar to the procedure described in Amine 1 but using 4-(piperidin-4-yl)-1H-1,2,4-triazol-5(4H)-one [Ref.: WO 2009039257].

Amine 23: 1-(1-(4-Aminophenyl)piperidin-4-yl)-1H-1,2,4-triazol-5(4H)-one

Prepared similar to the procedure described in Amine 1 but using 8-(piperidin-4-yl)-1-oxa-8-azaspiro[4.5]decane [Ref.: BMCL 12, 1759, 2002].

Amine 24: 4-(4-(1-Oxa-8-azaspiro[4.5]decan-8-yl) piperidin-1-yl)aniline

Prepared similar to the procedure described in Amine 1 but using 8-(piperidin-4-yl)-1-oxa-8-azaspiro[4.5]decane [Ref.: BMCL 12, 1759, 2002].

Amine 25: 4-(4-(5-Methyl-1,3,4-oxadiazol-2-yl) piperidin-1-yl)aniline

Prepared similar to the procedure described in Amine 1 but using 2-methyl-5-(piperidin-4-yl)-1,3,4-oxadiazole [Ref.: Journal of Medicinal Chemistry 51, 15, 4430-4448, 2008].

Amine 26: 4-(4-(5-methyl-1,3,4-thiadiazol-2-yl) piperidin-1-yl)aniline

Prepared similar to the procedure described in Amine 1 but using 2-methyl-5-(piperidin-4-yl)-1,3,4-thiadiazole [Ref.: Org. Lett. 2006, 8, 1625-28].

Amine 27: 4-(4-(Tetrahydro-2H-[1,4]dioxino[2,3-c] pyrrol-6(3H)-yl)piperidin-1-yl)aniline Prepared similar to the procedure described in Amine 1 but using 6-(piperidin-4-yl)hexahydro-2H-[1,4]dioxino[2,3-c]pyrrole [Ref.: Synthesis 1995, 795-800].

Amine 28: 8-(1-(4-Aminophenyl)piperidin-4-yl)-1-oxa-8-azaspiro[4.5]decan-2-one Prepared similar to the procedure described in Amine 1 but using 8-(piperidin-4-yl)-1-oxa-8-azaspiro[4.5]decan-2-one [Ref.: WO 0187838, BMCL 12, 1759, 2002].

Amine 29: 5-(1-(4-Aminophenyl)piperidin-4-yl)-1,3,4-oxadiazol-2(3H)-one

Prepared similar to the procedure described in Amine 1 but using 5-(piperidin-4-yl)-1,3,4-oxadiazol-2(3H)-one [Ref.: WO 2013093940].

Amine 30: 4-(4-(4-Cyclopropyl-5-methyl-4H-1,2,4-triazol-3-yl)piperidin-1-yl)aniline Prepared similar to the procedure described in Amine 1 but using 4-(4-cyclopropyl-5-methyl-4H-1,2,4-triazol-3-yl)piperidine [Ref.: BMCL 21,5684-87, 2011].

Amine 31: 4-(4-(5-Methoxy-1,3,4-oxadiazol-2-yl)piperidin-1-yl)aniline

Prepared similar to the procedure described in Amine 1 but using 2-methoxy-5-(piperidin-4-yl)-1,3,4-oxadiazole [Ref.: US 20020111358].

Amine 32: 4-(4-(1,4-Dioxepan-6-yl)piperazin-1-yl)aniline

Prepared similar to the procedure described in Amine 1 but using 1-(1,4-dioxepan-6-yl)piperazine [Ref.: WO 20101139717].

Amine 33: 4-(4-(4,5-Dihydro-1H-imidazol-2-yl)piperazin-1-yl)aniline

Prepared similar to the procedure described in Amine 1 but using 1-(4,5-dihydro-1H-imidazol-2-yl)piperazine [Ref.: WO 2002036562].

Amine 34: 4-(4-(4,5-Dihydro-1H-imidazol-2-yl)piperidin-1-yl)aniline

Prepared similar to the procedure described in Amine 1 but using 4-(4,5-dihydro-1H-imidazol-2-yl)piperidine [Ref.: BMCL 21, 2244-51, 2011].

Amine 35: 4-(3-(Tetrahydro-2H-[1,4]dioxino[2,3-c]pyrrol-6(3H)-yl)pyrrolidin-1-yl)aniline Prepared similar to the procedure described in Amine 1 but using 6-(pyrrolidin-3-yl)hexahydro-2H-[1,4]dioxino[2,3-c]pyrrole [Ref.: Synthesis 795-800, 1995].

Amine 36: 4-(4-(5-Methyl-1,3,4-oxadiazol-2-yl)piperazin-1-yl)aniline

Prepared similar to the procedure described in Amine 1 but using 2-methyl-5-(piperazin-1-yl)-1,3,4-oxadiazole.

Amine 37: 1-(1-(4-Aminophenyl)piperidin-4-yl)pyrrolidine-3,4-diol

Prepared similar to the procedure described in Amine 1 but using 1-(piperidin-4-yl)pyrrolidine-3,4-diol.

Amine 38: 4-(4-(3-Oxa-8-azabicyclo[3.2.1]octan-8-yl)piperidin-1-yl)aniline

Prepared similar to the procedure described in Amine 1 but using 8-(piperidin-4-yl)-3-oxa-8-azabicyclo[3.2.1]octane [Ref.: WO2005108402].

Amine 39: 1-(3-(1-(4-Aminophenyl)piperidin-4-yl)-3,6-diazabicyclo[3.1.1]heptan-6-yl)ethanone Prepared similar to the procedure described in Amine 1 but using 1-(3-(piperidin-4-yl)-3,6-diazabicyclo[3.1.1]heptan-6-yl)ethanone [Ref.: WO2011120854].

The invention is further exemplified by the following examples below, which provides some of the several preferred embodiments of the present invention. These examples are provided merely as representative embodiments and should not be construed to limit the scope of the invention in any way.

Example 1

Preparation of N-(cyanomethyl)-4-(2-((4-(4-(2-oxopyrrolidin-1-yl)piperidin-1-yl)phenyl)amino)pyrimidin-4-yl)benzamide

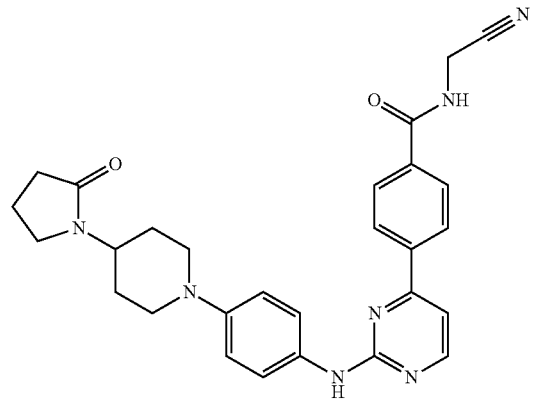 [SMILES: N#CCNC(=O)c1ccc(-c2ccnc(Nc3ccc(N4CCC(N5CCCC5=O)CC4)cc3)n2)cc1]

Step 1: Preparation of ethyl 4-(2-((4-(4-(2-oxopyrrolidin-1-yl)piperidin-1-yl)phenyl)amino)pyrimidin-4-yl)benzoate To a solution of ethyl 4-(2-chloropyrimidin-4-yl)benzoate (7.09 g, 27.0 mmol), in isopropyl alcohol [100 mL] was added 1-(1-(4-aminophenyl)piperidin-4-yl)pyrrolidin-2-one (7.0 g, 27.0 mmol). To this, trifluoro acetic acid (4.62 g, 40.0 mmol) was added and mixture was heated at 120° C. in sealed tube for 16 h. After completion of reaction, mixture was quenched in water, basified with ammonia solution and extracted with ethyl acetate. Organic layer was washed with water, dried over sodium sulfate and removed under reduced pressure to give crude off white solid compound. Purification of crude product was done by the way of column chromatography (SiO$_2$, hexane to 30% EtOAc in hexane) to get solid compound (10.7 g, 82%). The title compound was characterized by spectral analysis. ESI-MS: 486.2 (M+H)$^+$.

Step 2: Preparation of 4-(2-((4-(4-(2-oxopyrrolidin-1-yl)piperidin-1-yl)phenyl)amino)pyrimidin-4-yl)benzoic acid Ethyl 4-(2-((4-(4-(2-oxopyrrolidin-1-yl)piperidin-1-yl)phenyl)amino)pyrimidin-4-yl)benzoate (25.0 g, 51.5 mmol) was dissolved in 3:1 methanol/THF (100 mL). To this lithium hydroxide (9.86 g, 412 mmol) in water (25 mL) was added and mixture was refluxed for 2 h., cooled, concentrated and acidified with dil HCl. The dark precipitate was filtered, washed with water and dried under vacuum to give title compound (20.0 g, 85%). The title compound was characterized by spectral analysis ESI-MS: 458.2 (M+H)*.

Step 3: N-(cyanomethyl)-4-(2-((4-(4-(2-((4-(4(2-oxopyrrolidin-1-yl)piperidin-1-yl)phenyl)amino)pyrimidin-4-yl)benzamide To a solution of 4-(2-((4-(4-(2-oxopyrrolidin-1-yl)piperidin-1-yl)phenyl)amino)pyrimidin-4-yl)benzoic acid [20.0 g, 43.7 mmol] in 200 mL DMF, was added HOBt [8.03 g, 52.5 mmol]. To this reaction mixture, was added EDAC.HCl [10.06 g, 52.5 mmol], 2-aminoacetonitrile hydrochloride [8.09 g, 87 mmol] and triethyl amine [26.5 g, 262 mmol] under N$_2$ at 0-5° C. The resulting reaction mixture was stirred at 25° C. for 16 h. Mixture was diluted with water. The aqueous layer was extracted with EtOAc. The organic layer was washed with brine, dried over sodium sulfate and concentrated in vacuo to afford semi solid compound. Purification of crude product was done by the way of column chromatography (SiO$_2$, CHCl$_3$ to 4% MeOH in CHCl$_3$) to get yellow solid compound (600 mg, 46%). $^1$H NMR (400 MHz, d$_6$-DMSO): 9.47 (s, 1H), 9.33 (1H, t, J=5.8 Hz,), 8.53 (1H, d, J=5.2 Hz), 8.26 (2H, d, J=8.4 Hz), 8.02 (2H, d, J=8.4 Hz), 7.64 (2H, d, J=8.8 Hz), 7.39 (1H, d, J=5.2 Hz), 6.94 (2H, d, J=9.2 Hz), 4.35 (2H, d, J=5.6 Hz), 3.88 (1H, m), 3.68-3.66 (2H, m), 3.44 (2H, m), 2.71-2.66 (2H, m), 2.25-2.13 (2H, m), 1.93-1.89 (2H, m), 1.80-1.76 (2H, m), 1.63-1.61 (2H, m). ESI-MS: (M)$^+$: 496.05. UPLC t$_{ret}$: 2.57 min.

Several compounds of the present invention were prepared following the processes described above along with suitable modifications, alterations etc. as are within the scope of a skilled person.

Example 2

Preparation of N-(cyanomethyl)-4-(2-((4-(4-(1,1-dioxidoisothiazolidin-2-yl) piperidin-1-yl)phenyl)amino)pyrimidin-4-yl)benzamide

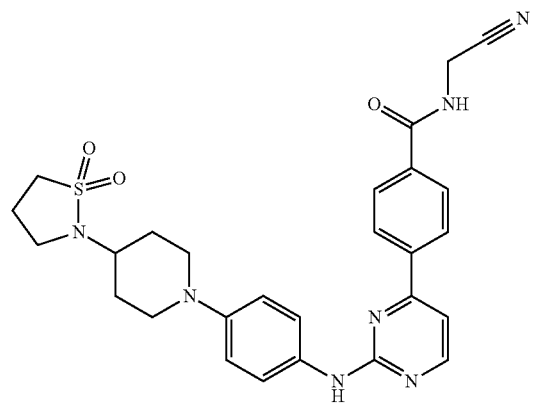 [SMILES: N#CCNC(=O)c1ccc(-c2ccnc(Nc3ccc(N4CCC(N5CCCS5(=O)=O)CC4)cc3)n2)cc1]

Prepared similar to the procedure described in Example 1 but using Ester 1 and Amine 2 as starting materials. The title compound was obtained as yellow solid. $^1$H NMR (400 MHz, d$_6$-DMSO): 9.47 (1H, s), 9.33 (1H, t, J=5.2 Hz), 8.53 (1H, d, J=5.2 Hz), 8.26 (2H, d, J=8.4 Hz), 8.01 (2H, d, J=8.4 Hz), 7.64 (2H, d, J=9.2 Hz), 7.40 (1H, d, J=5.2 Hz), 6.93 (2H, d, J=8.8 Hz), 4.35 (2H, d, J=5.6 Hz), 3.64 (2H, d, J=13.2 Hz), 3.42-3.17 (4H, m), 2.67-2.66 (3H, m), 2.30-2.10 (2H, m), 1.85-1.70 (4H, m). ESI-MS: 531.90 (M+H)$^+$. UPLC t$_{ret}$: 2.73 min.

Example 3

Preparation of N-(cyanomethyl)-4-(2-((4-(4-morpholinopiperidin-1-yl)phenyl)amino)pyrimidin-4-yl)benzamide

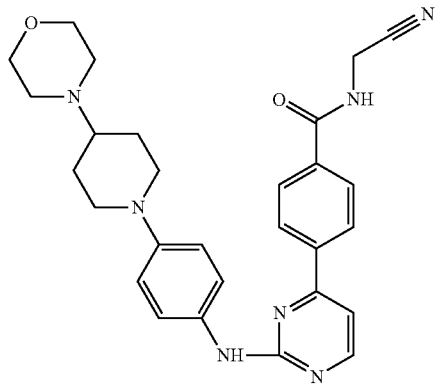 [SMILES: N#CCNC(=O)c1ccc(-c2ccnc(Nc3ccc(N4CCC(N5CCOCC5)CC4)cc3)n2)cc1]

Prepared similar to the procedure described in Example 1 but using Ester 1 and Amine 3 as starting material. The title compound was obtained as yellow solid. $^1$H NMR (400 MHz, d$_6$-DMSO): 9.47 (1H, s), 9.33 (1H, t, J=5.2 Hz), 8.53 (1H, d, J=5.2 Hz), 8.26 (2H, d, J=8.4 Hz), 8.02 (2H, d, J=8.4

Hz), 7.63 (2H, d, J=8.8 Hz), 7.44 (1H, d, J=5.2 Hz), 6.92 (2H, d, J=9.2 Hz), 4.35 (2H, d, J=5.6 Hz), 3.65-3.56 (6H, m), 2.73-2.52 (2H, m), 2.50-2.47 (4H, m), 2.23 (1H, t, J=3.6 Hz), 1.87-1.85 (2H, m), 1.52-1.45 (2H, m). ESI-MS: =514.20 (M+NH$_4$)+. UPLC t$_{ret}$: 2.37 min.

Example 4

Preparation of 4-(2-((4-(4-(1H-1,2,4-triazol-1-yl)piperidin-1-yl)phenyl)amino)pyrimidin-4-yl)-N-(cyanomethyl)benzamide

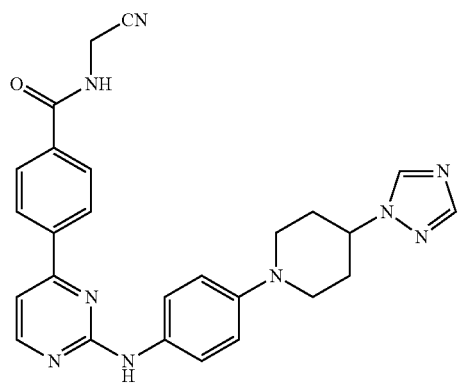 [SMILES: N#CCNC(=O)c1ccc(-c2ccnc(Nc3ccc(N4CCC(n5cncn5)CC4)cc3)n2)cc1]

Prepared similar to the procedure described in Example 1 but using Ester 1 and Amine 4 as starting materials. The title compound was obtained as yellow solid. $^1$H NMR (400 MHz, d$_6$-DMSO): 9.51 (1H, s), 9.35 (1H, t, J=5.2 Hz), 8.61 (1H, s), 8.55 (1H, d, J=5.2 Hz), 8.28 (2H, d, J=8.4 Hz), 8.02 (2H, d, J=8.4 Hz), 7.91 (1H, S), 7.65 (2H, d, J=8.8 Hz), 7.41 (H, d, J=5.2 Hz), 7.0 (2H, d, J=8.8 Hz), 4.4 (1H, m), 4.35 (1H, d, J=5.6 Hz), 3.74-3.71 (2H, m), 2.9-2.8 (2H, m), 2.3-2.1 (4H, m). ESI-MS: 480.20 (M+H)$^+$. UPLC t$_{ret}$: 2.56 min

Example 5

Preparation of 4-(2-((4-(4-(1H-pyrazol-1-yl)piperidin-1-yl)phenyl)amino)pyrimidin-4-yl)-N-(cyanomethyl)benzamide

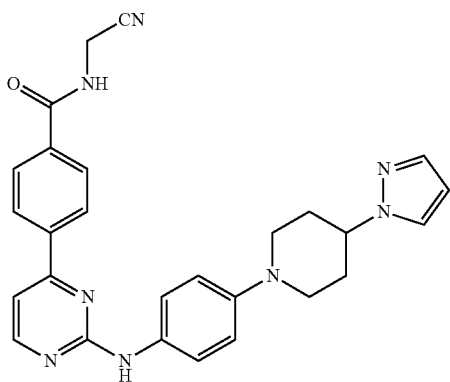 [SMILES: N#CCNC(=O)c1ccc(-c2ccnc(Nc3ccc(N4CCC(n5cccn5)CC4)cc3)n2)cc1]

Prepared similar to the procedure described in Example 1 but using Ester 1 and Amine 5 as starting materials. The title compound was obtained as light yellow solid. $^1$H NMR (400 MHz, d-DMSO): 9.50 (1H, s), 9.34 (1H, t, J=5.2 Hz), 8.54 (1H, d, J=5.2 Hz), 8.27 (2H, d, J=8.4 Hz), 8.02 (2H, d, J=8.4 Hz), 7.81 (1H, d, J=2.0 Hz), 7.66 (2H, d, J=8.8 Hz), 7.45 (1H, d, J=4 Hz), 7.40 (1H, d, J 5.2 Hz), 6.98 (2H, d, J=8.8 Hz), 6.24 (1H, t, J=2 Hz), 4.36-4.33 (3H, m), 3.71-3.74 (2H, m), 2.85-2.78 (2H, m), 2.04-2.10 (4H, m). ESI-MS: 479.35 (M+H)$^+$. UPLC t$_{ret}$: 2.83 min.

Example 6

Preparation of 4-(2-((4-([1,3'-Bipyrrolidin]-1'-yl)phenyl)amino)pyrimidin-4-yl)-N-(cyanomethyl)benzamide

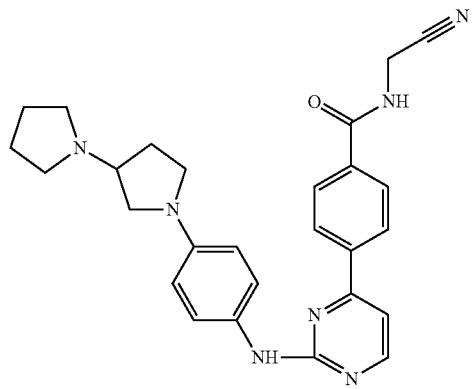 [SMILES: N#CCNC(=O)c1ccc(-c2ccnc(Nc3ccc(N4CCC(N5CCCC5)C4)cc3)n2)cc1]

Prepared similar to the procedure described in Example 1 but using Ester 1 and Amine 6 as starting materials. The title compound was obtained as dark yellow solid. $^1$H NMR (400 MHz, d$_6$-DMSO): 9.32 (2H, t, J=5.2 Hz), 9.30 (1H, s), 8.49 (1H, d, J=5.2 Hz), 8.25 (2H, d, J=8.8 Hz), 8.01 (2H, d, J=8.8 Hz), 7.56 (2H, d, J=8.8 Hz), 7.35 (1H, d, J=5.2 Hz), 6.53 (2H, d, J=9.2 Hz), 4.35 (2H, d, J=5.2 Hz), 3.41-3.43 (1H, m), 3.32-3.26 (2H, m), 3.09-3.05 (1H, m), 2.85-2.81 (1H, m), 2.70-2.69 (4H, m), 2.16-2.14 (1H, m), 1.92-1.85 (1H, m), 1.75-1.70 (4H, m). ESI-MS: 468.12 (M+H)$^+$. UPLC t$_{ret}$: 2.56 min.

Example 7

Preparation of N-(cyanomethyl)-4-(2-((4-(4-(1,1-dioxidotetrahydro-2H-thiopyran-4-yl)piperazin-1-yl)phenyl)amino)pyrimidin-4-yl)benzamide

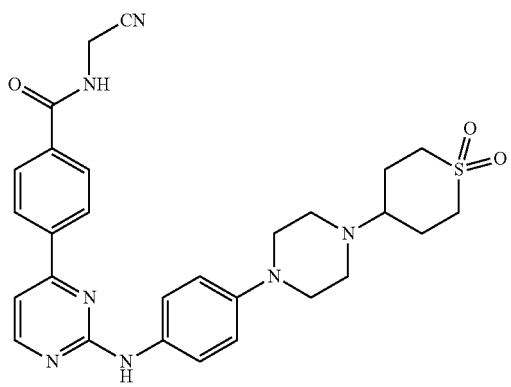 [SMILES: N#CCNC(=O)c1ccc(-c2ccnc(Nc3ccc(N4CCN(C5CCS(=O)(=O)CC5)CC4)cc3)n2)cc1]

Prepared similar to the procedure described in Example 1 but using Ester 1 and Amine 7 as starting material. The title compound was obtained as light yellow solid. $^1$H NMR (400 MHz, d$_6$-DMSO): 9.48 (1H, s), 9.33 (1H, t, J=5.6 Hz), 8.53 (1H, d, J=4.8 Hz), 8.26 (2H, d, J=8.4 Hz), 8.02 (2H, d, J=8.4 Hz), 7.64 (2H, d, J=8.8 Hz), 7.40 (1H, d, J=5.2 Hz), 6.92 (2H, d, J=8.8 Hz), 4.35 (2H, d, J=5.6 Hz), 3.08 (8H, m), 2.67-2.66 (4H, m), 2.04 (4H, m). ESI-MS: 545.95 (M+H)$^+$. UPLC t$_{ret}$: 2.51 min.

Example 8

Preparation of N-(cyanomethyl)-4-(2-((4-(4-(furan-2-yl)piperidin-1-yl)phenyl)amino)pyrimidin-4-yl)benzamide

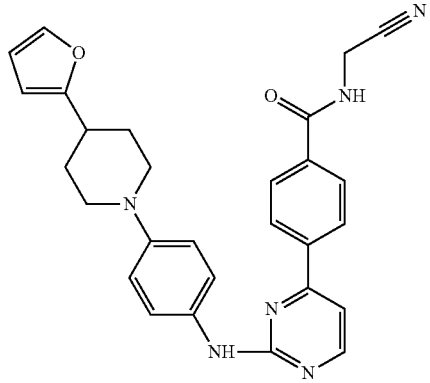 [SMILES: N#CCNC(=O)c1ccc(-c2ccnc(Nc3ccc(N4CCC(c5ccco5)CC4)cc3)n2)cc1]

Prepared similar to the procedure described in Example 1 but using Ester 1 and Amine 8 as starting material. The title compound was obtained as light yellow solid. $^1$H NMR (400 MHz, d$_6$-DMSO): 9.43 (1H, s), 9.33 (1H, t, J=5.6 Hz), 8.53 (1H, d, J=5.2 Hz), 8.02 (2H, d, J=8.4 Hz), 7.65 (2H, d, J=9.2 Hz), 7.53 (1H, t, J=1.6 Hz), 7.39 (1H, d, J=5.2 Hz), 6.95 (2H, d, J=9.2 Hz), 6.38-6.36 (1H, m), 6.13 (1H, d, J=3.2 Hz), 4.35 (2H, d, J=5.6 Hz), 3.65-3.62 (2H, m), 2.78-2.74 (3H, m), 2.10-1.97 (2H, m), 1.82-1.62 (2H, m). ESI-MS: 479.3 (M+H)$^+$. UPLC t$_{ret}$: 3.24 min.

Example 9

Preparation of N-(cyanomethyl)-4-(2-((4-(4-(1,1-dioxidotetrahydrothiophen-3-yl)piperazin-1-yl)phenyl)amino)pyrimidin-4-yl)benzamide

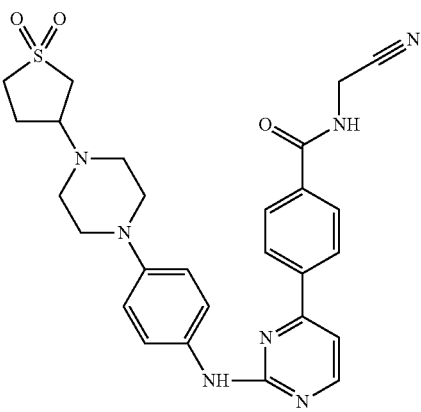 [SMILES: N#CCNC(=O)c1ccc(-c2ccnc(Nc3ccc(N4CCN(C5CCS(=O)(=O)C5)CC4)cc3)n2)cc1]

Prepared similar to the procedure described in Example 1 but using Ester 1 and Amine 9 as starting material. The title compound was obtained as light yellow solid. $^1$H NMR (400 MHz, d$_6$-DMSO): 9.48 (1H, s), 9.33 (1H, t, J=5.6 Hz), 8.53 (1H, d, J=5.2 Hz), 8.26 (2H, d, J=8.8 Hz), 8.02 (2H, d, J=8.8 Hz), 7.65 (2H, d, J=8.8 Hz), 7.39 (1H, d, J=5.2 Hz), 6.92 (2H, d, J=9.2 Hz), 4.32 (2H, d, J=5.6 Hz), 3.40-3.35 (1H, m), 3:28-3.25 (2H, m), 3.12-3.07 (5H, m), 3.04-2.97 (1H, m), 2.68-2.58 (4H, m), 2.36-2.32 (1H, m), 2.02-1.97 (1H, m). ESI-MS: 532.08 (M+H)$^+$. UPLC t$_{ret}$: 2.52 min.

Example 10

Preparation of N-(cyanomethyl)-4-(2-((4-(4-(2,5-dioxopyrrolidin-1-yl)piperidin-1-yl)phenyl)amino)pyrimidin-4-yl)benzamide

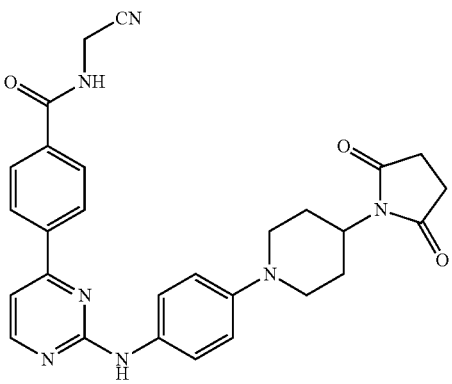 [SMILES: N#CCNC(=O)c1ccc(-c2ccnc(Nc3ccc(N4CCC(N5C(=O)CCC5=O)CC4)cc3)n2)cc1]

Prepared similar to the procedure described in Example 1 but using Ester 1 and Amine 10 as starting material. The title compound was obtained as yellow solid. $^1$H NMR (400 MHz, d$_6$-DMSO): 9.49 (1H, s), 9.34 (1H, t, J=5.6 Hz), 8.53 (1H, d, J=5.2 Hz), 8.26 (2H, d, J=8.8 Hz), 8.02 (2H, d, J=8.8

Hz), 7.63 (2H, d, J=5.2 Hz), 7.40 (1H, d, J=5.2 Hz), 6.93 (2H, d, J=9.2 Hz), 4.35 (2H, d, J=5.6 Hz), 3.99 (1H, m), 3.68 (2H, m), 2.63-2.69 (2H, m), 2.52 (4H, s), 2.32-2.43 (2H, m), 1.56-1.59 (2H, m). ESI-MS: 510.35 (M+H)+.

Example 11

Preparation of N-(cyanomethyl)-4-(2-((4-(4-(thiophen-2-yl)piperidin-1-yl)phenyl)amino)pyrimidin-4-yl)benzamide

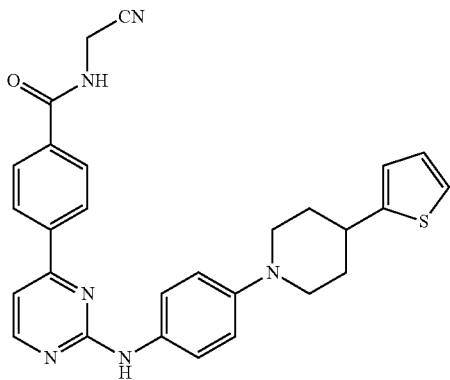 [SMILES: N#CCNC(=O)c1ccc(-c2ccnc(Nc3ccc(N4CCC(c5cccs5)CC4)cc3)n2)cc1]

Prepared similar to the procedure described in Example 1 but using Ester 1 and Amine 11 as starting material. The title compound was obtained as brown solid. $^1$H NMR (400 MHz, $d_6$-DMSO): 9.49 (1H, s), 9.34 (1H, t, J=5.6 Hz), 8.54 (1H, d, J=5.2 Hz), 8.27 (2H, d, J=8.4 Hz), 8.02 (2H, d, J=8.4 Hz), 7.65 (2H, d, J=9.2 Hz), 7.40 (1H, d, J=5.2 Hz), 7.35 (1H, d, J=5.2 Hz), 6.98-6.93 (4H, m), 4.36 (2H, d, J=5.2 Hz), 3.70 (2H, d, J=12.4 Hz), 3.11-2.97 (1H, m), 2.77-2.72 (2H, m), 2.07-2.03 (2H, d, J=12.8 Hz), 1.77-1.73 (2H, m). ESI-MS: 495.25 (M+H)+. UPLC $t_{ret}$: 3.39 min.

Example 12

Preparation of N-(cyanomethyl)-4-(2-((4-(4-(2-oxooxazolidin-3-yl)piperidin-1-yl)phenyl)amino)pyrimidin-4-yl)benzamide

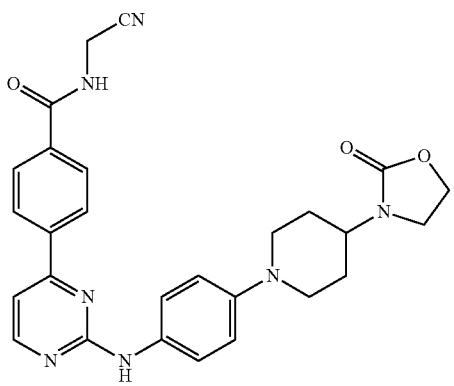 [SMILES: N#CCNC(=O)c1ccc(-c2ccnc(Nc3ccc(N4CCC(N5CCOC5=O)CC4)cc3)n2)cc1]

Prepared similar to the procedure described in Example 1 but using Ester 1 and Amine 12 as starting material. The title compound was obtained as light yellow solid. $^1$H NMR (400 MHz, $d_6$-DMSO): 10.04 (1H, s), 9.41 (1H, t, J=5.2 Hz), 8.64 (1H, d, J=5.2 Hz), 8.28 (2H, d, J=8.8 Hz), 8.03 (2H, d, J=8.4 Hz), 7.65 (2H, d, J=9.2 Hz), 7.40 (1H, d, J=5.2 Hz), 6.96 (2H, d, J=9.2 Hz), 4.35 (2H, d, J=5.2 Hz), 4.26 (2H, t, J=6.8 Hz), 3.71-3.63 (3H, m), 3.53 (2H, t, J=6.8 Hz), 2.73-2.67 (2H, m), 1.80-1.74 (4H, m). ESI-MS: 498.30 (M+H)+. UPLC t: 2.58 min.

Example 13

Preparation of N-(cyanomethyl)-4-(2-((4-(4-(tetrahydrofuran-2-yl)piperidin-1-yl)phenyl)amino)pyrimidin-4-yl)benzamide

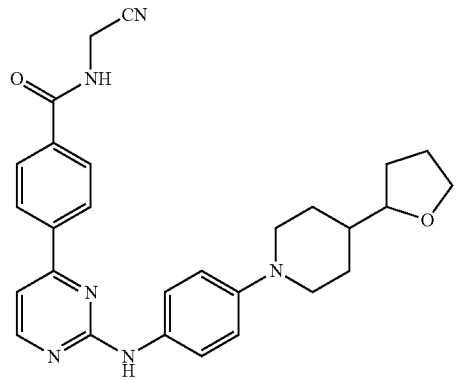 [SMILES: N#CCNC(=O)c1ccc(-c2ccnc(Nc3ccc(N4CCC(C5CCCO5)CC4)cc3)n2)cc1]

Prepared similar to the procedure described in Example 1 but using Ester 1 and Amine 13 as starting material. The title compound was obtained as light yellow solid. $^1$H NMR (400 MHz, $d_6$-DMSO): 9.46 (1H, s), 9.35 (1H, t, J=5.6 Hz), 8.53 (1H, d, J=5.2 Hz), 8.26 (2H, d, J=8.4 Hz), 8.02 (2H, d, J=8.4 Hz), 7.63 (2H, d, J=9.2 Hz), 7.40 (1H, d, J=5.2 Hz), 6.92 (2H, d, J=8.8 Hz), 4.35 (2H, d, J=7.2 Hz), 3.75-3.63 (1H, m), 3.61-3.51 (3H, m), 3.49-3.32 (1H, m), 2.50-2.49 (2H, m), 1.92-1.89 (2H, m), 1.88-1.86 (2H, m), 1.84-1.78 (1H, m), 1.64-1.61 (1H, m), 1.52-1.48 (3H, m). ESI-MS: 483.20 (M+H)+. UPLC $t_{ret}$: 2.88 min.

Example 14

Preparation of N-(cyanomethyl)-4-(2-((4-(4-(5-methylfuran-2-yl)piperidin-1-yl)phenyl)amino)pyrimidin-4-yl)benzamide

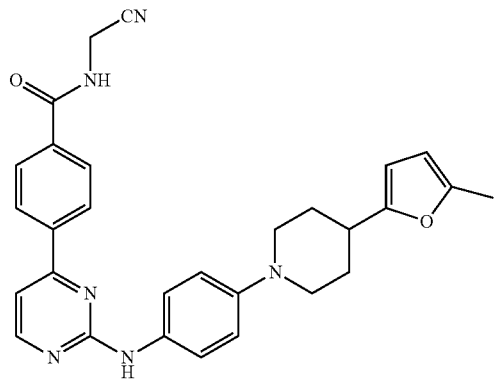 [SMILES: Cc1ccc(C2CCN(c3ccc(Nc4nccc(-c5ccc(C(=O)NCC#N)cc5)n4)cc3)CC2)o1]

Prepared similar to the procedure described in Example 1 but using Ester 1 and Amine 14 as starting material. The title compound was obtained as light yellow solid. $^1$H NMR (400 MHz, d-DMSO): 9.48 (1H, s), 9.34 (1H, t, J=4.8 Hz), 8.54 (1H, d, J=5.2 Hz), 8.27 (2H, d, J=8.4 Hz), 8.03 (2H, d, J=8.4 Hz), 7.64 (2H, d, J=8.8 Hz), 7.40 (1H, d, J=5.2 Hz), 6.95 (2H, d, J=9.2 Hz), 5.96 (2H, t, J=2.8 Hz), 4.36 (2H, d, J=5.6 Hz), 2.67-2.60 (2H, m), 2.76-2.67 (3H, m), 2.33 (3H, s), 2.01-1.98 (2H, m), 1.72-1.65 (2H, m). ESI-MS: 493.20 (M+H)$^+$. UPLC $t_{ret}$: 3.42 min.

Example 15

Preparation of N-(cyanomethyl)-4-(2-((4-(4-(tetrahydro-2H-pyran-4-yl)piperazin-1-yl)phenyl)amino)pyrimidin-4-yl)benzamide

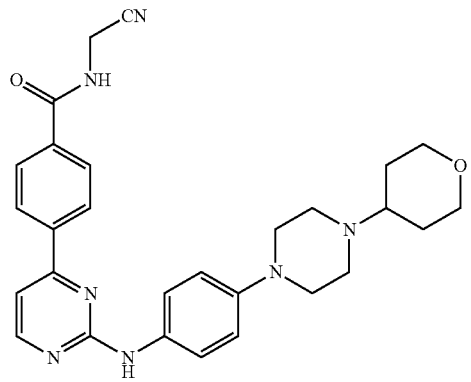 [SMILES: N#CCNC(=O)c1ccc(-c2ccnc(Nc3ccc(N4CCN(C5CCOCC5)CC4)cc3)n2)cc1]

Prepared similar to the procedure described in Example 1 but using Ester 1 and Amine 15 as starting material. The title compound was obtained as light yellow solid. $^1$H NMR (400 MHz, d$_6$-DMSO): 9.46 (s, 1H), 9.33 (1H, t, J=5.6 Hz), 8.52 (1H, d, J=4.8 Hz), 8.25 (2H, d, J=8.4 Hz), 8.01 (2H, d, J=8.4 Hz), 7.63 (2H, d, J=8.8 Hz), 7.39 (1H, d, J=5.2 Hz), 6.92 (2H, d, J=9.2 Hz), 4.34 (2H, d, J=5.6 Hz), 3.88-3.91 (2H, m), 3.29 (2H, m), 3.07 (4H, m), 2.63 (4H, m) 2.49 (1H, m), 1.73 (2H, m), 1.41 (2H, m). ESI-MS: 498.25 (M+H)$^+$. UPLC $t_{ret}$: 2.52 min.

Example 16

Preparation of N-(cyanomethyl)-4-(2-((4-(4-(5-methyltetrahydrofuran-2-yl)piperidin-1-yl)phenyl)amino)pyrimidin-4-yl)benzamide

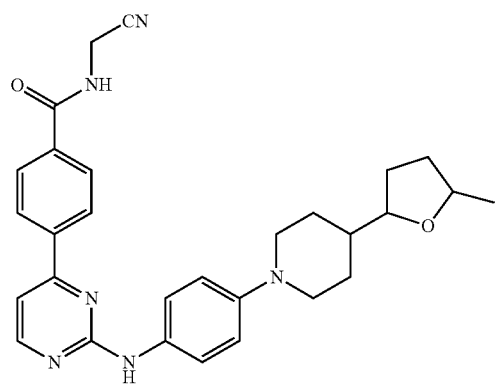 [SMILES: CC1CCC(C2CCN(c3ccc(Nc4nccc(-c5ccc(C(=O)NCC#N)cc5)n4)cc3)CC2)O1]

Prepared similar to the procedure described in Example 1 but using Ester 1 and Amine 16 as starting material. The title compound was obtained as light yellow solid. $^1$H NMR (400 MHz, d$_6$-DMSO): 9.44 (1H, s), 9.32 (1H, bs), 8.51 (1H, d, J=4.8 Hz), 8.24 (2H, d, J=8 Hz), 7.9 (2H, d, J=8.4 Hz), 7.61 (2H, d, J=8.8 Hz), 7.38 (1H, d, J=6 Hz), 6.90 (2H, d, J=8.4 Hz), 4.34 (2H, d, J=5.2 Hz), 3.91-3.82 (1H, m), 3.61-3.58 (2H, m), 3.53-3.51 (1H, m), 1.95-1.75 (4H, m), 1.7-1.62 (2H, m), 1.58-1.27 (4H, m), 1.31-1.11 (3H, m). ESI-MS: 497.20 (M+H)$^+$. UPLC $t_{ret}$: 3.10 min.

Example 17

Preparation of 4-(2-((4-(4-(6-oxa-3-azabicyclo[3.1.1]heptan-3-yl)piperidin-1-yl)phenyl)amino)pyrimidin-4-yl)-N-(cyanomethyl)benzamide

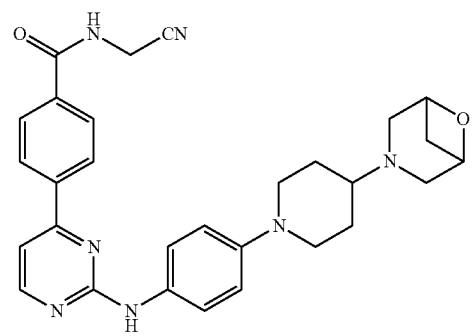 [SMILES: N#CCNC(=O)c1ccc(-c2ccnc(Nc3ccc(N4CCC(N5CC6CC(C5)O6)CC4)cc3)n2)cc1]

Step I: Preparation of ethyl 4-(2-((4-(4-(6-oxa-3-azabicyclo[3.1.1]heptan-3-yl)piperidin-1-yl)phenyl)amino)pyrimidin-4-yl)benzoate Placed ethyl 4-(2-chloropyrimidin-4-yl)benzoate [4.37 g, 16.64 mmol] in rb flask followed by DMA [60 mL]. To this, 4-(4-(6-oxa-3-azabicyclo[3.1.1]heptan-3-yl)piperidin-1-yl) aniline (Amine 17) [3.5 g, 12.80 mmol], cesium carbonate [6.26 g, 19.20 mmol], BINAP [1.19 g, 1.92 mmol] and bis triphenyl phosphite Pd(II)dichloride [1.34 g, 1.92 mmol] was added at 25° C. under $N_2$ atm. The mixture was heated to 90° C. for 16 h. After completion of reaction mixture was quanched in water, compound was extracted with ethyl acetate (50 mL×4). Combined the organic layers and washed with water and brine soln. The organic layer was dried over $Na_2SO_4$, filtered and concentrated under reduced pressure to afford desired product as light yellow solid. Title compound was characterised by spectral analysis. ESI-MS: 500.30 $(M+H)^+$.

Step II: Preparation of 4-(2-((4-(4-(6-oxa-3-azabicyclo[3.1.1]heptan-3-yl)piperidin-1-yl)phenyl)amino)pyrimidin-4-yl)benzoic acid 4-(2-((4-(4-(6-oxa-3-azabicyclo [3.1.1]heptan-3-yl)piperidin-1-yl)phenyl)amino)pyrimidin-4-yl)benzoic acid was prepared by following method as describe in Example 1 Step II using ethyl 4-(2-((4-(4-(6-oxa-3-azabicyclo[3.1.1]heptan-3-yl)piperidin-1-yl)phenyl)amino)pyrimidin-4-yl)benzoate.

Step III. Preparation of 4-(2-((4-(4-(6-oxa-3-azabicyclo[3.1.1]heptan-3-yl)piperidin-1-yl)phenyl)amino)pyrimidin-4-yl)-N-(cyanomethyl)benzamide 4-(2-((4-(4-(6-oxa-3-azabicyclo[3.1.1]heptan-3-yl)piperidin-1-yl)phenyl)amino)pyrimidin-4-yl)-N-(cyanomethyl)benzamide was synthesised by following method as described in Example 1 step II using 4-(2-((4-(4-(6-oxa-3-azabicyclo[3.1.1]heptan-3-yl)piperidin-1-yl)phenyl)amino)pyrimidin-4-yl)benzoic acid. The title compound was obtained as green solid. $^1$H NMR (400 MHz, $d_6$-DMSO): 9.47 (s, 1H), 9.33 (1H, t, J=5.2 Hz), 8.53 (1H, d, J=5.2 Hz), 8.26 (2H, d, J=8.8 Hz), 8.32 (2H, d, J=8.8 Hz), 7.63 (2H, d, J=9.2 Hz), 7.39 (1H, d, J=5.2 Hz), 6.93 (2H, d, J=9.2 Hz), 4.44-4.43 (2H, m), 4.35 (2H, d, J=5.2 Hz), 3.62-3.59 (2H, m), 3.05-3.03 (2H, m), 2.83-2.81 (1H, m), 2.74-2.69 (3H, m), 2.66 (2H, m), 2.32 (1H, m), 1.96-1.93 (2H, m), 1.59-1.56 (2H, m). ESI-MS: 510.15 $(M+H)^+$. UPLC $t_{ret}$: 2.35 min.

Example 18

Preparation of N-(cyanomethyl)-4-(2-((4-(4-(2-oxoimidazolidin-1-yl)piperidin-1-yl)phenyl)amino)pyrimidin-4-yl)benzamide

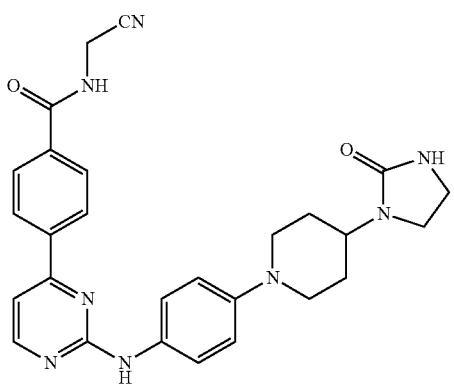 [SMILES: N#CCNC(=O)c1ccc(-c2ccnc(Nc3ccc(N4CCC(N5CCNC5=O)CC4)cc3)n2)cc1]

Prepared similar to the procedure described in Example 17 but using Ester 1 and Amine 18 as starting material. The title compound was obtained as light yellow solid. $^1$H NMR (400 MHz, $d_6$-DMSO): 9.47 (1H, s), 9.43 (1H, bs), 8.53 (1H, d, J=4.8 Hz), 8.26 (2H, d, J=8.0 Hz), 8.02 (2H, d, J=8.0 Hz) 7.64 (2H, d, J=8.8 Hz), 7.40 (1H, d, J=4.8 Hz), 6.94 (2H, d, J=8.4 Hz) 6.26 (1H, s), 4.36 (2H, d, J=4.8 Hz), 3.58-3.68 (3H, m), 3.21-3.23 (2H, m), 2.64-2.70 (2H, m), 1.70-1.78 (2H, m), 1.61-1.64 (2H, m). ESI-MS: 497.40 $(M+H)^+$. UPLC $t_{ret}$: 2.48 min.

Example 19

Preparation of 4-(2-((4-(4-(1,3,4-oxadiazol-2-yl)piperidin-1-yl)phenyl)amino)pyrimidin-4-yl)-N-(cyanomethyl)benzamide

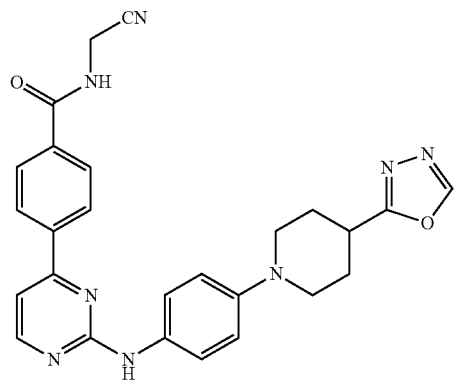 [SMILES: N#CCNC(=O)c1ccc(-c2ccnc(Nc3ccc(N4CCC(c5nnco5)CC4)cc3)n2)cc1]

Prepared similar to the procedure described in Example 1 but using Ester 1 and Amine 19 as starting material. The title compound was obtained as light yellow solid. $^1$H NMR (400 MHz, $d_6$-DMSO): 9.47 (1H, s), 9.34 (1H, t, J=5.2 Hz), 9.16 (1H, s), 8.53 (1H, d, J=5.2 Hz), 8.26 (2H, d, J=8.4 Hz), 8.02 (2H, d, J=8.4 Hz), 7.44 (2H, d, J=8.8 Hz), 7.40 (1H, d, J=5.2 Hz), 6.98 (2H, d, J=5.2 Hz), 4.35 (2H, d, J=5.2 Hz), 3.63-3.60 (2H, s), 3.14-3.19 (1H, m), 2.83-2.80 (2H, m), 2.13-2.19 (2H, m), 1.88-1.85 (2H, m). ESI-MS: 481.05 (M+H)+. UPLC $t_{ret}$: 2.52 min.

Example 20

Preparation of 4-(2-((4-(4-(2H-1,2,3-triazol-2-yl)piperidin-1-yl)phenyl)amino)pyrimidin-4-yl)-N-(cyanomethyl)benzamide

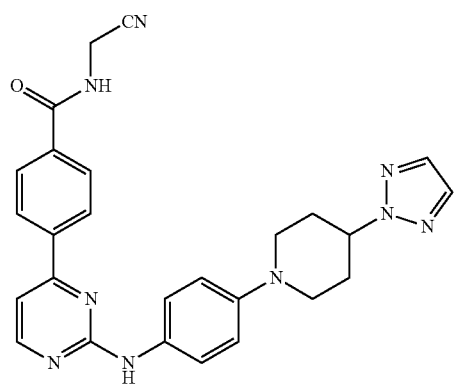 [SMILES: N#CCNC(=O)c1ccc(-c2ccnc(Nc3ccc(N4CCC(n5nccn5)CC4)cc3)n2)cc1]

Prepared similar to the procedure described in Example 17 but using Ester 1 and Amine 20 as starting material. The title compound was obtained as light yellow solid. ¹H NMR (400 MHz, d₆-DMSO): 9.50 (1H, s), 9.34 (1H, t, J=5.6 Hz), 8.55 (1H, d, J=5.2 Hz), 8.28 (2H, d, J=8.4 Hz), 8.03 (2H, d, J=8.8 Hz), 7.80 (2H, s), 7.67 (2H, d, J=9.2 Hz), 7.41 (1H, d, J=5.2 Hz), 7.00 (2H, d, J=9.2 Hz), 4.70 (1H, m), 4.36 (2H, d, J=5.2 Hz), 3.71-3.68 (2H, m), 2.94-2.88 (2H, m), 2.11-2.18 (4H, m). ESI-MS: 479.85 (M+H)+. UPLC $t_{ret}$: 2.85 min.

Example 21

Preparation of 4-(2-((4-(4-(1H-1,2,3-triazol-1-yl) piperidin-1-yl)phenyl)amino)pyrimidin-4-yl)-N-(cyanomethyl)benzamide

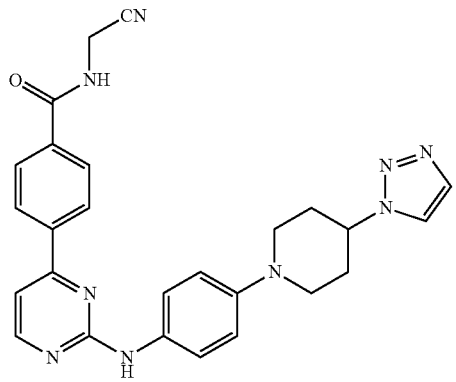 [SMILES: N#CCNC(=O)c1ccc(-c2ccnc(Nc3ccc(N4CCC(n5ccnn5)CC4)cc3)n2)cc1]

Prepared similar to the procedure described in Example 1 but using Ester 1 and Amine 21 as starting material. The title compound was obtained as light yellow solid. ¹H NMR (400 MHz, d₆-DMSO): 9.5 (1H, s), 9.34 (1H, t, J=5.2 Hz), 8.55 (1H, d, J=5.2 Hz), 8.28 (2H, d, J=8.4 Hz), 8.27 (1H, s), 8.03 (2H, d, J=8.8 Hz), 7.80 (1H, s), 7.67 (2H, d, J=9.2 Hz), 7.41 (1H, d, J=5.2 Hz), 7.00 (2H, d, J=9.2 Hz), 4.70-4.67 (1H, m), 4.36 (2H, d, J=5.2 Hz), 3.75-3.72 (2H, m), 2.88-2.94 (2H, m), 2.11-2.18 (4H, m). ESI-MS: 479.85 (M+H)*. UPLC $t_{ret}$: 2.85 min.

Example 22

Preparation of N-(cyanomethyl)-4-(2-((4-(4-(5-oxo-1H-1,2,4-triazol-4(5H)-yl) piperidin-1-yl)phenyl) amino)pyrimidin-4-yl)benzamide

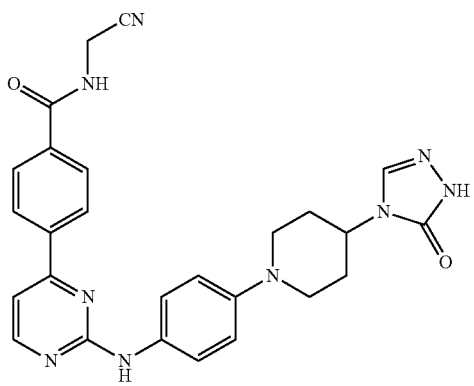 [SMILES: N#CCNC(=O)c1ccc(-c2ccnc(Nc3ccc(N4CCC(n5cn[nH]c5=O)CC4)cc3)n2)cc1]

Prepared similar to the procedure described in Example 1 but using Ester 1 and Amine 22 as starting material. The title compound was obtained as yellow solid. ¹H NMR (400 MHz, d₆-DMSO): 13.28 (1H, s) 9.48 (1H, s), 9.33 (1H, t, J=5.2 Hz), 8.54 (1H, d, J=5.2 Hz), 8.27-8.22 (3H, m) 8.00 (2H, d, J=8.8 Hz), 7.64 (2H, d, J=8.8 Hz), 7.40 (1H, d, J=5.2 Hz), 6.96 (2H, d, J=8.8 Hz), 4.74-4.73 (1H, m), 4.35 (2H, d, J=8.8 Hz), 3.42-3.31 (2H, m), 3.00-2.95 (2H, m), 2.10-2.08 (2H, m), 1.80-1.77 (2H, m). ESI-MS: 518.18 (M+Na)⁺. UPLC $t_{ret}$: 2.49 min Example 23

Preparation of N-(cyanomethyl)-4-(2-((4-(4-(5-oxo-4,5-dihydro-1H-1,2,4-triazol-1-yl)piperidin-1-yl) phenyl)amino)pyrimidin-4-yl)benzamide

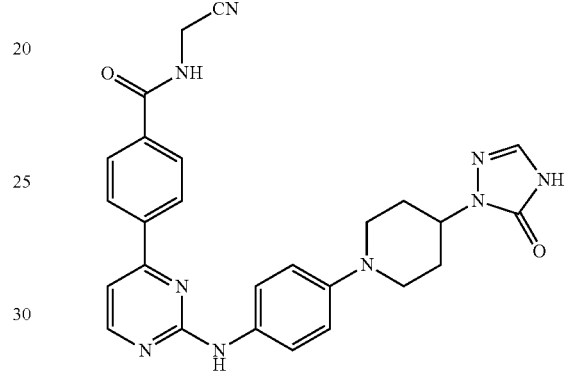

Prepared similar to the procedure described in Example 1 but using Ester 1 and Amine 23 as starting material. The title compound was obtained as light yellow solid. ¹H NMR (400 MHz, d₆-DMSO): 11.65 (1H, s) 9.50 (1H, s), 9.34 (1H, t, J=5.2 Hz), 8.54 (1H, d, J=5.2 Hz), 8.27-8.22 (3H, m) 8.00 (2H, d, J=8.8 Hz), 7.64 (2H, d, J=8.8 Hz), 7.4 (1H, d, J=5.2 Hz), 6.96 (2H, d, J=8.8 Hz), 4.74-4.73 (1H, m), 4.35 (2H, d, J=8.8 Hz), 3.42-3.31 (2H, m), 3.00-2.95 (2H, m), 2.10-2.08 (2H, m), 1.80-1.77 (2H, m). ESI-MS: 518.18 (M+Na)⁺. UPLC $t_{ret}$: 2.49 min.

Example 24

Preparation of 4-(2-((4-(4-(1-oxa-8-azaspiro[4.5] decan-8-yl)piperidin-1-yl)phenyl)amino)pyrimidin-4-yl)-N-(cyanomethyl)benzamide

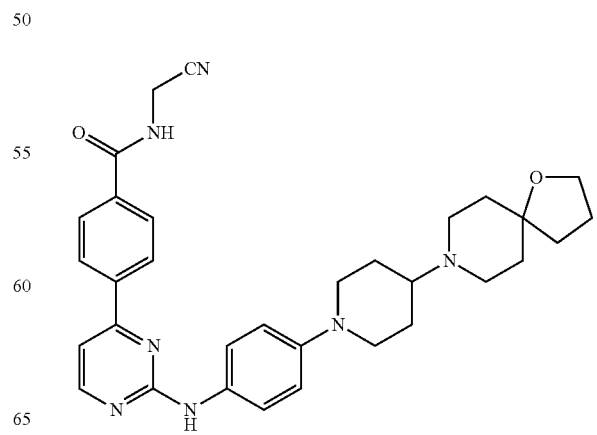

Prepared similar to the procedure described in Example 1 but using Ester 1 and Amine 24 as starting material. The title compound was obtained as light yellow solid. $^1$H NMR (400 MHz, d$_6$-DMSO): 9.44 (1H, s), 9.32 (1H, t, J=5.2 Hz), 8.51 (1H, d, J=5.2 Hz), 8.25 (2H, d, J=8.4 Hz), 7.99 (2H, d, J=8.4 Hz), 7.62 (2H, d, J=8.8 Hz), 7.39 (1H, d, J=5.2 Hz), 6.91 (2H, d, J=8.8 Hz), 4.33 (2H, t, J=5.2 Hz), 3.68-3.65 (4H, m) 2.57-2.48 (6H, m), 1.81-1.79 (4H, m), 1.61-1.59 (3H, m), 1.51-1.49 (6H, m). ESI-MS: 552.20 (M+H)$^+$. UPLC t$_{ret}$: 2.63 min.

Example 25

Preparation of N-(cyanomethyl)-4-(2-((4-(4-(5-methyl-1,3,4-oxadiazol-2-yl)piperidin-1-yl)phenyl)amino)pyrimidin-4-yl)benzamide

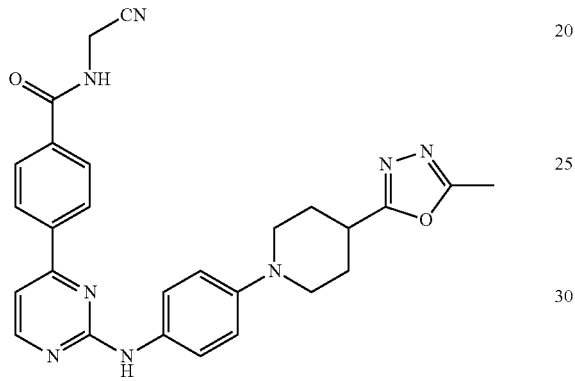

Prepared similar to the procedure described in Example 17 but using Ester 1 and Amine 25 as starting material. The title compound was obtained as light yellow solid. $^1$H NMR (400 MHz, d$_6$-DMSO): 9.48 (s, 1H); 9.33 (1H, t, J=5.2 Hz), 8.53 (1H, d, J=5.2 Hz), 8.26 (2H, d, J=8.0 Hz), 8.00 (2H, d, J=8.4 Hz), 7.65 (2H, d, J=8.8 Hz), 7.40 (1H, d, J=5.2 Hz), 6.95 (2H, d, J=8.8 Hz), 4.35 (2H, d, J=5.6 Hz), 3.63-3.59 (2H, m), 3.09-3.07 (2H, m), 2.85-2.80 (2H, m), 2.49 (2H, s), 2.09-2.06 (2H, m), 1.85-1.82 (2H, m). ESI-MS: 495.25 (M+H)$^+$. UPLC t$_{ret}$: 2.65 min.

Example 26

Preparation of N-(cyanomethyl)-4-(2-((4-(4-(5-methyl-1,3,4-thiadiazol-2-yl)piperidin-1-yl)phenyl)amino)pyrimidin-4-yl)benzamide

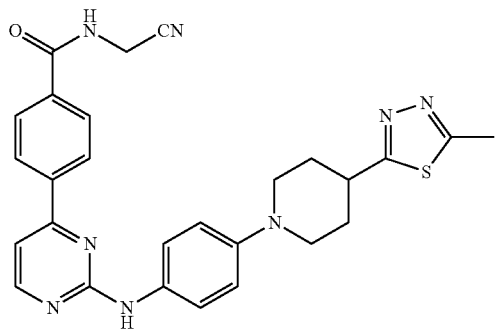 [SMILES: Cc1nnc(C2CCN(c3ccc(Nc4nccc(-c5ccc(C(=O)NCC#N)cc5)n4)cc3)CC2)s1]

Prepared similar to the procedure described in Example 17 but using Ester 1 and Amine 26 as starting material. The title compound was obtained as light yellow solid. $^1$H NMR (400 MHz, d$_6$-DMSO): 9.49 (1H, s), 9.42 (1H, t, J=5.2 Hz), 8.52 (1H, d, J=5.2 Hz), 8.25 (2H, d, J=8.4 Hz), 8.01 (2H, d, J=8.4 Hz), 7.64 (2H, d, J=8.4 Hz), 7.39 (1H, d, J=5.2 Hz), 6.95 (2H, d, J=9.2 Hz), 4.34 (2H, d, J=5.2 Hz), 3.65 (1H, d, J=12.4 Hz), 3.29-3.26 (1H, m), 2.79 (2H, t, J=10 hz), 2.69 (3H, s), 2.14-2.11 (2H, m), 1.85-1.82 (2H, m). ESI-MS: 511.50 (M+H)$^+$. UPLC t$_{ret}$: 2.71 min.

Example 27

Preparation of N-(cyanomethyl)-4-(2-((4-(4-(tetrahydro-2H-[1,4]dioxino[2,3-c]pyrrol-6(3H)-yl)piperidin-1-yl)phenyl)amino)pyrimidin-4-yl)benzamide

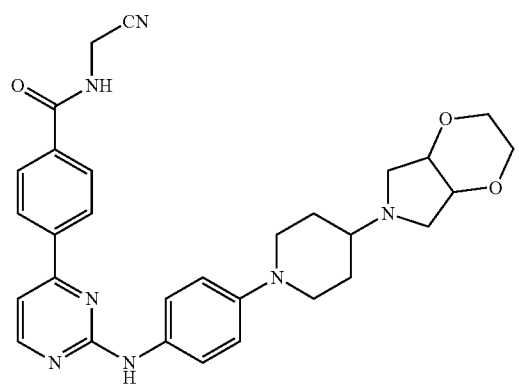 [SMILES: N#CCNC(=O)c1ccc(-c2ccnc(Nc3ccc(N4CCC(N5CC6OCCOC6C5)CC4)cc3)n2)cc1]

Prepared similar to the procedure described in Example 1 but using Ester 1 and Amine 27 as starting material. The title compound was obtained as light yellow solid. $^1$H NMR (400 MHz, d$_6$-DMSO): 9.46 (1H, s), 9.33 (1H, t, J=5.6 Hz), 8.52 (1H, d, J=5.2 Hz), 8.25 (2H, d, J=8.4 Hz), 8.01 (2H, d, J=8.8 Hz), 7.61 (2H, d, J=9.2 Hz), 7.39 (1H, d, J=5.2 Hz), 6.90 (2H, d, J=9.2 Hz), 4.34 (2H, d, J=5.6 Hz), 3.91-3.97 (2H, m), 3.68-2.65 (2H, m), 3.45-2.57 (4H, m), 2.87-2.84 (2H, m), 2.66-2.64 (2H, m), 2.63-2.53 (3H, m), 1.90-1.88 (2H, m), 1.55-1.53 (2H, m). ESI-MS: 540.35 (M+H)$^+$. UPLC t$_{ret}$: 2.46 min.

Example 28

Preparation of N-(cyanomethyl)-4-(2-((4-(4-(2-oxo-1-oxa-8-azaspiro[4.5]decan-8-yl)piperidin-1-yl)phenyl)amino)pyrimidin-4-yl)benzamide

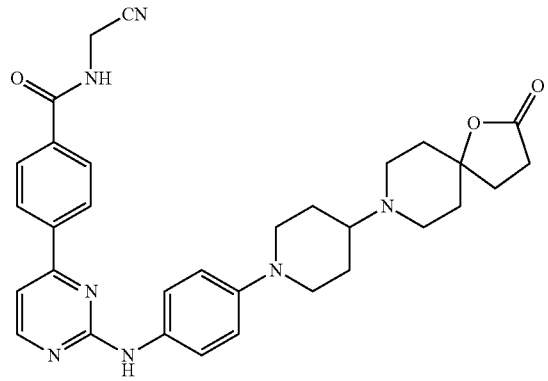 [SMILES: N#CCNC(=O)c1ccc(-c2ccnc(Nc3ccc(N4CCC(N5CCC6(CCC(=O)O6)CC5)CC4)cc3)n2)cc1]

Prepared similar to the procedure described in Example 1 but using Ester 1 and Amine 28 as starting material. The title compound was obtained as light yellow solid. $^1$H NMR (400 MHz, d$_6$-DMSO): 9.46 (1H, s), 9.33 (1H, t, J=5.2 Hz), 8.52 (1H, d, J=5.2 Hz), 8.26 (2H, d, J=8.4 Hz), 8.00 (2H, d, J=8.4 Hz), 7.61 (2H, d, J=9.2), 7.38 (1H, d, J=5.2 Hz), 6.80 (2H, d, J=9.2 Hz), 4.34 (2H, d, J=5.6 Hz), 3.70-3.66 (2H, m), 2.50-2.49 (7H, m), 2.33-2.32 (2H, m), 1.99-1.95 (2H, m), 1.85-1.77 (4H, m), 1.62-1.52 (2H, m), 1.51-1.47 (2H, m). ESI-MS: 566.22 (M+H)$^+$. UPLC t$_{ret}$: 2.50 min.

Example 29

Preparation of N-(cyanomethyl)-4-(2-((4-(4-(5-oxo-4,5-dihydro-1,3,4-oxadiazol-2-yl)piperidin-1-yl)phenyl)amino)pyrimidin-4-yl)benzamide

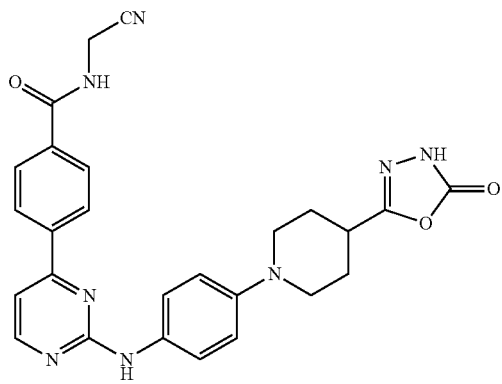 [SMILES: N#CCNC(=O)c1ccc(-c2ccnc(Nc3ccc(N4CCC(c5n[nH]c(=O)o5)CC4)cc3)n2)cc1]

Prepared similar to the procedure described in Example 17 but using Ester 1 and Amine 29 as starting material. The title compound was obtained as light yellow solid. $^1$H NMR (400 MHz, d$_6$-DMSO): 12.10 (1H, s), 9.48 (1H, s), 9.33 (1H, t, J=5.6 Hz), 8.53 (1H, d, J=5.2 Hz), 8.26 (2H, d, J=8.0 Hz), 8.02 (2H, d, J=8.8 Hz), 7.64 (2H, d, J=9.2 Hz), 7.40 (1H, d, J=5.2 Hz), 6.95 (2H, d, J=9.2 Hz), 4.35 (2H, d, J=5.2 Hz), 3.60-3.57 (2H, m), 2.80-2.74 (3H, m), 2.00-1.98 (2H, m), 1.74-1.71 (2H, m). ESI-MS: 497.10 (M+H)$^+$. UPLC t$_{ret}$: 2.67 min.

Example 30

Preparation of N-(cyanomethyl)-4-(2-((4-(4-(4-cyclopropyl-5-methyl-4H-1,2,4-triazol-3-yl) piperidin-1-yl)phenyl)amino)pyrimidin-4-yl)benzamide

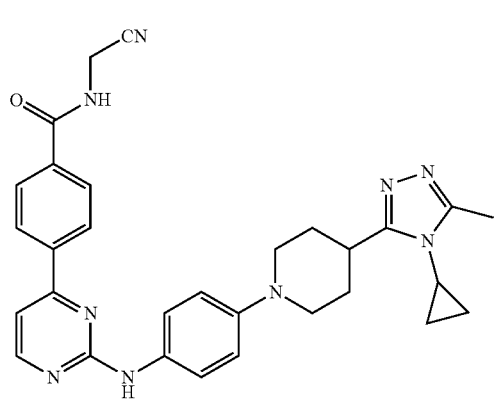 [SMILES: Cc1nnc(C2CCN(c3ccc(Nc4nccc(-c5ccc(C(=O)NCC#N)cc5)n4)cc3)CC2)n1C1CC1]

Prepared similar to the procedure described in Example 1 but using Ester 1 and Amine 30 as starting material. The title compound was obtained as light yellow solid. $^1$H NMR (400 MHz, d$_6$-DMSO): 9.48 (1H, s), 9.33 (1H, t, J=5.2 Hz), 8.53 (1H, d, J=5.2 Hz), 8.26 (2H, d, J=8.4 Hz); 8.02 (2H, d, J=8.8 Hz), 7.65 (2H, d, J=9.2 Hz), 7.40 (1H, d, J=5.2 Hz), 6.97 (2H, d, J=9.2 Hz) 4.35 (2H, d, J=5.6 Hz), 3.72-3.69 (2H, m), 3.17-3.13 (1H, m); 3.00-3.02 (1H, m), 2.77-2.66 (2H, m), 2.33 (3H, s), 2.04-2.01 (2H, m), 1.86-1.84 (2H, m), 1.10-1.09 (2H, m), 1.0-0.98 (2H, m). ESI-MS: 543.30 (M+H)$^+$. UPLC t$_{ret}$: 2.59 min.

Example 31

Preparation of N-(cyanomethyl)-4-(2-((4-(4-(5-methoxy-1,3,4-oxadiazol-2-yl)piperidin-1-yl)phenyl)amino)pyrimidin-4-yl)benzamide

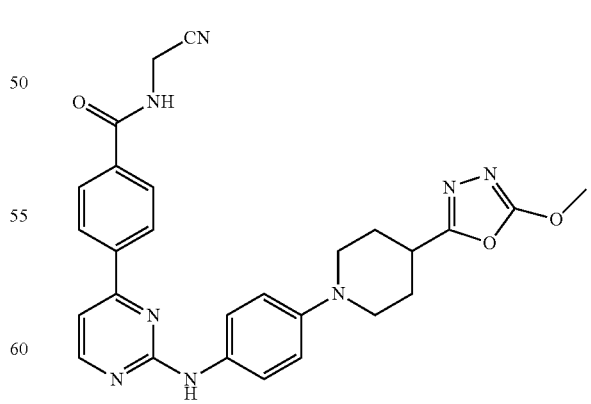

Prepared similar to the procedure described in Example 1 but using Ester 1 and Amine 31 as starting material. The title compound was obtained as light yellow solid. $^1$H NMR (400 MHz, d$_6$-DMSO): 9.48 (1H, s), 9.33 (1H, t, J=5.6 Hz), 8.53

(1H, d, J=5.2 Hz), 8.26 (2H, d, J=8.4 Hz), 8.02 (2H, d, J=8.8 Hz), 7.64 (2H, d, J=8.8 Hz), 7.40 (1H, d, J=5.2 Hz), 6.94 (2H, d, J=9.2 Hz), 4.35 (2H, d, J=5.2 Hz), 3.62-3.58 (2H, m), 3.28 (3H, s), 2.83-2.66 (3H, m) 2.01-1.98 (2H, m) 1.74-1.72 (2H, m). ESI-MS: 511.25 (M+H)+. UPLC $t_{ret}$: 2.83 min.

Example 32

Preparation of 4-(2-((4-(4-(1,4-dioxepan-6-yl)piperazin-1-yl)phenyl)amino)pyrimidin-4-yl)-N-(cyanomethyl)benzamide

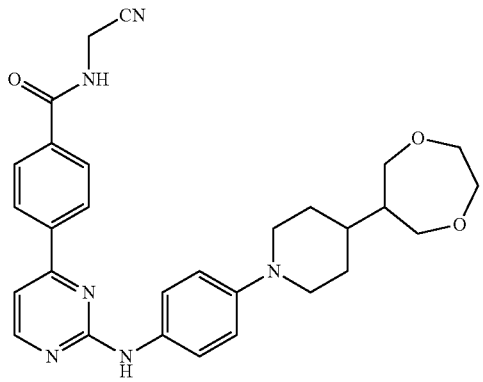 [SMILES: N#CCNC(=O)c1ccc(-c2ccnc(Nc3ccc(N4CCC(C5COCCOC5)CC4)cc3)n2)cc1]

Prepared similar to the procedure described in Example 1 but using Ester 1 and Amine 32 as starting material. The title compound was obtained as light yellow solid. $^1$H NMR (400 MHz, $d_6$-DMSO): 9.47 (1H, s), 9.32 (1H, t, J=5.2 Hz), 8.52 (1H, d, J=5.2 Hz), 8.25 (2H, d, J=8.4 Hz), 8.00 (2H, d, J=8 Hz), 7.62 (2H, d, J=8.8 Hz), 7.38 (1H, d, J=5.2 Hz), 6.90 (2H, d, J=9.2 Hz), 4.34 (2H, d, J=5.2 Hz), 3.82-3.80 (4H, m), 3.56-3.60 (4H, m), 3.02-3.09 (4H, m), 2.71-2.73 (4H, m. ESI-MS: 514.15 (M+H)+. UPLC $t_{ret}$: 2.66 min.

Example 33

Preparation of N-(cyanomethyl)-4-(2-((4-(4-(4,5-dihydro-1H-imidazol-2-yl)piperazin-1-yl)phenyl)amino)pyrimidin-4-yl)benzamide

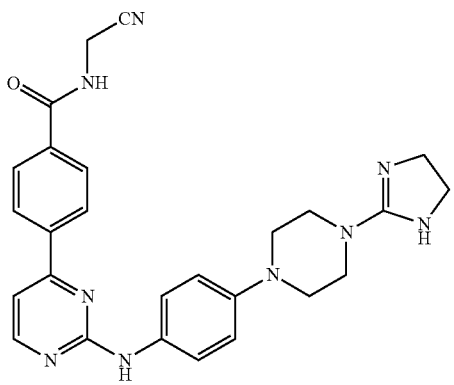 [SMILES: N#CCNC(=O)c1ccc(-c2ccnc(Nc3ccc(N4CCN(C5=NCCN5)CC4)cc3)n2)cc1]

Prepared similar to the procedure described in Example 1 but using Ester 1 and Amine 33 as starting material. The title compound was obtained as light yellow solid. $^1$H NMR (400 MHz, $d_6$-DMSO): 9.52 (1H, s), 9.37 (1H, t, J=4 Hz), 8.54-8.53 (3H, m), 8.26 (2H, d, J=8.4 Hz), 8.02 (2H, d, J=8.4 Hz), 7.68 (2H, d, J=8.8 Hz), 7.41 (1H, d, J=5.2 Hz), 7.09-7.07 (2H, m), 4.34 (2H, d, J=5.6 Hz), 3.66 (4H, s), 3.59-3.57 (4H, m), 3.19-3.15 (4H, m). ESI-MS: 482.05 (M+H)+. UPLC $t_{ret}$: 2.60 min.

Example 34

Preparation of N-(cyanomethyl)-4-(2-((4-(4-(4,5-dihydro-1H-imidazol-2-yl)piperidin-1-yl)phenyl)amino)pyrimidin-4-yl)benzamide

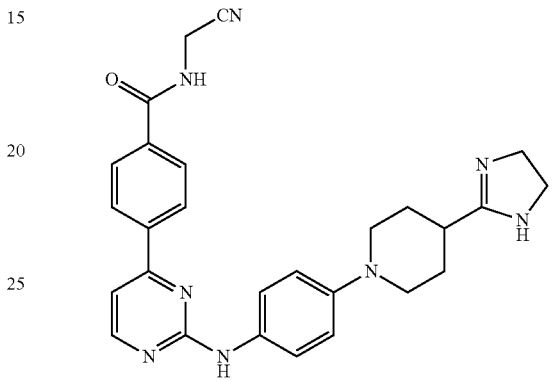

Prepared similar to the procedure described in Example 1 but using Ester 1 and Amine 34 as starting material. The title compound was obtained as light yellow solid. $^1$H NMR (400 MHz, $d_6$-DMSO): 9.48 (1H, s), 9.33 (1H, t, J=5.2 Hz), 8.53 (1H, d, J=5.2 Hz), 8.26 (2H, d, J=8.0 Hz), 8.00 (d, J=8.4 Hz), 7.65 (2H, d, J=8.8 Hz), 7.40 (1H, d, J=5.2 Hz), 6.95 (2H, d, J=8.8 Hz), 4.35 (2H, d, J=5.6 Hz), 4.35 (2H, m), 3.63-3.59 (2H, m), 3.09-3.07 (2H, m), 2.85-2.80 (2H, m), 2.49 (3H, s), 2.09-2.06 (2H, m), 1.85-1.82 (2H, m). ESI-MS: 495.25 (M+H)+. UPLC $t_{ret}$: 2.28 min.

Example 35

Preparation of N-(cyanomethyl)-4-(2-((4-(3-(tetrahydro-2H-[1,4]dioxino[2,3-c]pyrrol-6(3H)-yl)pyrrolidin-1-yl)phenyl)amino)pyrimidin-4-yl)benzamide

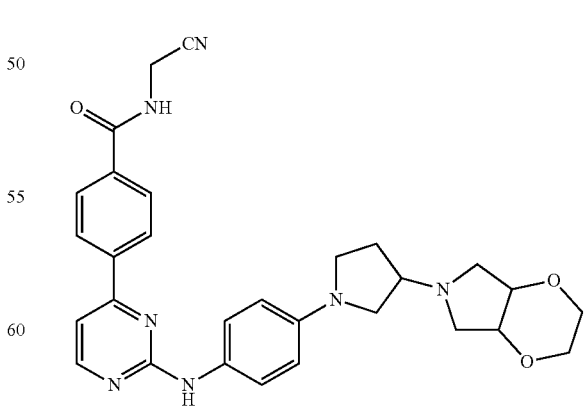

Prepared similar to the procedure described in Example 1 but using Ester 1 and Amine 35 as starting material. The title compound was obtained as light yellow solid. $^1$H NMR (400

MHz, d$_6$-DMSO): 9.33-9.29 (2H, m), 8.48 (1H, d, J=4.8 Hz), 8.25 (1H, d, J=8.4 Hz), 8.05 (2H, d, J=8.8 Hz), 7.55 (2H, d, J=8.8 Hz), 7.34 (1H, d, J=5.2 Hz), 6.51 (2H, d, J=8.8 Hz), 4.34 (2H, d, J=5.2 Hz), 4.01-4.03 (2H, m), 3.71-3.72 (2H, m), 3.62-3.57 (1H, m), 3.45-3.47 (1H, m), 3.22-3.19 (2H, m), 3.01-3.08 (2H, m), 2.94-2.90 (2H, m), 2.86-2.89 (2H, m), 2.09-2.10 (2H, m), 1.82-1.90 (1H, m). ESI-MS: 526.35 (M+H)$^+$. UPLC t$_{ret}$: 2.60 min.

Example 36

Preparation of N-(cyanomethyl)-4-(2-((4-(4-(5-methyl-1,3,4-oxadiazol-2-yl)piperazin-1-yl)phenyl)amino)pyrimidin-4-yl)benzamide

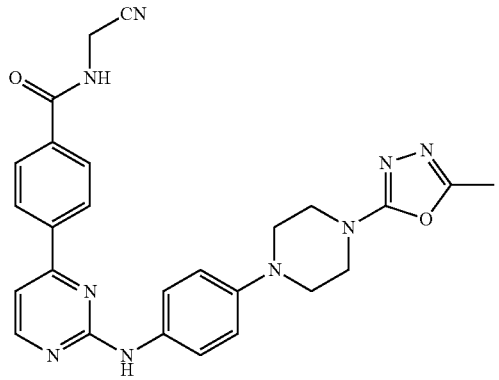 [SMILES: Cc1nnc(N2CCN(c3ccc(Nc4nccc(-c5ccc(C(=O)NCC#N)cc5)n4)cc3)CC2)o1]

Prepared similar to the procedure described in Example 1 but using Ester 1 and Amine 36 as starting material. The title compound was obtained as light yellow solid. $^1$H NMR (400 MHz, d$_6$-DMSO): 9.50 (1H, s), 9.32 (1H, t, J=5.2 Hz), 8.53 (1H, d, J=5.2 Hz), 8.25 (2H, d, J=8.4 Hz), 8.01 (2H, d, J=8.4 Hz), 7.67 (2H, d, J=8.4 Hz), 7.40 (1H, d, J=5.2 Hz), 6.95 (2H, d, J=9.2 Hz), 4.34 (2H, d, J=5.2 Hz), 3.52-3.50 (4H, m), 3.19-1.16 (4H, m), 2.32 (3H, s). ESI-MS: 496.25 (M+H)$^+$. UPLC t$_{ret}$: 2.93 min.

Example 37

Preparation of N-(cyanomethyl)-4-(2-((4-(4-(3,4-dihydroxypyrrolidin-1-yl)piperidin-1-yl)phenyl)amino)pyrimidin-4-yl)benzamide

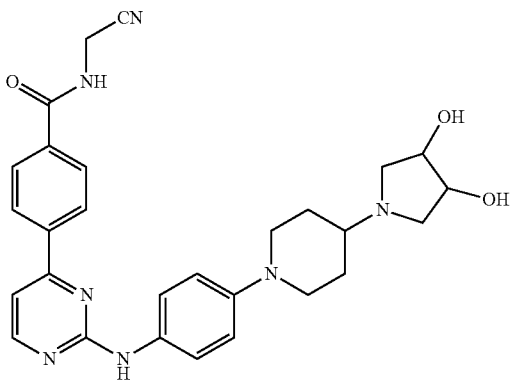 [SMILES: N#CCNC(=O)c1ccc(-c2ccnc(Nc3ccc(N4CCC(N5CC(O)C(O)C5)CC4)cc3)n2)cc1]

Prepared similar to the procedure described in Example 1 but using Ester 1 and Amine 37 as starting material. The title compound was obtained as light yellow solid. $^1$H NMR (400 MHz, d$_6$-DMSO): 9.54 (1H, s), 9.40 (1H, t, J=5.2 Hz), 8.54 (1H, d, J=5.2 Hz), 8.26 (2H, d, J=8.4 Hz), 8.04 (2H, d, J=8.4 Hz), 7.69 (2H, d, J=8 Hz), 7.42 (1H, d, J=5.2 Hz), 7.09-7.07 (2H, m), 4.34 (2H, d, J=5.2 Hz), 4.22-4.01 (2H, m), 3.73-3.65 (6H, m), 2.8-2.69 (2H, m), 2.13-2.11 (2H, m), 1.63 (1H, m), 1.9-1.68 (2H, m), 1.28-1.22 (2H, m). ESI-MS: 514.15 (M+H)$^+$. UPLC t$_{ret}$: 2.34 min.

Example 38

Preparation of 4-(2-((4-(4-(8-oxa-3-azabicyclo[3.2.1]octan-3-yl)piperidin-1-yl)phenyl)amino)pyrimidin-4-yl)-N-(cyanomethyl)benzamide

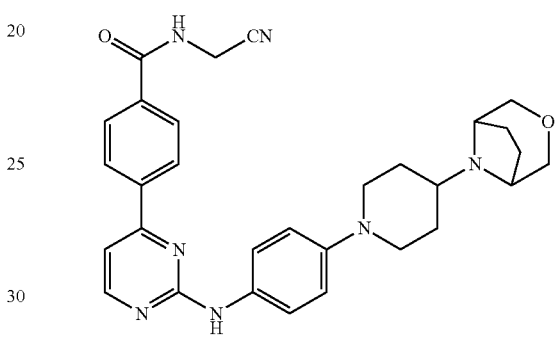

Prepared similar to the procedure described in Example 17 but using Ester 1 and Amine 38 as starting material. The title compound was obtained as light yellow solid. $^1$H NMR (400 MHz, d$_6$-DMSO): 9.48 (1H, s), 9.36 (1H, t, J=5.2 Hz), 8.53 (1H, d, J=5.2 Hz), 8.27 (2H, d, J=8.4 Hz), 8.03 (2H, d, J=8.4 Hz), 7.66 (2H, d, J=8.8 Hz), 7.41 (1H, d, J=4.8 Hz), 6.98 (2H, d, J=9.2 Hz), 4.35 (2H, d, J=5.2 Hz), 4.20 (2H, m), 3.89 (1H, m), 3.80 (2H, m), 3.71 (2H, m), 2.66 (1H, m) 2.03-1.96 (4H, m), 2.01 (3H, m), 1.68 (2H, m). ESI-MS: 524.25 (M+H)$^+$. UPLC t$_{ret}$: 2.48 min.

Example 39

Preparation of 4-(2-((4-(4-(6-acetyl-3,6-diazabicyclo[3.1.1]heptan-3-yl)piperidin-1-yl)phenyl)amino)pyrimidin-4-yl)-N-(cyanomethyl)benzamide

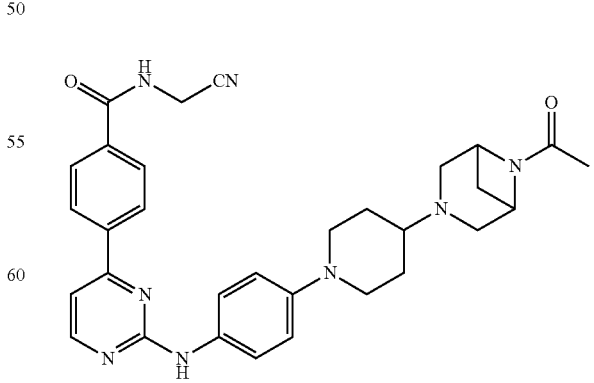

Prepared similar to the procedure described in Example 17 but using Ester 1 and Amine 39 as starting material. The title compound was obtained as light yellow solid. ¹H NMR (400 MHz, d₆-DMSO): 9.44 (s, 1H), 9.32 (t, 1H, J=5.2 Hz), 8.52 (d, 1H, J=5.2 Hz), 8.25 (d, 2H, J=8.4 Hz), 8.01 (d, 2H, J=8.4 Hz), 7.61 (d, 2H, J=9.2 Hz), 7.38 (d, 1H, J=5.2 Hz), 6.90 (d, 2H, J=9.2 Hz), 4.34 (d, 2H, J=5.6 Hz), 3.73-3.76 (m, 1H), 3.61-3.62 (m, 2H), 3.40-3.49 (m, 4H), 3.34-3.38 (m, 1H), 2.69-2.78 (m, 3H), 2.31-2.34 (m, 1H), 2.00 (s, 3H), 1.70-1.80 (m, 2H), 1.22-1.38 (m, 3H). ESI-MS: 551.25 (M+H)⁺. UPLC $t_{ret}$: 2.38 min.

Example 40

Preparation of N-(cyanomethyl)-4-(5-methyl-2-((4-(4-morpholinopiperidin-1-yl)phenyl)amino)pyrimidin-4-yl)benzamide

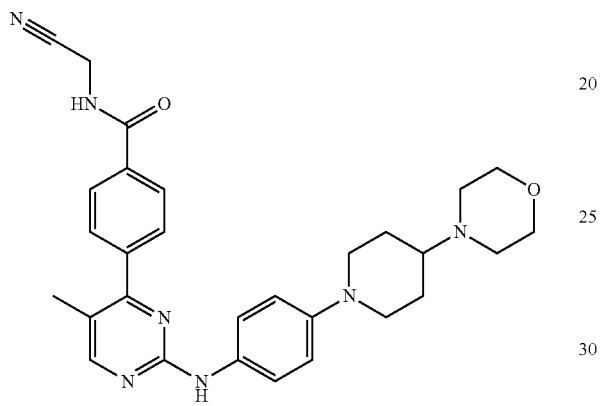

Prepared similar to the procedure described in Example 1 but using Ester 2 and Amine 3 as starting material. The title compound was obtained as light yellow solid. ¹H NMR (400 MHz, d₆-DMSO): 9.30 (t, 2H, J=5.2 Hz), 8.36 (s, 1H), 7.98 (d, 2H, J=8.4 Hz), 7.77 (d, 2H, J=8.0 Hz), 7.57 (d, 2H, J=8.8 Hz), 6.85 (d, 2H, J=8.8 Hz), 4.34 (d, 2H, J=5.6 Hz), 3.57-3.60 (m, 6H), 2.54-2.59 (m, 2H), 2.19 (s, 3H), 1.82-1.85 (m, 2H), 1.47-1.49 (m, 2H), ESI-MS: 512.25 (M+H)⁺. UPLC $t_{ret}$: 2.50 min.

Example 41

Preparation of N-(cyanomethyl)-4-(5-methyl-2-((4-(4-(2-oxopyrrolidin-1-yl)piperidin-1-yl)phenyl)amino)pyrimidin-4-yl)benzamide

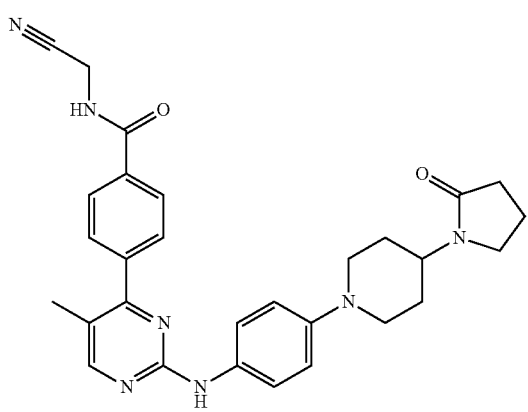 [SMILES: Cc1cnc(Nc2ccc(N3CCC(N4CCCC4=O)CC3)cc2)nc1-c1ccc(C(=O)NCC#N)cc1]

Prepared similar to the procedure described in Example 1 but using Ester 2 and Amine 1 as starting material. The title compound was obtained as light yellow solid. ¹H NMR (400 MHz, d₆-DMSO): 9.32 (bs, 2H), 8.38 (bs, 1H), 7.99 (d, 2H, J=7.6 Hz), 7.77 (d, 2H, J=8.0 Hz), 7.59 (d, 2H, J=7.6 Hz), 6.88 (d, 2H, J=8.8 Hz), 4.34 (d, 2H, J=4.8 Hz), 3.85 (m, 1H), 3.61-3.63 (m, 2H), 2.61-2.65 (m, 2H), 2.22-2.24 (m, 3H), 2.19 (s, 3H), 1.88-1.92 (m, 3H), 1.72-1.81 (m, 2H), 1.61-1.67 (m, 2H). ESI-MS: 510.20 (M+H)⁺. UPLC $t_{ret}$: 2.71 min.

Example 42

Preparation of 4-(2-((4-(4-(1-oxa-8-azaspiro[4.5]decan-8-yl)piperidin-1-yl)phenyl)amino)-5-methylpyrimidin-4-yl)-N-(cyanomethyl)benzamide

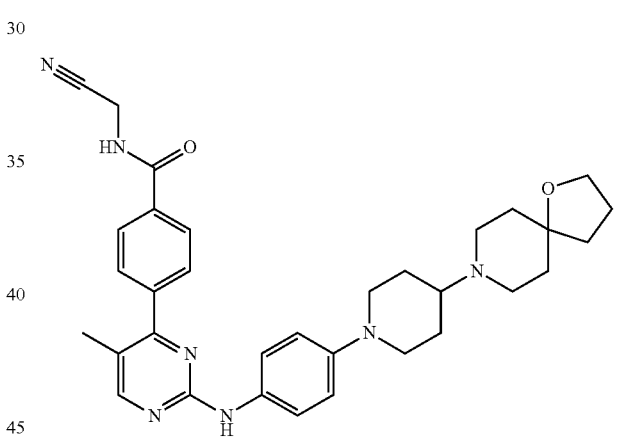

Prepared similar to the procedure described in Example 1 but using Ester 2 and Amine 24 as starting material. The title compound was obtained as light yellow solid. ¹H NMR (400 MHz, d₆-DMSO): 9.43 (1H, s), 9.30 (1H, t, J=5.6 Hz), 8.37 (1H, s), 8.00 (2H, d, J=8.4 Hz), 7.77 (2H, d, J=8.4 Hz), 7.60 (2H, d, J=9.2 Hz), 6.89 (2H, d, J=9.2 Hz), 4.35 (2H, d, J=5.6 Hz), 3.77-3.70 (4H, m), 3.42-3.40 (2H, m), 3.06-3.03 (2H, m), 2.66-2.59 (2H, m), 2.18 (3H, s), 2.11-2.08 (2H, m), 1.91-1.85 (2H, m), 1.80-1.69 (6H, m). ESI-MS: 566.22 (M+H)⁺. UPLC $t_{ret}$: 2.80 min.

Example 43

Preparation of N-(cyanomethyl)-4-(5-methyl-2-((4-(4-(5-methyl-1,3,4-oxadiazol-2-yl)piperidin-1-yl)phenyl)amino)pyrimidin-4-yl)benzamide

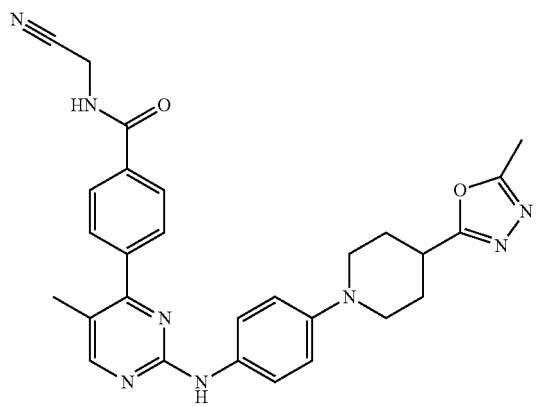 [SMILES: Cc1nnc(C2CCN(c3ccc(Nc4ncc(C)c(-c5ccc(C(=O)NCC#N)cc5)n4)cc3)CC2)o1]

Prepared similar to the procedure described in Example 17 but using Ester 2 and Amine 25 as starting material. The title compound was obtained as light yellow solid. $^1$H NMR (400 MHz, d$_6$-DMSO): 9.30-9.32 (m, 2H), 8.37 (s, 1H), 7.99 (d, 2H, J=8.4 Hz), 7.77 (d, 2H, J=8.4 Hz), 7.60 (d, 2H, J=8.8 Hz), 6.89 (d, 2H, J=9.2 Hz), 4.34 (d, 2H, J=5.2 Hz), 3.55-3.58 (m, 2H), 3.06 (m, 1H), 2.75-2.82 (m, 2H), 2.46 (s, 3H), 2.19 (s, 3H), 2.03-2.07 (m, 2H), 1.80-1.83 (m, 2H). ESI-MS: 509.10 (M+H)$^+$. UPLC t$_{ret}$: 2.86 min.

Example 44

Preparation of N-(cyanomethyl)-4-(5-fluoro-2-((4-(4-morpholinopiperidin-1-yl)phenyl)amino)pyrimidin-4-yl)benzamide

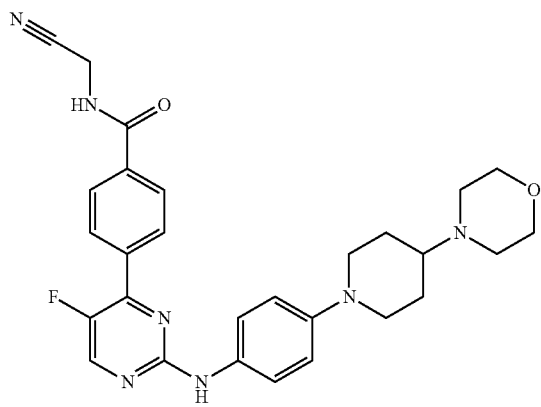 [SMILES: N#CCNC(=O)c1ccc(-c2nc(Nc3ccc(N4CCC(N5CCOCC5)CC4)cc3)ncc2F)cc1]

Prepared similar to the procedure described in Example 1 but using Ester 3 and Amine 3 as starting material. The title compound was obtained as light yellow solid. $^1$H NMR (400 MHz, d$_6$-DMSO): 9.30 (t, 2H, J-5.2 Hz), 8.36 (s, 1H), 7.98 (d, 2H, J=8.4 Hz), 7.77 (d, 2H, J=8.0 Hz), 7.57 (d, 2H, J=8.8 Hz), 6.85 (d, 2H, J=8.8 Hz), 4.34 (d, 2H, J=5.6 Hz), 3.57-3.60 (m, 6H), 2.54-2.59 (m, 2H), 2.19 (s, 3H), 1.82-1.85 (m, 2H), 1.47-1.49 (m, 2H). ESI-MS: 512.25 (M+H)$^+$. UPLC t$_{ret}$: 2.50 min.

Example 45

Preparation of 4-(5-chloro-2-((4-(4-morpholinopiperidin-1-yl)phenyl)amino)pyrimidin-4-yl)-N-(cyanomethyl)benzamide

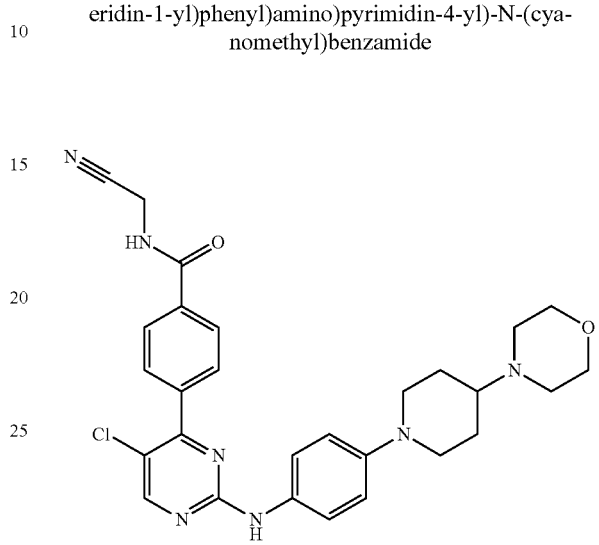

Prepared similar to the procedure described in Example 1 but using Ester 4 and Amine 3 as starting material. The title compound was obtained as light yellow solid. $^1$H NMR (400 MHz, d$_6$-DMSO): 9.70 (s, 1H), 9.33 (t, 1H, J=5.6 Hz), 8.57 (s, 1H), 8.00 (d, 2H, J=8.4 Hz), 7.90 (d, 2H, J=8.4 Hz), 7.53 (d, 2H, J=8.8 Hz), 6.88 (d, 2H, J=9.2 Hz), 4.35 (d, 2H, J=5.6 Hz), 3.53-3.63 (m, 6H), 2.56-2.62 (m, 2H), 2.49-2.50 (m, 4H), 2.10-2.23 (m, 1H), 1.83-1.86 (m, 2H), 1.47-1.49 (m, 2H). ESI-MS: 532.20 (M+H)$^+$. UPLC t$_{ret}$: 2.75 min.

The following compounds can be synthesized following the same procedure as described above and are considered to be encompassed within the scope of the present invention.

N-(Cyanomethyl)-4-(5-fluoro-2-((4-(4-(2-oxopyrrolidin-1-yl)piperidin-1-yl)phenyl)amino)pyrimidin-4-yl)benzamide

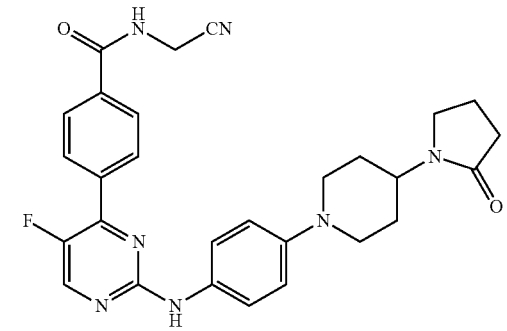 [SMILES: N#CCNC(=O)c1ccc(-c2nc(Nc3ccc(N4CCC(N5CCCC5=O)CC4)cc3)ncc2F)cc1]

49

4-(5-Chloro-2-((4-(4-(2-oxopyrrolidin-1-yl)piperidin-1-yl)phenyl)amino)pyrimidin-4-yl)-N-(cyanomethyl)benzamide

50

4-(2-((4-(4-(6-Oxa-3-azabicyclo[3.1.1]heptan-3-yl)piperidin-1-yl)phenyl)amino)-5-chloropyrimidin-4-yl)-N-(cyanomethyl)benzamide

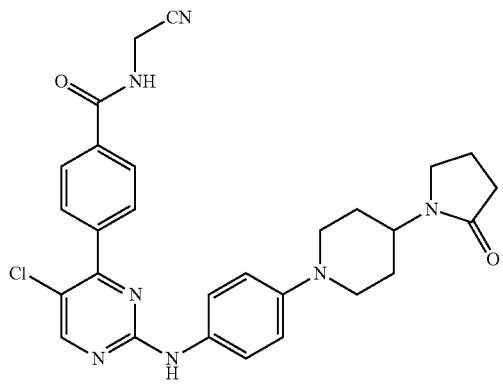 [SMILES: N#CCNC(=O)c1ccc(-c2nc(Nc3ccc(N4CCC(N5CCCC5=O)CC4)cc3)ncc2Cl)cc1]

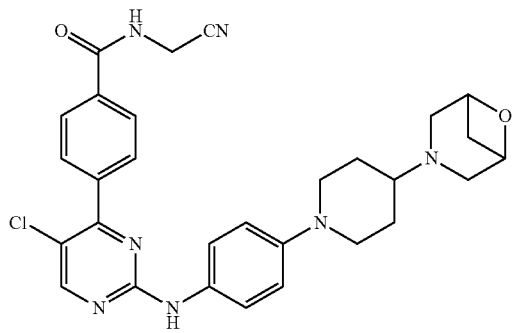

4-(2-((4-(4-(6-Oxa-3-azabicyclo[3.1.1]heptan-3-yl)piperidin-1-yl)phenyl)amino)-5-methylpyrimidin-4-yl)-N-(cyanomethyl)benzamide N-(Cyanomethyl)-4-(5-fluoro-2-((4-(4-(tetrahydro-2H-[1,4]dioxino[2,3-c]pyrrol-6(3H)-yl)piperidin-1-yl)phenyl)amino)pyrimidin-4-yl)benzamide

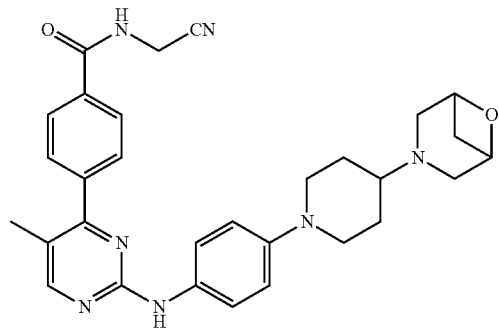 [SMILES: Cc1cnc(Nc2ccc(N3CCC(N4CC5CC(C4)O5)CC3)cc2)nc1-c1ccc(C(=O)NCC#N)cc1]

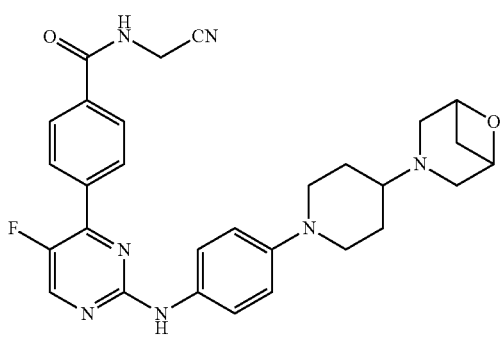 [SMILES: N#CCNC(=O)c1ccc(-c2nc(Nc3ccc(N4CCC(N5CC6CC(C5)O6)CC4)cc3)ncc2F)cc1]

4-(2-((4-(4-(6-Oxa-3-azabicyclo[3.1.1]heptan-3-yl)piperidin-1-yl)phenyl)amino)-5-fluoropyrimidin-4-yl)-N-(cyanomethyl)benzamide N-(Cyanomethyl)-4-(5-methyl-2-((4-(4-(tetrahydro-2H-[1,4]dioxino[2,3-c]pyrrol-6(3H)-yl)piperidin-1-yl)phenyl)amino)pyrimidin-4-yl)benzamide

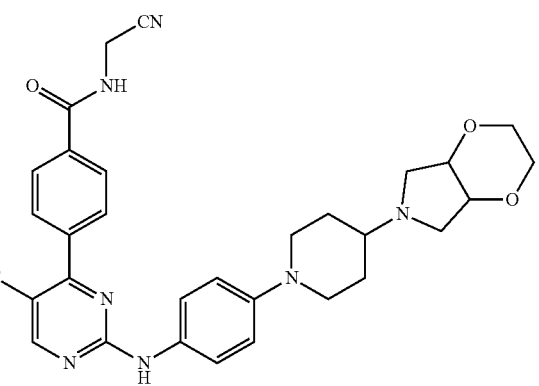

| 51 | 52 |
|---|---|
| N-(Cyanomethyl)-4-(5-fluoro-2-((4-(4-(tetrahydro-2H-[1,4]dioxino[2,3-c]pyrrol-6(3H)-yl)piperidin-1-yl)phenyl)amino)pyrimidin-4-yl)benzamide | N-(Cyanomethyl)-4-(5-methyl-2-((4-(4-(5-methyl-1,3,4-oxadiazol-2-yl)piperazin-1-yl)phenyl)amino)pyrimidin-4-yl)benzamide |

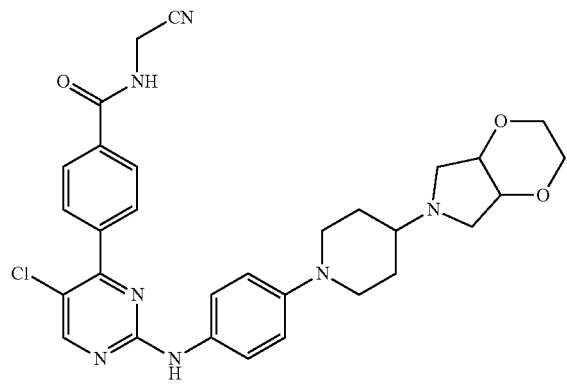 [SMILES: N#CCNC(=O)c1ccc(-c2nc(Nc3ccc(N4CCC(N5CC6OCCOC6C5)CC4)cc3)ncc2Cl)cc1]

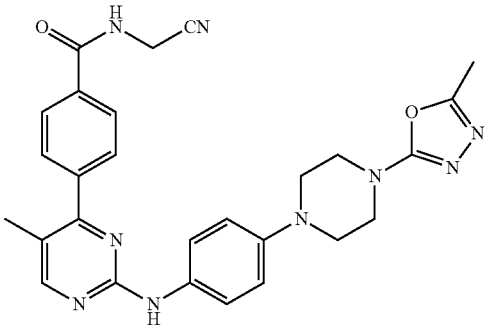

N-(Cyanomethyl)-4-(5-fluoro-2-((4-(4-(5-methyl-1,3,4-oxadiazol-2-yl)piperidin-1-yl)phenyl)amino)pyrimidin-4-yl)benzamide N-(Cyanomethyl)-4-(5-fluoro-2-((4-(4-(5-methyl-1,3,4-oxadiazol-2-yl)piperazin-1-yl)phenyl)amino)pyrimidin-4-yl)benzamide

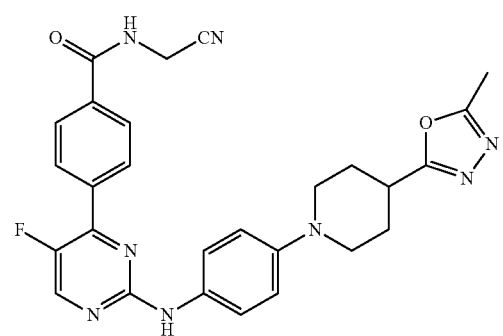 [SMILES: Cc1nnc(C2CCN(c3ccc(Nc4ncc(F)c(-c5ccc(C(=O)NCC#N)cc5)n4)cc3)CC2)o1]

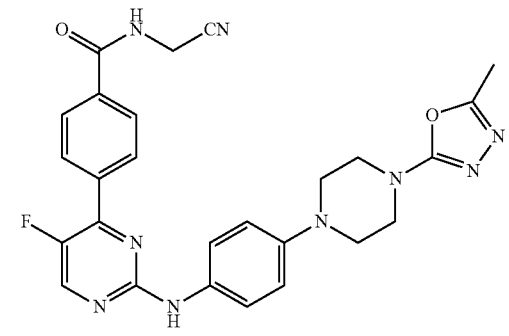

4-(5-Chloro-2-((4-(4-(5-methyl-1,3,4-oxadiazol-2-yl)piperidin-1-yl)phenyl)amino)pyrimidin-4-yl)-N-(cyanomethyl)benzamide 4-(5-Chloro-2-((4-(4-(5-methyl-1,3,4-oxadiazol-2-yl)piperazin-1-yl)phenyl)amino)pyrimidin-4-yl)-N-(cyanomethyl)benzamide

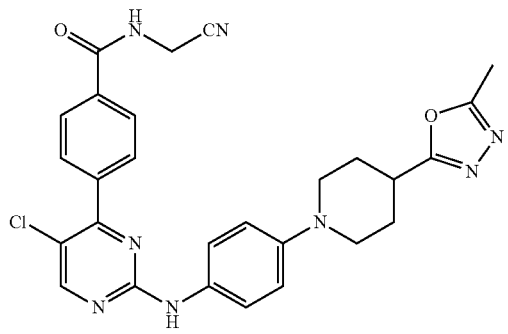 [SMILES: Cc1nnc(C2CCN(c3ccc(Nc4ncc(Cl)c(-c5ccc(C(=O)NCC#N)cc5)n4)cc3)CC2)o1]

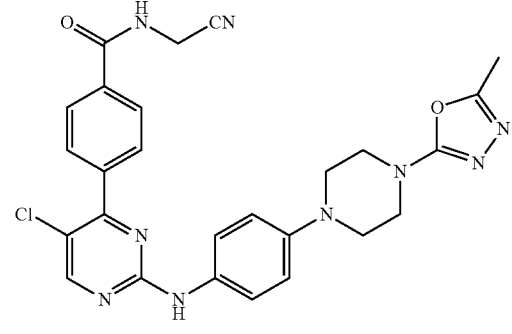 [SMILES: Cc1nnc(N2CCN(c3ccc(Nc4ncc(Cl)c(-c5ccc(C(=O)NCC#N)cc5)n4)cc3)CC2)o1]

4-(2-((4-(4-(3-Thia-6-azabicyclo[3.1.1]heptan-6-yl)piperidin-1-yl)phenyl)amino)pyrimidin-4-yl)-N-(cyanomethyl)benzamide

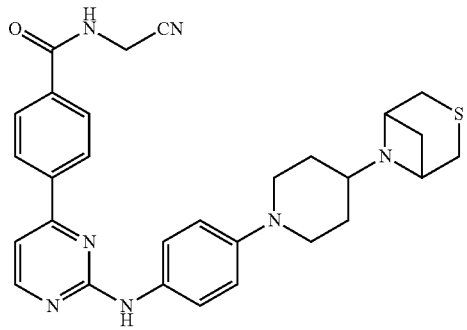 [SMILES: N#CCNC(=O)c1ccc(-c2ccnc(Nc3ccc(N4CCC(N5C6CSCC5C6)CC4)cc3)n2)cc1]

4-(2-((4-(4-(3-Thia-6-azabicyclo[3.1.1]heptan-6-yl)piperidin-1-yl)phenyl)amino)-5-methylpyrimidin-4-yl)-N-(cyanomethyl)benzamide

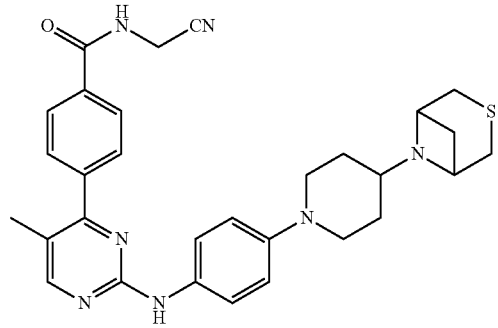 [SMILES: Cc1cnc(Nc2ccc(N3CCC(N4C5CSCC4C5)CC3)cc2)nc1-c1ccc(C(=O)NCC#N)cc1]

4-(2-((4-(4-(3-Thia-6-azabicyclo[3.1.1]heptan-6-yl)piperidin-1-yl)phenyl)amino)-5-fluoropyrimidin-4-yl)-N-(cyanomethyl)benzamide

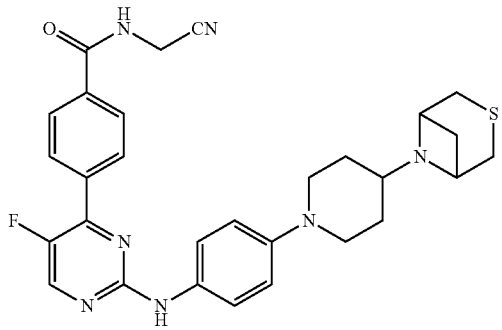 [SMILES: N#CCNC(=O)c1ccc(-c2nc(Nc3ccc(N4CCC(N5C6CSCC5C6)CC4)cc3)ncc2F)cc1]

4-(2-((4-(4-(3-Thia-6-azabicyclo[3.1.1]heptan-6-yl)piperidin-1-yl)phenyl)amino)-5-chloropyrimidin-4-yl)-N-(cyanomethyl)benzamide

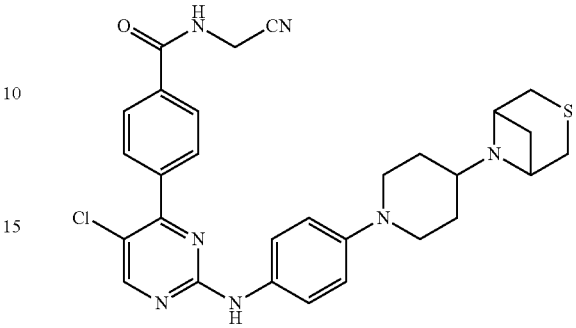

It will be appreciated that in any of the above mentioned reactions any reactive group in the substrate molecule may be protected, according to conventional chemical practice. Suitable protecting groups in any of the above mentioned reactions are those used conventionally in the art. The methods of formation and removal of such protecting groups are those conventional methods appropriate to the molecule being protected. T. W. Greene and P. G. M. Wuts "Protective groups in Organic Synthesis", John Wiley & Sons, Inc, 1999, $3^{rd}$ Ed., 201-245 along with references therein gives such conventional methods and are incorporated herein as references.

The novel compounds of the present invention can be formulated into suitable pharmaceutically acceptable compositions by combining with suitable excipients by techniques and processes and concentrations as are well known.

The compounds of formula (1) or pharmaceutical compositions containing them are useful as renin inhibitors suitable for humans and other warm blooded animals, and may be administered either by oral, topical or parenteral administration.

The pharmaceutical composition is provided by employing conventional techniques. Preferably the composition is in unit dosage form containing an effective amount of the active component, that is, the compounds of formula (1) according to this invention.

The quantity of active component, that is, the compounds of formula (1) according to this invention, in the pharmaceutical composition and unit dosage form thereof may be varied or adjusted widely depending upon the particular application method, the potency of the particular compound and the desired concentration.

The compounds of the present invention may be used alone or in combination with one or more other therapeutic agents which a skilled medical practitioner can easily identify. Such other therapeutic agent may be selected depending on the type of disease being treated, the severity, other medications being taken by the patients etc. Thus for example, for treatment of rheumatoid arthritis, one or more DMARDs may be used in combination with the compounds of the present invention.

Biological Activity:
In Vitro Study
Evaluation of JAK Inhibition.
NCEs were screened using in vitro JAK (1, 2 and 3) kinase assay on ADP Glo platform (Promega). Fixed amount of recombinant purified human JAK (25 ng of JAK1 and 10 ng of JAK2 and JAK3 per reaction, from Life Technologies Ltd) were incubated with increasing concentration of NCEs in 1× kinase reaction buffer (40 mM Tris-Cl, pH7.5, 20 mM $MgCl_2$, 0.1 mg/ml BSA and 50 μM DTT). Enzymatic reaction was initiated by adding a substrate cocktail containing 50 μM of ATP (final concentration) and 5 μg for JAK1 and 2.5 μg for JAK2 and JAK3 of polyGln$_4$Tyr$_1$ (Signal Chem) in total 25 μl of reaction in 96 well plate. The reaction was incubated at room temperature for 1 hr.

After 1 hr of incubation equal volume (25 μl per reaction) of ADP Glo was added and incubated at room temperature for 40 min.

This was followed by addition of kinase detection reagent (50 μl per reaction) and incubation at room temperature for 30 min. Finally, plate was read for luminescence at an integration time of 500 millisecond per well.

Data were plotted taking Enzyme with no inhibitor set as the 100% kinase activity. $IC_{50}$ values were calculated using Graph Pad Prism software.

| Example No | JAK-1 $IC_{50}$ (nM) | JAK-2 $IC_{50}$ (nM) | JAK-3 $IC_{50}$ (nM) |
| --- | --- | --- | --- |
| 1 | 12.1 | 5.6 | 72 |
| 2 | 5.1 | 4 | 51 |
| 3 | 11.7 | 6.6 | 62.3 |
| 4 | 21 | 17 | 66 |
| 6 | 16 | 19 | 155 |
| 7 | 14 | 12 | 62 |
| 9 | 14 | 8 | 40 |
| 12 | 25 | 18 | 78 |
| 15 | 16 | 11 | 88 |
| 17 | 13 | 8 | 69 |
| 18 | 9 | 11 | 50 |
| 19 | 10 | 7 | 40 |
| 24 | 5 | 5 | 23 |
| 25 | 12 | 8 | 48 |
| 27 | 10 | 5 | 49 |
| 28 | 11 | 6 | 55 |
| 29 | 15 | 21 | 56 |
| 31 | 20 | 17 | 74 |
| 33 | 20 | 11 | 54 |
| 34 | 13 | 20 | 124 |
| 35 | 15 | 21 | 138 |
| 36 | 9.2 | 6.7 | 46.9 |
| 38 | 1.5 | 4.3 | ND |
| 39 | 8.8 | 5 | 50.7 |
| 40 | 1.3 | 2.8 | 32 |
| 41 | 0.6 | 2.5 | 10.7 |
| 42 | 2.5 | 4.3 | 59 |
| 43 | 1.2 | 2.6 | 52.3 |
| 44 | 6.7 | 4.9 | 16.6 |

*ND: Not determined

From the in vitro data it is clear that the synthesized compounds have nano molar potency against JAK-1, JAK-2 and JAK-3. Also synthesized compound showed selectivity to JAK-1 & JAK-2. Thus these compounds can be used as potential agent to treat human cancers, arthritis and skin immune disorders such as psoriasis.

In Vivo Study
Peptidogylcan Polysaccharide Polymers (PGPS) Arthritis.

Female Sprague dawley rats were primed with an intraarticular injection of 20 μl of PGPS at 0.5 mg/ml of rhamnose in the right ankle. At 2 weeks the ankle diameters were measured with plethysmometer and rats assigned to groups of similar distribution of initial joint diameters. Rats then received their first dose of compound followed 1 h later by an i.v. injection of 0.5 ml of PGPS (0.5 mg/ml of rhamnose) in the tail vein. Compounds were dosed at 10 mg/kg and ankle diameters measured for 3 days [i.e. day 15, 16, 17]. Values are given for day 16.

| Example No. | % Reduction in PAW inflammation at dose 10 mg/Kg |
| --- | --- |
| 1 | 51 |
| 3 | 56 |
| 4 | 52 |
| 17 | 57 |
| 24 | 41 |
| 25 | 63 |
| 29 | 43 |

Induction and Assessment of Arthritis (Collagen-Induced Arthritis).

Male DBAlj (8 to 12-weeks old) mice were injected native bovine type II collagen (Chondrex, Redmond, Wash.) was mixed with complete Freund's adjuvant and injected s.c. on days 0 and 21 at the base of the tail of (200 μg of type II collagen in 100 μl of emulsion). Animals were observed for clinical score and assigned to different groups of similar score. Mice were then dosed and determined for clinical scores for 3 weeks. The degree of arthritis was determined based on a clinical score of 0-4 per paw and summed for all four paws. Few of the synthesised compounds showed activity at 10 mg/kg BID dose.

The compounds of the present invention are suitable as JAK inhibitors and are useful for the treatment inflammatory conditions, autoimmune diseases, proliferative diseases, allergy, and transplant rejection, diseases involving impairment of cartilage turnover, congenital cartilage malformations, and/or diseases associated with hypersecretion of IL6 or interferons.

We claim:
1. A compound having the structure of general formula (I)

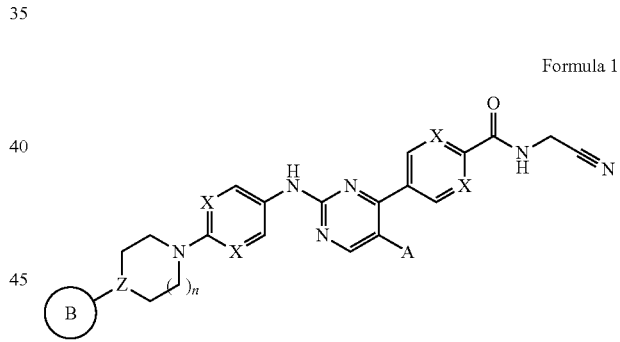

Formula 1 or pharmaceutically acceptable salts thereof;
wherein
X at each occurrence is independently selected from N or CH;
Z at each occurrence is independently selected from N or CH;
n is selected from 0, or 1 and
A is independently selected from hydrogen, halogen, $C_{1-4}$ alkyl, $CF_3$, CN, $CON(R_1)_2$, and $OC_{1-4}$alkyl;
Ring B is selected from following ring systems, each of which can be substituted -continued

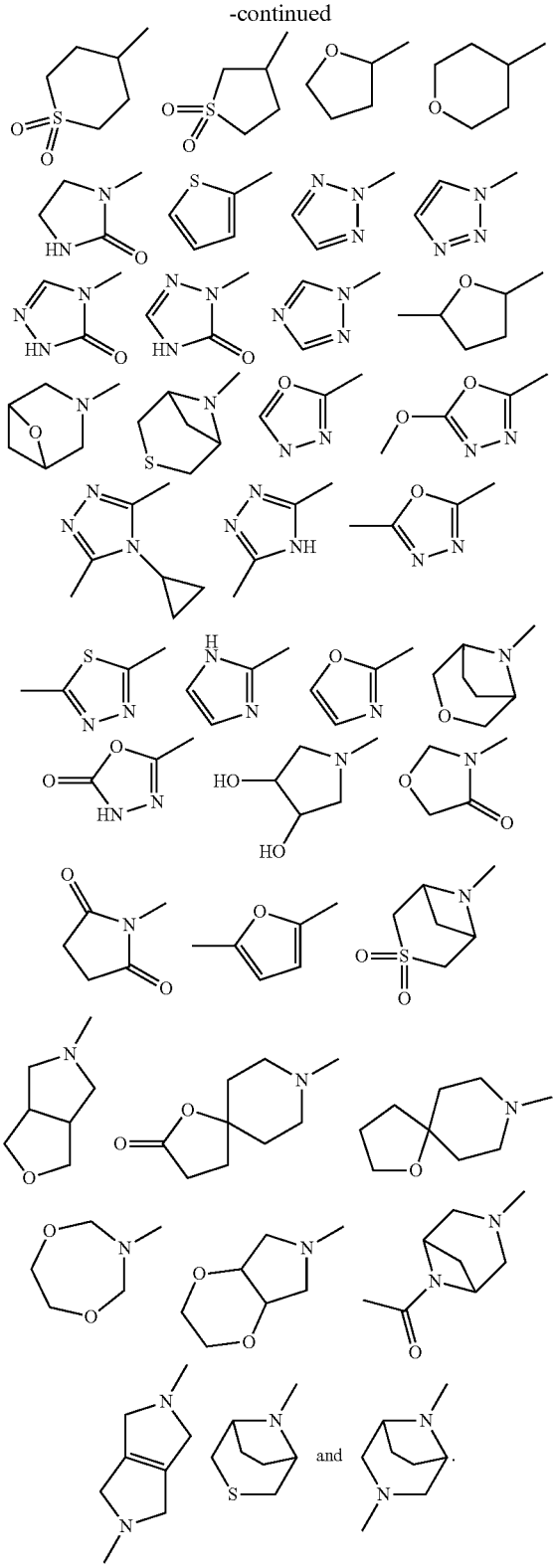

2. The compound according to claim 1 wherein substituents on the ring B wherever applicable is independently selected from H, OH, CN, $NH_2$, halogen, oxo, $OCF_3$, $CF_3$, $C_1$-$C_6$ alkyl, $OC_1$-$C_6$ alkyl, $(CH_2)_{1-6}OC_1$-$C_6$ alkyl, O—$(CH_2)_{0-4}OC_1$-$C_6$ alkyl, C(O)$NHC_1$-$C_6$ alkyl, NHC(O) $C_1$-$C_6$ alkyl, $S(O)_{0-2}C_1$-$C_6$ alkyl, $(CH_2)_{1-6}N(R_1)_2$, $(CH_2)_{1-6}NHC(=O)OR_1$, $(CH_2)_{1-6}$ NHC(=O)$R_1$, C(=O) $OR_1$, C(=O)$R_1$, $(CH_2)_{1-4}C(=O)$ $NHR_1$, $(CH_2)_{0-4}O$ $(CH_2)_{0-4}Ar_1$, $(CH_2)_{0-4}NH(CH_2)_{0-4}Ar_1$, $(CH_2)_{0-4}$ $Ar_1$, $(CH_2)_{0-4}C(O)(CH_2)_{0-4}Ar_1$, $(CH_2)_{0-4}C(=O)$ $O(CH_2)_{0-4}$ $Ar_1$, and $(CH_2)_{0-4}C(=O)NR_1(CH_2)_{0-4}Ar_1$.

3. The compound according to claim 1 wherein $R_1$ at each occurrence is independently selected from hydrogen, $C_1$-$C_4$ alkyl, $C_1$-$C_4$ haloalkyl, and $C_3$-$C_7$ cycloalkyl groups.

4. The compound according to claim 2 wherein $Ar_1$ at each iteration is independently selected from unsubstituted or substituted aryl or heterocyclic ring substituted with one, two, three or four substituents.

5. The compounds according to claim 4 wherein substituents on $Ar_1$ are independently selected from the group comprising of OH, CN, $NH_2$, halogen, $OCF_3$, $CF_3$, $C_1$-$C_6$ alkyl, $OC_1$-$C_6$alkyl, $(CH_2)_{1-6}OC_1$-$C_6$ alkyl, O—$(CH_2)_{0-4}OC_1$-$C_6$ alkyl, C(O)$NHC_1$-$C_6$ alkyl, NHC(O)$C_1$-$C_6$ alkyl, $S(O)_{0-2}C_1$-$C_6$ alkyl, $(CH_2)_{1-6}N(R_1)_2$, $(CH_2)_{1-6}NHC$ $(=O)OR_1$, $(CH_2)_{1-6}NHC(=O)R_1$, C(=O)$OR_1$ or —C(=O)$R_1$, and $CH_2(CH_2)_{0-4}C(=O)$ $NHR_1$.

6. The compound as claimed in claim 1, selected from the group consisting of:
N-(Cyanomethyl)-4-(2-((4-(4-(2-oxopyrrolidin-1-yl)piperidin-1-yl)phenyl)amino)pyrimidin-4-yl)benzamide;
N-(Cyanomethyl)-4-(2-((4-(4-(1,1-dioxidoisothiazolidin-2-yl) piperidin-1-yl)phenyl)amino)pyrimidin-4-yl)benzamide;
N-(Cyanomethyl)-4-(2-((4-(4-morpholinopiperidin-1-yl) phenyl)amino)pyrimidin-4-yl)benzamide;
4-(2-((4-(4-(1H-1,2,4-Triazol-1-yl)piperidin-1-yl)phenyl) amino)pyrimidin-4-yl)-N-(cyanomethyl)benzamide;
4-(2-((4-(4-(1H-Pyrazol-1-yl)piperidin-1-yl)phenyl) amino)pyrimidin-4-yl)-N-(cyanomethyl)benzamide;
4-(2-((4-([1,3'-Bipyrrolidin]-1'-yl)phenyl)amino)pyrimidin-4-yl)-N-(cyanomethyl)benzamide;
N-(cyanomethyl)-4-(2-((4-(4-(1,1-dioxidotetrahydro-2H-thiopyran-4-yl)piperazin-1-yl)phenyl)amino)pyrimidin-4-yl)benzamide;
N-(Cyanomethyl)-4-(2-((4-(4-(furan-2-yl)piperidin-1-yl) phenyl)amino)pyrimidin-4-yl)benzamide;
N-(Cyanomethyl)-4-(2-((4-(4-(1,1-dioxidotetrahydrothiophen-3-yl)piperazin-1-yl)phenyl)amino)pyrimidin-4-yl)benzamide;
N-(Cyanomethyl)-4-(2-((4-(4-(2,5-dioxopyrrolidin-1-yl) piperidin-1-yl)phenyl)amino)pyrimidin-4-yl)benzamide;
N-(Cyanomethyl)-4-(2-((4-(4-(thiophen-2-yl)piperidin-1-yl)phenyl)amino)pyrimidin-4-yl)benzamide;
N-(Cyanomethyl)-4-(2-((4-(4-(2-oxooxazolidin-3-yl)piperidin-1-yl)phenyl)amino)pyrimidin-4-yl)benzamide;
N-(Cyanomethyl)-4-(2-((4-(4-(tetrahydrofuran-2-yl)piperidin-1-yl)phenyl)amino)pyrimidin-4-yl)benzamide;
N-(Cyanomethyl)-4-(2-((4-(4-(5-methylfuran-2-yl)piperidin-1-yl)phenyl)amino)pyrimidin-4-yl)benzamide;
N-(Cyanomethyl)-4-(2-((4-(4-(tetrahydro-2H-pyran-4-yl) piperazin-1-yl)phenyl)amino)pyrimidin-4-yl)benzamide;
N-(Cyanomethyl)-4-(2-((4-(4-(5-methyltetrahydrofuran-2-yl)piperidin-1-yl)phenyl)amino)pyrimidin-4-yl)benzamide;
4-(2-((4-(4-(6-Oxa-3-azabicyclo[3.1.1]heptan-3-yl)piperidin-1-yl)phenyl)amino)pyrimidin-4-yl)-N-(cyanomethyl)benzamide;
N-(Cyanomethyl)-4-(2-((4-(4-(2-oxoimidazolidin-1-yl) piperidin-1-yl)phenyl)amino)pyrimidin-4-yl)benzamide;

4-(2-((4-(4-(1,3,4-Oxadiazol-2-yl)piperidin-1-yl)phenyl) amino)pyrimidin-4-yl)-N-(cyanomethyl)benzamide;
4-(2-((4-(4-(2H-1,2,3-Triazol-2-yl)piperidin-1-yl)phenyl) amino)pyrimidin-4-yl)-N-(cyano methyl)benzamide;
4-(2-((4-(4-(1H-1,2,3-Triazol-1-yl)piperidin-1-yl)phenyl) amino)pyrimidin-4-yl)-N-(cyano methyl)benzamide;
N-(Cyanomethyl)-4-(2-((4-(4-(5-oxo-1H-1,2,4-triazol-4 (5H)-yl)piperidin-1-yl)phenyl)amino)pyrimidin-4-yl) benzamide;
N-(Cyanomethyl)-4-(2-((4-(4-(5-oxo-4,5-dihydro-1H-1, 2,4-triazol-1-yl)piperidin-1-yl)phenyl)amino)pyrimidin-4-yl)benzamide;
4-(2-((4-(4-(1-Oxa-8-azaspiro[4.5]decan-8-yl)piperidin-1-yl)phenyl)amino)pyrimidin-4-yl)-N-(cyanomethyl) benzamide;
N-(Cyanomethyl)-4-(2-((4-(4-(5-methyl-1,3,4-oxadiazol-2-yl)piperidin-1-yl)phenyl)amino)pyrimidin-4-yl)benzamide;
N-(Cyanomethyl)-4-(2-((4-(4-(5-methyl-1,3,4-thiadiazol-2-yl)piperidin-1-yl)phenyl)amino)pyrimidin-4-yl)benzamide;
N-(Cyanomethyl)-4-(2-((4-(4-(tetrahydro-2H-[1,4]dioxino[2,3-c]pyrrol-6(3H)-yl)piperidin-1-yl)phenyl) amino)pyrimidin-4-yl)benzamide;
N-(Cyanomethyl)-4-(2-((4-(4-(2-oxo-1-oxa-8-azaspiro [4.5]decan-8-yl)piperidin-1-yl)phenyl)amino)pyrimidin-4-yl)benzamide;
N-(Cyanomethyl)-4-(2-((4-(4-(5-oxo-4,5-dihydro-1,3,4-oxadiazol-2-yl)piperidin-1-yl)phenyl)amino)pyrimidin-4-yl)benzamide;
N-(Cyanomethyl)-4-(2-((4-(4-(4-cyclopropyl-5-methyl-4H-1,2,4-triazol-3-yl) piperidin-1-yl)phenyl)amino) pyrimidin-4-yl)benzamide;
N-(Cyanomethyl)-4-(2-((4-(4-(5-methoxy-1,3,4-oxadiazol-2-yl)piperidin-1-yl)phenyl)amino)pyrimidin-4-yl) benzamide;
4-(2-((4-(4-(1,4-Dioxepan-6-yl)piperazin-1-yl)phenyl) amino)pyrimidin-4-yl)-N-(cyanomethyl)benzamide;
N-(Cyanomethyl)-4-(2-((4-(4-(4,5-dihydro-1H-imidazol-2-yl)piperazin-1-yl)phenyl)amino)pyrimidin-4-yl)benzamide;
N-(Cyanomethyl)-4-(2-((4-(4-(4,5-dihydro-1H-imidazol-2-yl)piperidin-1-yl)phenyl)amino)pyrimidin-4-yl)benzamide;
N-(Cyanomethyl)-4-(2-((4-(3-(tetrahydro-2H-[1,4]dioxino[2,3-c]pyrrol-6(3H)-yl)pyrrolidin-1-yl)phenyl) amino)pyrimidin-4-yl)benzamide;
N-(Cyanomethyl)-4-(2-((4-(4-(5-methyl-1,3,4-oxadiazol-2-yl)piperazin-1-yl)phenyl)amino)pyrimidin-4-yl)benzamide;
N-(Cyanomethyl)-4-(2-((4-(4-(3,4-dihydroxypyrrolidin-1-yl)piperidin-1-yl)phenyl)amino)pyrimidin-4-yl)benzamide;
4-(2-((4-(4-(8-Oxa-3-azabicyclo[3.2.1]octan-3-yl)piperidin-1-yl)phenyl)amino)pyrimidin-4-yl)-N-(cyanomethyl)benzamide;
4-(2-((4-(4-(6-Acetyl-3,6-diazabicyclo[3.1.1]heptan-3-yl)piperidin-1-yl)phenyl)amino)pyrimidin-4-yl)-N-(cyanomethyl)benzamide;
N-(Cyanomethyl)-4-(5-methyl-2-((4-(4-morpholinopiperidin-1-yl)phenyl)amino)pyrimidin-4-yl)benzamide;
N-(Cyanomethyl)-4-(5-methyl-2-((4-(4-(2-oxopyrrolidin-1-yl)piperidin-1-yl)phenyl)amino)pyrimidin-4-yl) benzamide;
4-(2-((4-(4-(1-Oxa-8-azaspiro[4.5]decan-8-yl)piperidin-1-yl)phenyl)amino)-5-methylpyrimidin-4-yl)-N-(cyanomethyl)benzamide;
N-(Cyanomethyl)-4-(5-methyl-2-((4-(4-(5-methyl-1,3,4-oxadiazol-2-yl)piperidin-1-yl)phenyl)amino)pyrimidin-4-yl)benzamide;
N-(Cyanomethyl)-4-(5-fluoro-2-((4-(4-morpholinopiperidin-1-yl)phenyl)amino)pyrimidin-4-yl)benzamide;
4-(5-Chloro-2-((4-(4-morpholinopiperidin-1-yl)phenyl) amino)pyrimidin-4-yl)-N-(cyanomethyl)benzamide;
N-(Cyanomethyl)-4-(5-fluoro-2-((4-(4-(2-oxopyrrolidin-1-yl)piperidin-1-yl)phenyl)amino)pyrimidin-4-yl)benzamide;
4-(5-Chloro-2-((4-(4-(2-oxopyrrolidin-1-yl)piperidin-1-yl)phenyl)amino)pyrimidin-4-yl)-N-(cyanomethyl) benzamide;
4-(2-((4-(4-(6-Oxa-3-azabicyclo[3.1.1]heptan-3-yl)piperidin-1-yl)phenyl)amino)-5-methylpyrimidin-4-yl)-N-(cyanomethyl)benzamide;
4-(2-((4-(4-(6-Oxa-3-azabicyclo[3.1.1]heptan-3-yl)piperidin-1-yl)phenyl)amino)-5-fluoropyrimidin-4-yl)-N-(cyanomethyl)benzamide;
-(2-((4-(4-(6-Oxa-3-azabicyclo[3.1.1]heptan-3-yl)piperidin-1-yl)phenyl)amino)-5-chloropyrimidin-4-yl)-N-(cyanomethyl)benzamide;
N-(Cyanomethyl)-4-(5-methyl-2-((4-(4-(tetrahydro-2H-[1,4]dioxino[2,3-c]pyrrol-6(3H)-yl)piperidin-1-yl)phenyl)amino)pyrimidin-4-yl)benzamide;
N-(Cyanomethyl)-4-(5-fluoro-2-((4-(4-(tetrahydro-2H-[1,4]dioxino[2,3-c]pyrrol-6(3H)-yl)piperidin-1-yl)phenyl)amino)pyrimidin-4-yl)benzamide;
4-(5-Chloro-2-((4-(4-(tetrahydro-2H-[1,4]dioxino[2,3-c] pyrrol-6(3H)-yl)piperidin-1-yl)phenyl)amino)pyrimidin-4-yl)-N-(cyanomethyl)benzamide;
N-(Cyanomethyl)-4-(5-fluoro-2-((4-(4-(5-methyl-1,3,4-oxadiazol-2-yl)piperidin-1-yl)phenyl)amino)pyrimidin-4-yl)benzamide;
4-(5-Chloro-2-((4-(4-(5-methyl-1,3,4-oxadiazol-2-yl)piperidin-1-yl)phenyl)amino)pyrimidin-4-yl)-N-(cyanomethyl)benzamide;
N-(Cyanomethyl)-4-(5-methyl-2-((4-(4-(5-methyl-1,3,4-oxadiazol-2-yl)piperazin-1-yl)phenyl)amino)pyrimidin-4-yl)benzamide;
N-(Cyanomethyl)-4-(5-fluoro-2-((4-(4-(5-methyl-1,3,4-oxadiazol-2-yl)piperazin-1-yl)phenyl)amino)pyrimidin-4-yl)benzamide;
4-(5-Chloro-2-((4-(4-(5-methyl-1,3,4-oxadiazol-2-yl)piperazin-1-yl)phenyl)amino)pyrimidin-4-yl)-N-(cyanomethyl)benzamide;
4-(2-((4-(4-(3-Thia-6-azabicyclo[3.1.1]heptan-6-yl)piperidin-1-yl)phenyl)amino)pyrimidin-4-yl)-N-(cyanomethyl)benzamide;
4-(2-((4-(4-(3-Thia-6-azabicyclo[3.1.1]heptan-6-yl)piperidin-1-yl)phenyl)amino)-5-methylpyrimidin-4-yl)-N-(cyanomethyl)benzamide;
4-(2-((4-(4-(3-Thia-6-azabicyclo[3.1.1]heptan-6-yl)piperidin-1-yl)phenyl)amino)-5-fluoropyrimidin-4-yl)-N-(cyanomethyl)benzamide; and
4-(2-((4-(4-(3-Thia-6-azabicyclo[3.1.1]heptan-6-yl)piperidin-1-yl)phenyl)amino)-5-chloropyrimidin-4-yl)-N-(cyanomethyl)benzamide.

7. The compound as claimed in claim 1, selected from the group consisting of:
N-(Cyanomethyl)-4-(2-((4-(4-(2-oxopyrrolidin-1-yl)piperidin-1-yl)phenyl)amino)pyrimidin-4-yl)benzamide;
N-(Cyanomethyl)-4-(2-((4-(4-(1,1-dioxidoisothiazolidin-2-yl) piperidin-1-yl)phenyl)amino)pyrimidin-4-yl)benzamide;
N-(Cyanomethyl)-4-(2-((4-(4-morpholinopiperidin-1-yl) phenyl)amino)pyrimidin-4-yl)benzamide;

4-(2-((4-(4-(1H-1,2,4-Triazol-1-yl)piperidin-1-yl)phenyl)amino)pyrimidin-4-yl)-N-(cyanomethyl)benzamide;
4-(2-((4-(4-(1H-Pyrazol-1-yl)piperidin-1-yl)phenyl)amino)pyrimidin-4-yl)-N-(cyanomethyl)benzamide;
4-(2-((4-([1,3'-Bipyrrolidin]-1'-yl)phenyl)amino)pyrimidin-4-yl)-N-(cyanomethyl)benzamide;
N-(cyanomethyl)-4-(2-((4-(4-(1,1-dioxidotetrahydro-2H-thiopyran-4-yl)piperazin-1-yl)phenyl)amino)pyrimidin-4-yl)benzamide;
N-(Cyanomethyl)-4-(2-((4-(4-(furan-2-yl)piperidin-1-yl)phenyl)amino)pyrimidin-4-yl)benzamide;
N-(Cyanomethyl)-4-(2-((4-(4-(1,1-dioxidotetrahydrothiophen-3-yl)piperazin-1-yl)phenyl)amino)pyrimidin-4-yl)benzamide;
N-(Cyanomethyl)-4-(2-((4-(4-(2,5-dioxopyrrolidin-1-yl)piperidin-1-yl)phenyl)amino)pyrimidin-4-yl)benzamide;
N-(Cyanomethyl)-4-(2-((4-(4-(thiophen-2-yl)piperidin-1-yl)phenyl)amino)pyrimidin-4-yl)benzamide;
N-(Cyanomethyl)-4-(2-((4-(4-(2-oxooxazolidin-3-yl)piperidin-1-yl)phenyl)amino)pyrimidin-4-yl)benzamide;
N-(Cyanomethyl)-4-(2-((4-(4-(tetrahydrofuran-2-yl)piperidin-1-yl)phenyl)amino)pyrimidin-4-yl)benzamide;
N-(Cyanomethyl)-4-(2-((4-(4-(5-methylfuran-2-yl)piperidin-1-yl)phenyl)amino)pyrimidin-4-yl)benzamide;
N-(Cyanomethyl)-4-(2-((4-(4-(tetrahydro-2H-pyran-4-yl)piperazin-1-yl)phenyl)amino)pyrimidin-4-yl)benzamide;
N-(Cyanomethyl)-4-(2-((4-(4-(5-methyltetrahydrofuran-2-yl)piperidin-1-yl)phenyl)amino)pyrimidin-4-yl)benzamide;
4-(2-((4-(4-(6-Oxa-3-azabicyclo[3.1.1]heptan-3-yl)piperidin-1-yl)phenyl)amino)pyrimidin-4-yl)-N-(cyanomethyl)benzamide;
N-(Cyanomethyl)-4-(2-((4-(4-(2-oxoimidazolidin-1-yl)piperidin-1-yl)phenyl)amino)pyrimidin-4-yl)benzamide;
4-(2-((4-(4-(1,3,4-Oxadiazol-2-yl)piperidin-1-yl)phenyl)amino)pyrimidin-4-yl)-N-(cyanomethyl)benzamide;
4-(2-((4-(4-(2H-1,2,3-Triazol-2-yl)piperidin-1-yl)phenyl)amino)pyrimidin-4-yl)-N-(cyano methyl)benzamide;
4-(2-((4-(4-(1H-1,2,3-Triazol-1-yl)piperidin-1-yl)phenyl)amino)pyrimidin-4-yl)-N-(cyano methyl)benzamide;
N-(Cyanomethyl)-4-(2-((4-(4-(5-oxo-1H-1,2,4-triazol-4(5H)-yl) piperidin-1-yl)phenyl)amino)pyrimidin-4-yl) benzamide;
N-(Cyanomethyl)-4-(2-((4-(4-(5-oxo-4,5-dihydro-1H-1,2,4-triazol-1-yl)piperidin-1-yl)phenyl)amino)pyrimidin-4-yl)benzamide;
4-(2-((4-(4-(1-Oxa-8-azaspiro[4.5]decan-8-yl)piperidin-1-yl)phenyl)amino)pyrimidin-4-yl)-N-(cyanomethyl)benzamide;
N-(Cyanomethyl)-4-(2-((4-(4-(5-methyl-1,3,4-oxadiazol-2-yl)piperidin-1-yl)phenyl)amino)pyrimidin-4-yl)benzamide;
N-(Cyanomethyl)-4-(2-((4-(4-(5-methyl-1,3,4-thiadiazol-2-yl)piperidin-1-yl)phenyl)amino)pyrimidin-4-yl)benzamide;
N-(Cyanomethyl)-4-(2-((4-(4-(tetrahydro-2H-[1,4]dioxino[2,3-c]pyrrol-6(3H)-yl)piperidin-1-yl)phenyl)amino)pyrimidin-4-yl)benzamide;
N-(Cyanomethyl)-4-(2-((4-(4-(2-oxo-1-oxa-8-azaspiro[4.5]decan-8-yl)piperidin-1-yl)phenyl)amino)pyrimidin-4-yl)benzamide;
N-(Cyanomethyl)-4-(2-((4-(4-(5-oxo-4,5-dihydro-1,3,4-oxadiazol-2-yl)piperidin-1-yl)phenyl)amino)pyrimidin-4-yl)benzamide;
N-(Cyanomethyl)-4-(2-((4-(4-(4-cyclopropyl-5-methyl-4H-1,2,4-triazol-3-yl) piperidin-1-yl)phenyl)amino) pyrimidin-4-yl)benzamide;
N-(Cyanomethyl)-4-(2-((4-(4-(5-methoxy-1,3,4-oxadiazol-2-yl)piperidin-1-yl)phenyl)amino)pyrimidin-4-yl)benzamide;
4-(2-((4-(4-(1,4-Dioxepan-6-yl)piperazin-1-yl)phenyl)amino)pyrimidin-4-yl)-N-(cyanomethyl)benzamide;
N-(Cyanomethyl)-4-(2-((4-(4-(4,5-dihydro-1H-imidazol-2-yl)piperazin-1-yl)phenyl)amino)pyrimidin-4-yl)benzamide;
N-(Cyanomethyl)-4-(2-((4-(4-(4,5-dihydro-1H-imidazol-2-yl)piperidin-1-yl)phenyl)amino)pyrimidin-4-yl)benzamide;
N-(Cyanomethyl)-4-(2-((4-(3-(tetrahydro-2H-[1,4]dioxino[2,3-c]pyrrol-6(3H)-yl)pyrrolidin-1-yl)phenyl)amino)pyrimidin-4-yl)benzamide;
N-(Cyanomethyl)-4-(2-((4-(4-(5-methyl-1,3,4-oxadiazol-2-yl)piperazin-1-yl)phenyl)amino)pyrimidin-4-yl)benzamide;
N-(Cyanomethyl)-4-(2-((4-(4-(3,4-dihydroxypyrrolidin-1-yl)piperidin-1-yl)phenyl)amino)pyrimidin-4-yl)benzamide;
4-(2-((4-(4-(8-Oxa-3-azabicyclo[3.2.1]octan-3-yl)piperidin-1-yl)phenyl)amino)pyrimidin-4-yl)-N-(cyanomethyl)benzamide;
4-(2-((4-(4-(6-Acetyl-3,6-diazabicyclo [3.1.1]heptan-3-yl)piperidin-1-yl)phenyl)amino)pyrimidin-4-yl)-N-(cyanomethyl)benzamide;
N-(Cyanomethyl)-4-(5-methyl-2-((4-(4-morpholinopiperidin-1-yl)phenyl)amino)pyrimidin-4-yl)benzamide;
N-(Cyanomethyl)-4-(5-methyl-2-((4-(4-(2-oxopyrrolidin-1-yl)piperidin-1-yl)phenyl)amino)pyrimidin-4-yl)benzamide;
4-(2-((4-(4-(1-Oxa-8-azaspiro[4.5]decan-8-yl)piperidin-1-yl)phenyl)amino)-5-methylpyrimidin-4-yl)-N-(cyanomethyl)benzamide;
N-(Cyanomethyl)-4-(5-methyl-2-((4-(4-(5-methyl-1,3,4-oxadiazol-2-yl)piperidin-1-yl)phenyl)amino)pyrimidin-4-yl)benzamide;
N-(Cyanomethyl)-4-(5-fluoro-2-((4-(4-morpholinopiperidin-1-yl)phenyl)amino)pyrimidin-4-yl)benzamide; and
4-(5-Chloro-2-((4-(4-morpholinopiperidin-1-yl)phenyl)amino)pyrimidin-4-yl)-N-(cyanomethyl)benzamide.

8. A pharmaceutical composition comprising a therapeutically effective amount of a compound of Formula (I) as claimed in claim 1, and optionally one or more pharmaceutically acceptable carriers, diluents or excipients.

9. A method of treating allergy and transplant rejection, diseases involving impairment of cartilage turnover, congenital cartilage malformations, and/or diseases associated with hypersecretion of IL6 or interferons wherein the JAK kinase has a pathophysiological function comprising administering a composition according to claim 8 to a subject in need thereof.

10. The compound as claimed in claim 1, which is:
N-(Cyanomethyl)-4-(5-fluoro-2-((4-(4-morpholinopiperidin-1-yl)phenyl)amino)pyrimidin-4-yl)benzamide.

* * * * *